United States Patent
Kadoma et al.

(10) Patent No.: US 8,981,366 B2
(45) Date of Patent: Mar. 17, 2015

(54) HETEROCYCLIC COMPOUND, LIGHT-EMITTING ELEMENT, DISPLAY MODULE, LIGHTING MODULE, LIGHT-EMITTING DEVICE, DISPLAY DEVICE, LIGHTING DEVICE, AND ELECTRONIC DEVICE

(71) Applicant: Semiconductor Energy Laboratory Co., Ltd., Kanagawa-ken (JP)

(72) Inventors: Hiroshi Kadoma, Kanagawa (JP); Yuko Kawata, Kanagawa (JP); Hiromi Seo, Kanagawa (JP); Tatsuyoshi Takahashi, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 14/267,308

(22) Filed: May 1, 2014

(65) Prior Publication Data

US 2014/0330017 A1    Nov. 6, 2014

(30) Foreign Application Priority Data

May 3, 2013    (JP) ................ 2013-097201

(51) Int. Cl.
*H01L 51/50* (2006.01)
*C07D 403/10* (2006.01)
*H01L 51/00* (2006.01)

(52) U.S. Cl.
CPC .................... *H01L 51/0072* (2013.01)
USPC .............................. 257/40; 544/343

(58) Field of Classification Search
USPC .............................. 544/343; 257/40
See application file for complete search history.

(56) References Cited

U.S. PATENT DOCUMENTS

| | | |
|---|---|---|
| 2012/0205632 A1 | 8/2012 | Shitagaki et al. |
| 2012/0205687 A1 | 8/2012 | Yamazaki et al. |
| 2014/0034924 A1 | 2/2014 | Kawata et al. |

FOREIGN PATENT DOCUMENTS

JP    2007-015933 A    1/2007

OTHER PUBLICATIONS

Kondakova, M.E. et al., "High-Efficiency, Low-Voltage Phosphorescent Organic Light-Emitting Diode Devices with Mixed Host," Journal of Applied Physics, 2008, vol. 104, pp. 094501-1-094501-17.

*Primary Examiner* — Kristin Vajda
(74) *Attorney, Agent, or Firm* — Husch Blackwell LLP

(57) ABSTRACT

Provided is a heterocyclic compound that can be used for a carrier-transport material, a host material, or a light-emitting material in a light-emitting element. The heterocyclic compound has an indolo[3,2,1-jk]carbazole skeleton and a dibenzo[f,h]quinoxaline skeleton which are linked to each other through an arylene group. The wide band gap of the heterocyclic compound allows excitation of a green-emissive phosphorescent material, which contributes to the formation of a highly efficient light-emitting element.

15 Claims, 22 Drawing Sheets

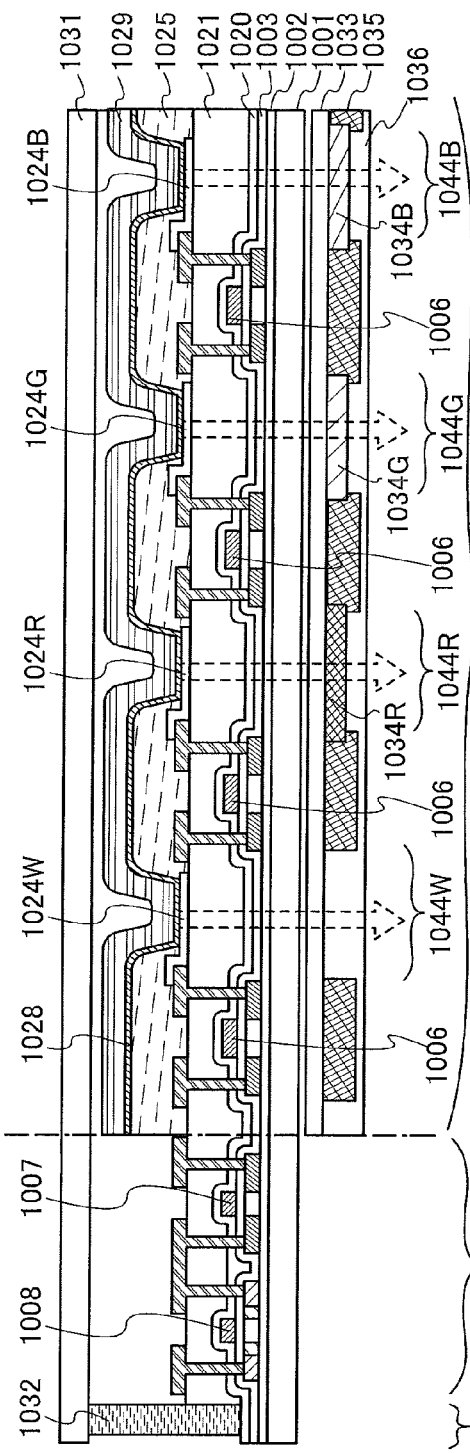
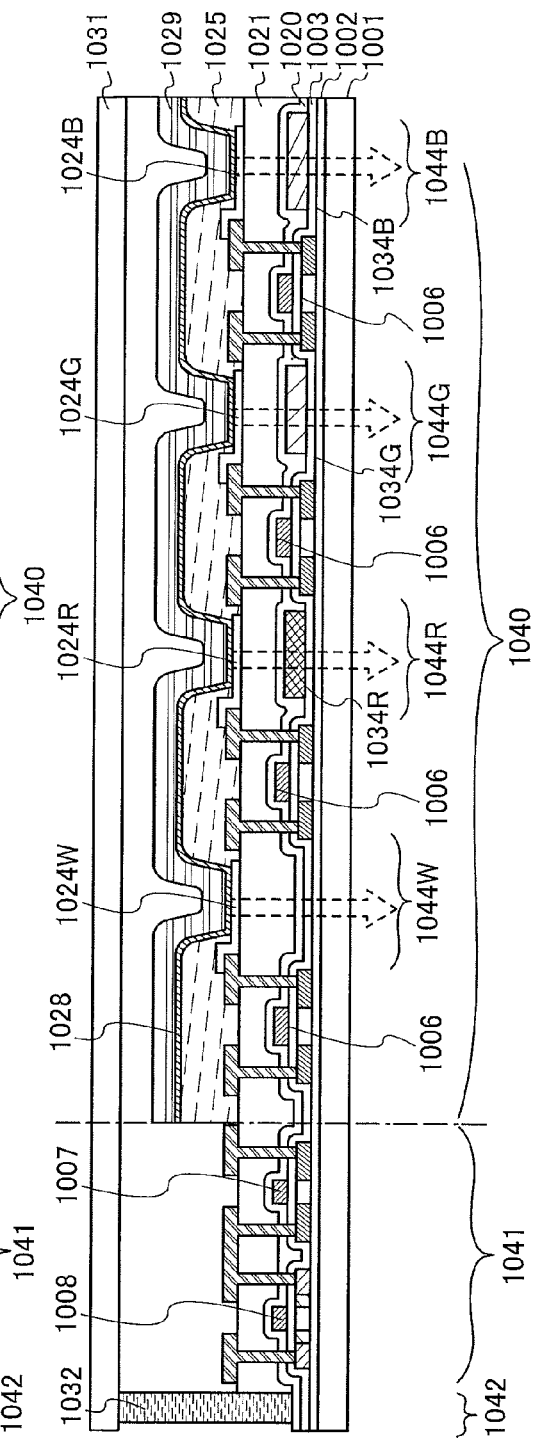
FIG. 4A
FIG. 4B

HETEROCYCLIC COMPOUND, LIGHT-EMITTING ELEMENT, DISPLAY MODULE, LIGHTING MODULE, LIGHT-EMITTING DEVICE, DISPLAY DEVICE, LIGHTING DEVICE, AND ELECTRONIC DEVICE

BACKGROUND OF THE INVENTION

1. Field of the Invention

The present invention relates to a heterocyclic compound that can be used as a light-emitting element material. The present invention relates to a light-emitting element, a display module, a lighting module, a light-emitting device, a display device, a lighting device, and an electronic device each using the heterocyclic compound.

2. Description of the Related Art

As next generation lighting devices or display devices, display devices using light-emitting elements (organic EL elements) in which organic compounds are used as light-emitting substances have been rapidly developed because of their advantages of thinness, lightweightness, high speed response to input signals, low power consumption, and the like.

In an organic EL element, voltage application between electrodes, between which a light-emitting layer is interposed, causes recombination of electrons and holes injected from the electrodes, which brings a light-emitting substance into an excited state, and the return from the excited state to the ground state is accompanied by light emission. Since the wavelength of light emitted from a light-emitting substance depends on the light-emitting substance, use of different types of organic compounds as light-emitting substances makes it possible to obtain light-emitting elements which exhibit various wavelengths, i.e., various colors.

In the case of display devices which are used to display images, such as displays, at least three-color light, i.e., red light, green light, and blue light is necessary for reproduction of full-color images. Furthermore, in application to lighting devices, it is ideal to obtain light thoroughly covering the visible light region for obtaining a high color rendering property, but in reality, light obtained by mixing two or more kinds of light having different wavelengths is often used for lighting application in many cases. It is known that, with a mixture of three-color light, i.e., red light, green light, and blue light, white light having a high color rendering property can be obtained.

Color of light emitted from a light-emitting substance depends on the substance, as described above. However, important performances as a light-emitting element, such as lifetime, power consumption, and emission efficiency, are not only dependent on a light-emitting substance but also greatly dependent on the materials in the layers other than the light-emitting layer, an element structure, and the like. Therefore, many kinds of materials for light-emitting elements are necessary for the growth of this field. For the above-described reasons, materials for light-emitting elements with a variety of molecular structures have been proposed (e.g., see Patent Document 1).

As is generally known, the generation ratio of a singlet excited state to a triplet excited state in a light-emitting element using electroluminescence is 1:3. Therefore, a light-emitting element in which a phosphorescent material capable of converting the triplet excited state to light emission is used as a light-emitting substance can theoretically obtain higher emission efficiency than a light-emitting element in which a fluorescent material capable of converting the singlet excited state to light emission is used as a light-emitting substance.

However, since the triplet excited state of a substance is at a lower energy level than its singlet excited state, a substance that emits phosphorescence has a higher singlet excited state than a substance that emits fluorescence when the emissions of the substances are at the same wavelength.

As a host material in a host-guest type light-emitting layer or a substance contained in a transport layer in contact with a light-emitting layer, a substance having a wider band gap or a higher triplet level ($T_1$, an energy difference between a triplet excited state and a singlet ground state) than a light-emitting substance is used for efficient conversion of excitation energy into light emission from the light-emitting substance.

Therefore, a host material and a carrier-transport material each having a further wider band gap are necessary in order to efficiently obtain phosphorescence. It is very difficult to develop a substance which has a wide band gap while enabling the production of a light-emitting element, with a low driving voltage and a high emission efficiency.

REFERENCE

Patent Document

[Patent Document 1] Japanese Published Patent Application No. 2007-015933

SUMMARY OF THE INVENTION

In view of the above, an object of one embodiment of the present invention is to provide a light-emitting element having a high emission efficiency. Another object of one embodiment of the present invention is to provide a light-emitting element with a low driving voltage.

Furthermore, another object of one embodiment of the present invention is to provide a novel heterocyclic compound that can be used for a carrier-transport material, a host material, or a light-emitting material in a light-emitting element. Specifically, an object of one embodiment of the present invention is to provide a heterocyclic compound that can gives a light-emitting element having favorable characteristics even when the heterocyclic compound is used in a light-emitting element emitting phosphorescence.

Another object of one embodiment of the present invention is to provide a heterocyclic compound which has a high triplet level.

Another object of one embodiment of the present invention is to provide a heterocyclic compound having a high carrier-transport property.

Another object of one embodiment of the present invention is to provide a light-emitting element containing the heterocyclic compound.

Another object of one embodiment of the present invention is to provide a display module, a lighting module, a light-emitting device, a lighting device, a display device, and an electronic device each using the heterocyclic compound.

It is only necessary that at least one of the above-described objects be achieved in the present invention.

One embodiment of the present invention is a heterocyclic compound represented by the following general formula (G0).

$$A^1\text{-}Ar\text{-}A^2 \tag{G0}$$

In the general formula (G0), $A^1$ represents a dibenzo[f,h]quinoxalinyl group, $A^2$ represents an indolo[3,2,1-jk]carbazolyl group, and Ar represents an arylene group having 6 to 13 carbon atoms. The dibenzo[f,h]quinoxalinyl group, the indolo[3,2,1-jk]carbazolyl group, and the arylene group each may be independently unsubstituted or have a substituent selected from an alkyl group having 1 to 6 carbon atoms and an aryl group having 6 to 13 carbon atoms.

One embodiment of the present invention is a heterocyclic compound represented by the following general formula (G1).

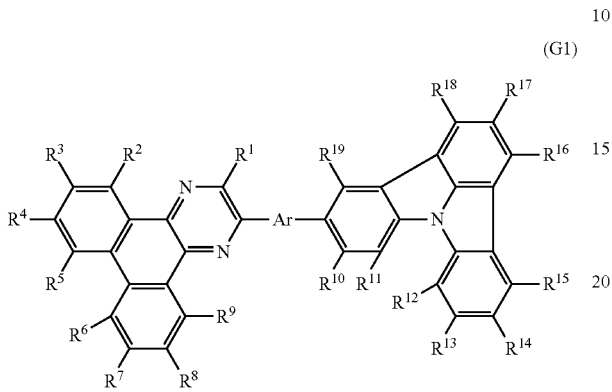

(G1)

In the above general formula (G1), $R^1$ to $R^{19}$ each independently represent any one of hydrogen, an alkyl group having 1 to 6 carbon atoms, and an aryl group having 6 to 13 carbon atoms, and Ar represents an arylene group having 6 to 13 carbon atoms.

Another embodiment of the present invention is a heterocyclic compound with the above structure, in which Ar is a substituted or unsubstituted phenylene group or a substituted or unsubstituted biphenyldiyl group.

Another embodiment of the present invention is a heterocyclic compound with the above structure, in which Ar is a substituted or unsubstituted phenylene group.

Another embodiment of the present invention is a heterocyclic compound with the above structure, in which Ar is a substituted or unsubstituted iia-phenylene group.

Another embodiment of the present invention is a heterocyclic compound represented by the following general formula (G2).

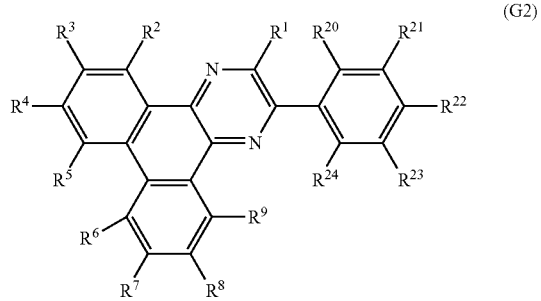

(G2)

In the above general formula (G2), $R^1$ to $R^9$ each independently represent any one of hydrogen, an alkyl group having 1 to 6 carbon atoms, and an aryl group having 6 to 13 carbon atoms. Moreover, at least one of $R^{20}$ to $R^{24}$ represents a group represented by the following general formula (G2-1) or (G2-2), and the others each independently represent any one of hydrogen, an alkyl group having 1 to 6 carbon atoms, and an aryl group having 6 to 13 carbon atoms.

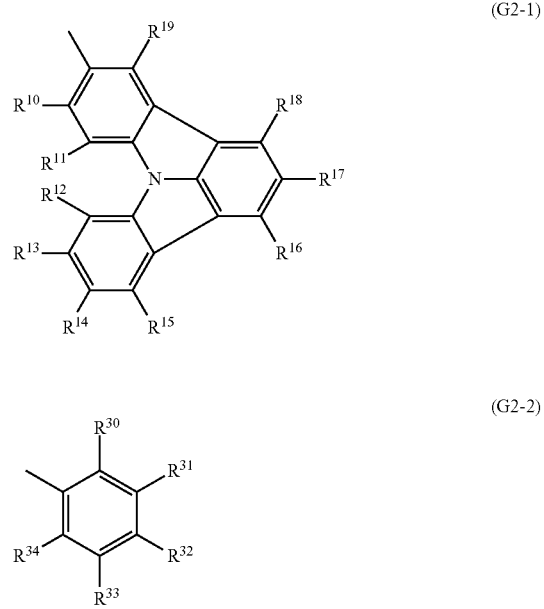

Furthermore, at least one of $R^{30}$ to $R^{34}$ in the above general formula (G2-2) represents a group represented by the above general formula (G2-1), and the others each independently represent any one of hydrogen, an alkyl group having 1 to 6 carbon atoms, and an aryl group having 6 to 13 carbon atoms. In the above general formula (G2-1), $R^{10}$ to $R^{19}$ each independently represent any one of hydrogen, an alkyl group having 1 to 6 carbon atoms, and an aryl group having 6 to 13 carbon atoms.

Another embodiment of the present invention is a heterocyclic compound represented by the following general formula (G3).

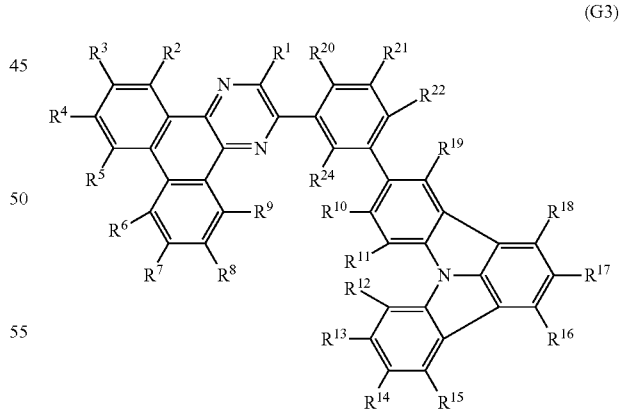

(G3)

In the above general formula (G3), $R^1$ to $R^{22}$ and $R^{24}$ each independently represent any one of hydrogen, an alkyl group having 1 to 6 carbon atoms, and an aryl group having 6 to 13 carbon atoms.

Another embodiment of the present invention is a heterocyclic compound represented by the following structural formula (101).

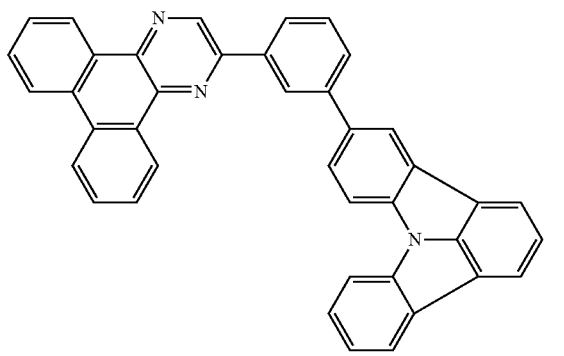

(101)

Another embodiment of the present invention is a light-emitting element which includes an EL layer containing at least a light-emitting substance between a pair of electrodes, and emits light by voltage application between the pair of electrodes. The EL layer contains a heterocyclic compound having an indolo[3,2,1-jk]carbazole skeleton and a dibenzo[f,h]quinoxaline skeleton.

Another embodiment of the present invention is a light-emitting element with the above-described structure in which the indolo[3,2,1-jk]carbazole skeleton and the dibenzo[f,h]quinoxaline skeleton of the heterocyclic compound are bonded to each other through an arylene group.

Another embodiment of the present invention is a light-emitting element with the above-described structure, in which the EL layer includes a light-emitting layer, the light-emitting layer contains at least a light-emitting substance and a first organic compound, and the first organic compound is the heterocyclic compound.

Another embodiment of the present invention is a light-emitting element with the above-described structure, in which the EL layer includes a light-emitting layer and an electron-transport layer in contact with a cathode side surface of the light-emitting layer, the light-emitting layer contains at least a light-emitting substance and the first organic compound, and a common skeleton is included in the first organic compound and an electron-transport material contained in the electron-transport layer.

Another embodiment of the present invention is a light-emitting element with the above-described structure, in which the electron-transport material is a heterocyclic compound.

Another embodiment of the present invention is a light-emitting element with the above-described structure, in which the heterocyclic compound is the heterocyclic compound described above.

Another embodiment of the present invention is a display module including the light-emitting element with any of the above structures.

Another embodiment of the present invention is a lighting module including the light-emitting element with any of the above structures.

Another embodiment of the present invention is a light-emitting device including the light-emitting element with any of the above structures and a unit for controlling the light-emitting element.

Another embodiment of the present invention is a display device including the light-emitting element with any of the above structures in a display portion, and a unit for controlling the light-emitting element.

Another embodiment of the present invention is a lighting device including the light-emitting element with any of the above structures in a lighting portion, and a unit for controlling the light-emitting element.

Another embodiment of the present invention is an electronic device including the light-emitting element with any of the above structures.

A light-emitting element in accordance with one embodiment of the present invention has high emission efficiency or a low driving voltage.

The heterocyclic compound of one embodiment of the present invention has a wide band gap. Furthermore, the heterocyclic compound has a high carrier-transport property. Accordingly, the heterocyclic compound can be suitably used in a light-emitting element, as a material of a transport layer, a host material in a light-emitting layer, or a light-emitting substance in the light-emitting layer.

Another embodiment of the present invention can provide a display module, a lighting module, a light-emitting device, a lighting device, a display device, and an electronic device each using the heterocyclic compound and achieving low power consumption.

BRIEF DESCRIPTION OF THE DRAWINGS

FIGS. 4A and 4B are conceptual diagrams of an active matrix light-emitting device.

DETAILED DESCRIPTION OF THE INVENTION

Figure 1A:
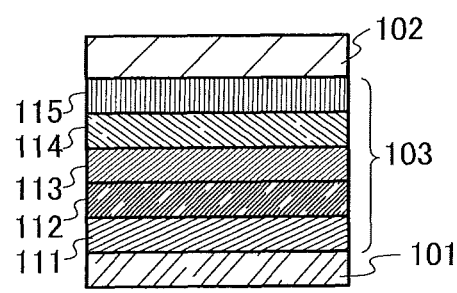
FIGS. 1A and 1B are conceptual diagrams of light-emitting elements.

Embodiments of the present invention will be described below. It is easily understood by those skilled in the art that modes and details disclosed herein can be modified in various ways without departing from the spirit and the scope of the present invention. Therefore, the present invention is not interpreted as being limited to the description of the following embodiments.

[Embodiment 1]

A heterocyclic compound of this embodiment has an indolo[3,2,1-jk]carbazole skeleton and a dibenzo[f,h]quinoxaline skeleton. The heterocyclic compound has a wide band gap and a high triplet level ($T_1$ level). Moreover, the heterocyclic compound has a high carrier-transport property.

Therefore, a light-emitting element containing the heterocyclic compound can have a high emission efficiency. In addition, a light-emitting element containing the heterocyclic compound can have a low driving voltage.

It is preferable that the indolo[3,2,1-jk]carbazole skeleton and the dibenzo[f,h]quinoxaline skeleton of the heterocyclic compound be bonded to each other through an arylene group. By the bonding between these skeletons through an arylene group, the compound can have a wide band gap and a high $T_1$ level. The arylene group preferably has 6 to 13 carbon atoms. Examples of the arylene group having 6 to 13 carbon atoms include a phenylene group, a naphthalenediyl group, a biphenyldiyl group, and a fluorenediyl group, in particular, a phenylene group, a biphenyldiyl group, and a fluorenediyl group are preferable to give a high $T_1$ level.

Note that each of these arylene groups may have a substituent, and the substituent can be an alkyl group having 1 to 6 carbon atoms, an aryl group having 6 to 12 carbon atoms, or the like.

It is preferable that the indolo[3,2,1-jk]carbazole skeleton and the dibenzo[f,h]quinoxaline skeleton be bonded by the arylene group not linearly to each other but bonded to each other so as to form a folded structure. This is because an interaction between π-orbits of the two skeletons can be reduced, the band gap width can be increased, and the $T_1$ level can be increased. For example, when the arylene group is a phenylene group, a meta-phenylene group is preferred to a para-phenylene group. When the arylene group is a biphenyldiyl group, a 1,1'-biphenyl-3,3'-diyl group is preferable.

Since the heterocyclic compound with such a structure has a wide band gap, in a light-emitting layer of a light-emitting element, the heterocyclic compound can be suitably used as a host material for a fluorescent material that emits blue light or light having a shorter wavelength than blue light, or can be preferably used for a carrier-transport layer that is adjacent to the light-emitting layer. Since the heterocyclic compound also has a high $T_1$ level, the heterocyclic compound can be suitably used as a host material for a phosphorescent material in the light-emitting layer, or can be preferably used for a carrier-transport layer that is adjacent to the light-emitting layer. The heterocyclic compound has a wide band gap or a high level, so that the energy of carriers that recombine at a host material can be effectively transferred to a light-emitting substance. Thus, a light-emitting element having a high emission efficiency can be manufactured.

The heterocyclic compound can be suitably used as a host material or for a carrier-transport layer in a light-emitting element due to its high carrier-transport property. Hence, a light-emitting element with a low driving voltage can be manufactured. Furthermore, in the case where the heterocyclic compound is used for a carrier-transport layer closer to a light-emitting region in a light-emitting layer, loss of excitation energy of a light-emitting substance can be suppressed because of a wide band gap or a high $T_1$ level of the heterocyclic compound, so that a light-emitting element having a high emission efficiency can be achieved.

The heterocyclic compound having the above indolo[3,2,1-jk]carbazole skeleton and dibenzo[f,h]quinoxaline skeleton can also be represented by the following general formula (G0).

$$A^1\text{-Ar-}A^2 \tag{G0}$$

In the above general formula (G0), $A^1$ represents a dibenzo[f,h]quinoxalinyl group, $A^2$ represents an indolo[3,2,1-jk]carbazolyl group, and Ar represents an arylene group having 6 to 13 carbon atoms. The dibenzo[f,h]quinoxalinyl group, the indolo[3,2,1-jk]carbazolyl group, and the arylene group each may be independently unsubstituted or have a substituent selected from an alkyl group having 1 to 6 carbon atoms and an aryl group having 6 to 13 carbon atoms.

Note that throughout this specification, examples of an alkyl group having 1 to 6 carbon atoms include a methyl group, an ethyl group, an n-propyl group, an iso-propyl group, an n-butyl group, an iso-butyl group, a sec-butyl group, a tert-butyl group, a pentyl group, a hexyl group, and a cyclohexyl group. Examples of the aryl group having 6 to 13 carbon atoms include a phenyl group, a biphenyl group, a fluorenyl group, and a naphthyl group. The aryl group having 6 to 13 carbon atoms may have a substituent, and an alkyl group having 1 to 6 carbon atoms and a phenyl group can be given as examples of the substituent. Note that such substituents may be bonded to each other and form a ring. As an example of such a case, a spirofluorene skeleton is formed in such a manner that a carbon atom at the 9-position of a fluorenyl group has two phenyl groups as substituents and these phenyl groups are bonded to each other.

Throughout this specification, specific examples of the arylene group having 6 to 13 carbon atoms are a phenylene group, a biphenyldiyl group, a naphthalenediyl group, and a fluorenediyl group. Among these examples, a phenylene group or a biphenyldiyl group is preferable, and a phenylene group is further preferable.

It is preferable that the indolo[3,2,1-jk]carbazole skeleton and the dibenzo[f,h]quinoxaline skeleton be bonded by Ar not linearly to each other but bonded to each other so as to form a folded structure. This is because an interaction between π-orbits of the two skeletons can be decreased, the band gap width can be increased, and the $T_1$ level can be increased. For example, when Ar is a phenylene group, a meta-phenylene group is preferred to a para-phenylene group. When Ar is a biphenyldiyl group, a 1,1'-biphenyl-3,3'-diyl group is preferable.

Note that Ar may have a substituent, and the substituent can be an alkyl group having 1 to 6 carbon atoms or an aryl group having 6 to 13 carbon atoms. Such substituents may be bonded to each other to form a ring.

The heterocyclic compound of this embodiment can also be represented by the following general formula (G1).

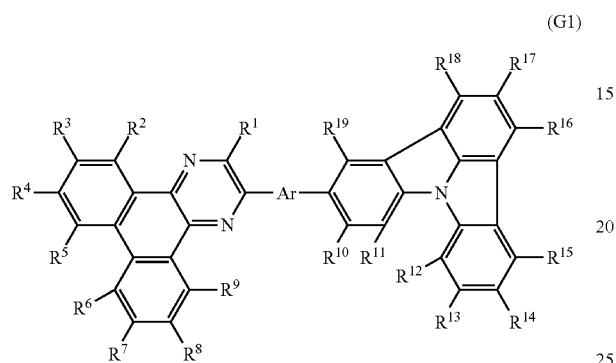

(G1)

In the general formula (G1), $R^1$ to $R^{19}$ each independently represent any one of hydrogen, an alkyl group having 1 to 6 carbon atoms, and an aryl group having 1 to 13 carbon atoms.

In the above formula, Ar represents an arylene group having 6 to 13 carbon atoms.

Similarly to the case of the general formula (G0), it is preferable that the indolo[3,2,1-jk]carbazole skeleton and the dibenzo[f,h]quinoxaline skeleton in the general formula (G1) be bonded by Ar not linearly to each other but bonded to each other so as to form a folded structure. For example, when Ar is a phenylene group, a meta-phenylene group is preferred to a para-phenylene group. When Ar is a biphenyldiyl group, a 1,r-biphenyl-3,3'-diyl group is preferable.

Note that Ar may have a substituent, and the substituent can be an alkyl group having 1 to 6 carbon atoms or an aryl group having 6 to 13 carbon atoms.

Such a heterocyclic compound can be represented by the following general formula (G2). The heterocyclic compound represented by the following general formula (G2) is a preferred example of the heterocyclic compound represented by the above general formula (G1).

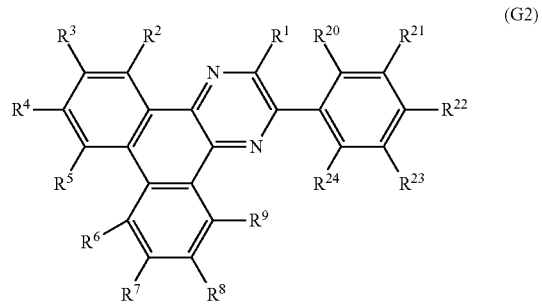

(G2)

In the above general formula (G2), $R^1$ to $R^9$ each independently represent any one of hydrogen, an alkyl group having 1 to 6 carbon atoms, and an aryl group having 6 to 13 carbon atoms.

Moreover, in the above formula, one of $R^{20}$ to $R^{24}$ represents a group represented by the following general formula (G2-1) or (G2-2), and the others each independently represent any one of hydrogen, an alkyl group having 1 to 6 carbon atoms, and an aryl group having 6 to 13 carbon atoms.

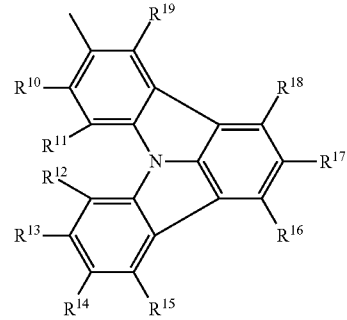

(G2-1)

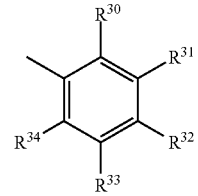

(G2-2)

In the above general formula (G2-2), one of $R^{30}$ to $R^{34}$ represents a group represented by the above general formula (G2-1), and the others each independently represent any one of hydrogen, an alkyl group having 1 to 6 carbon atoms, and an aryl group having 6 to 13 carbon atoms.

In the above general formula (G2-1), $R^{10}$ to $R^{19}$ each independently represent any one of hydrogen, an alkyl group having 1 to 6 carbon atoms, and an aryl group having 6 to 13 carbon atoms.

In the heterocyclic compound represented by the above general formula (G1) or (G2), the indolo[3,2,1-jk]carbazole skeleton and the dibenzo[f,h]quinoxaline skeleton are preferably bonded through a meta-phenylene group, and such a heterocyclic compound can be represented by the following general formula (G3).

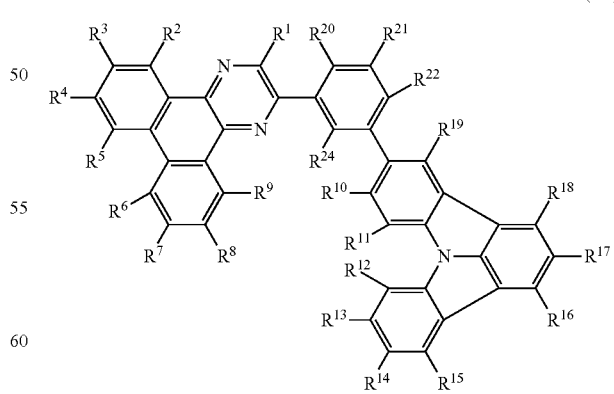

(G3)

In the above general formula (G3), $R^1$ to $R^{22}$ and $R^{24}$ each independently represent any one of hydrogen, an alkyl group having 1 to 6 carbon atoms, and an aryl group having 6 to 13 carbon atoms.

Note that each of $R^1$ to $R^{22}$ and $R^{24}$ is preferably hydrogen, because synthesis can be carried out at low cost due to the easiness in synthesis and availability of a raw material.
Specific examples of structures of the heterocyclic compounds represented by the above general formulae (G1) to (G3) are represented by the following structural formulae (100) to (160).
(100)
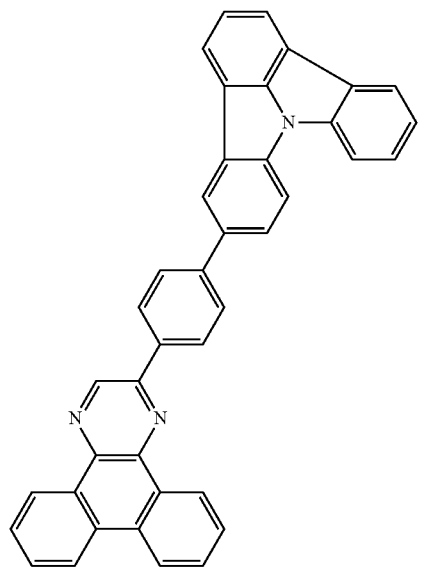
(101)
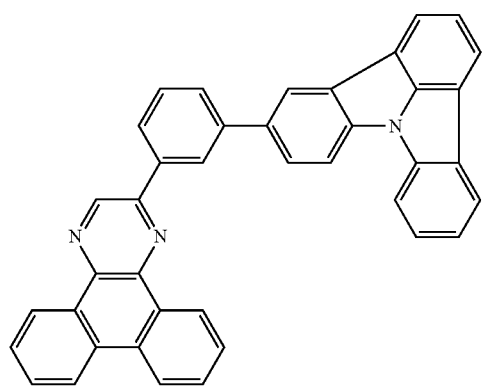
(102)
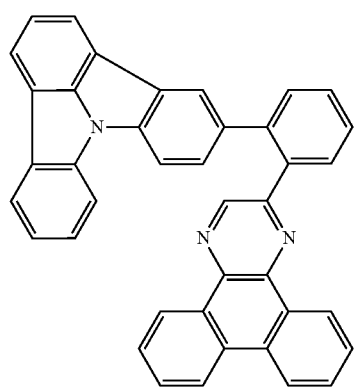
(103)
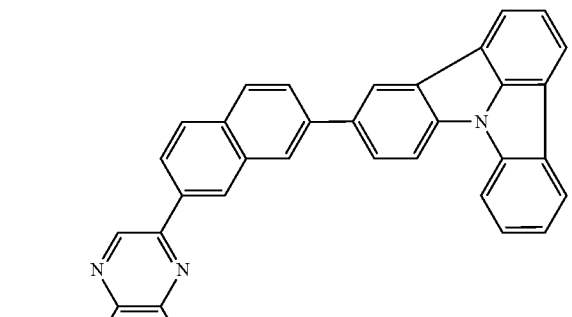
(104)
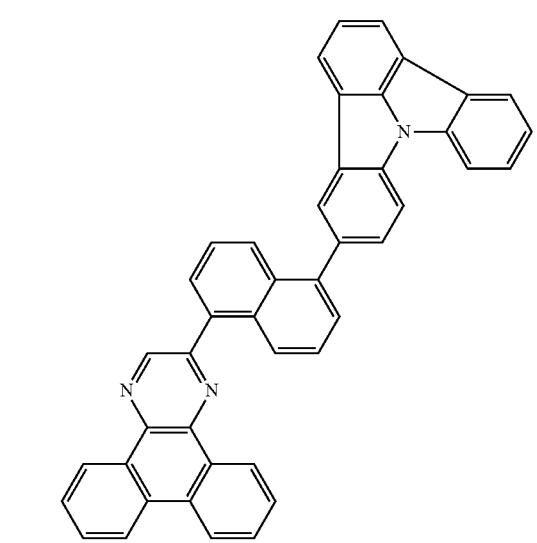
(105)
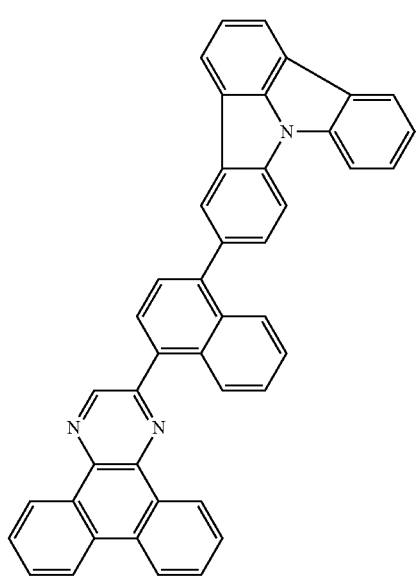

(106)
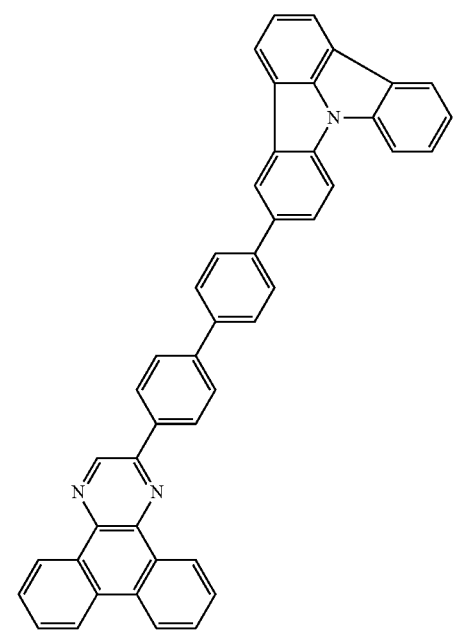
(107)
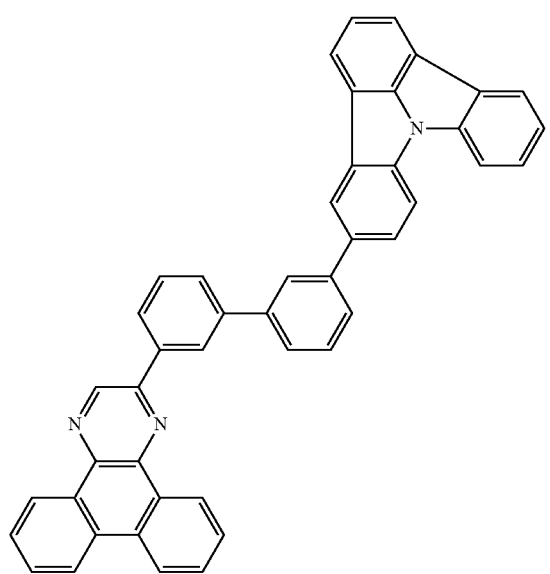
(109)
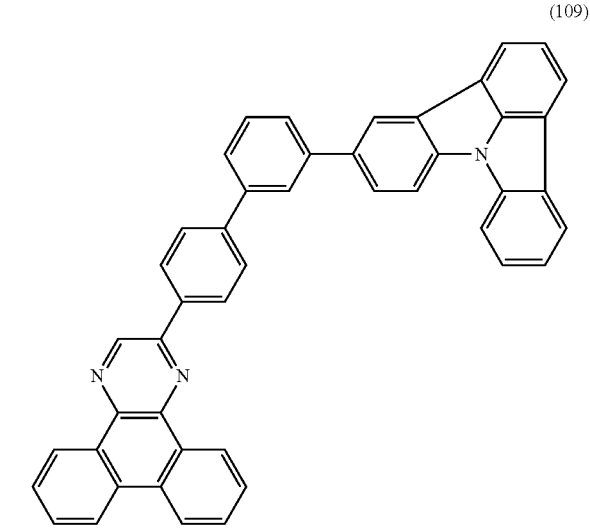
(110)
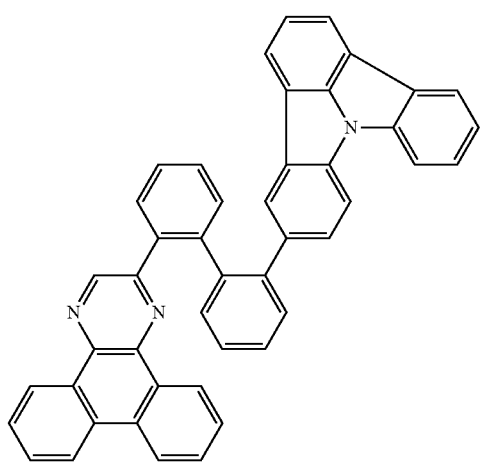
(111)
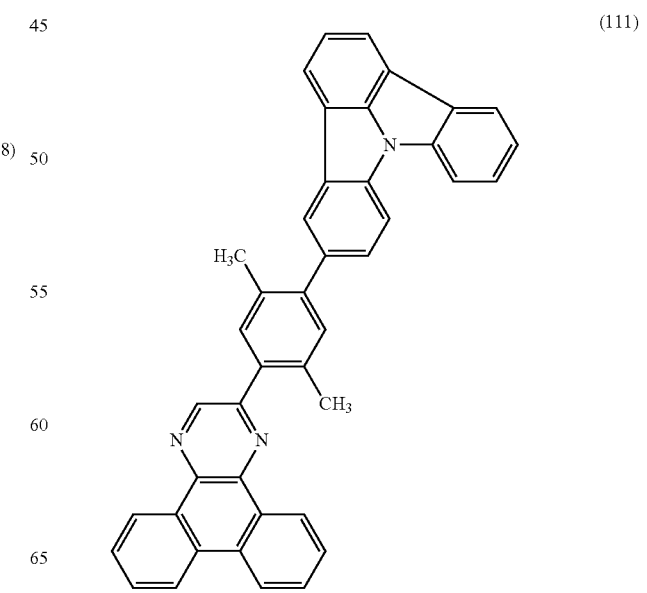
(108)

(112)
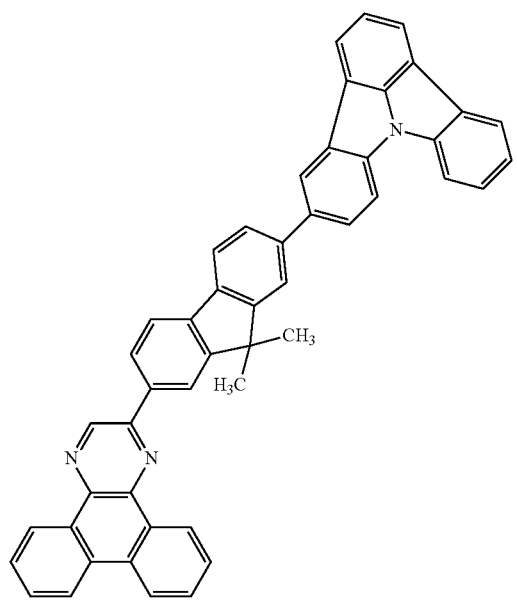
(114)
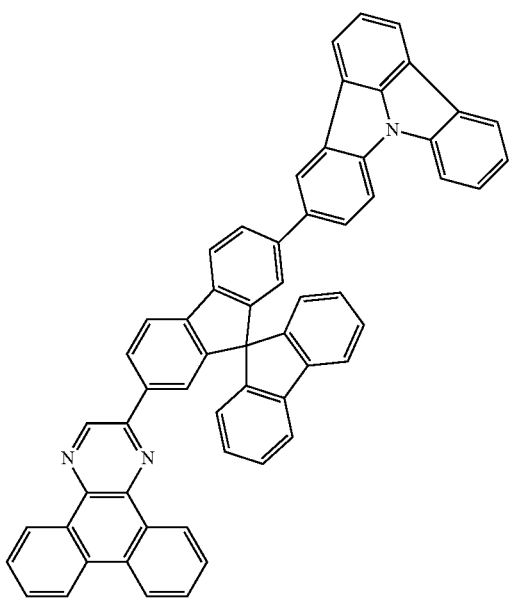
(113)
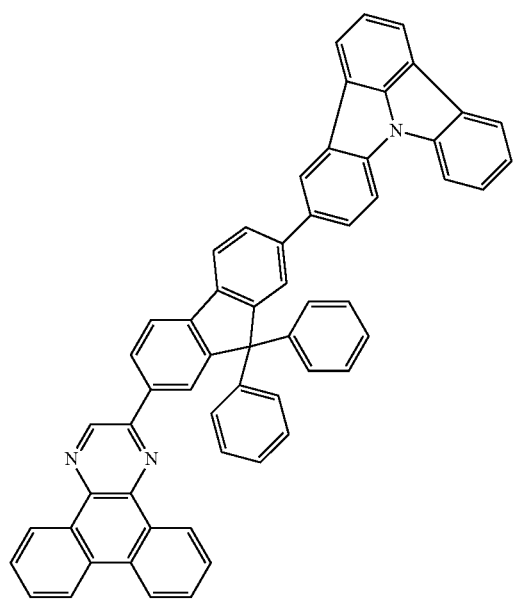
(115)
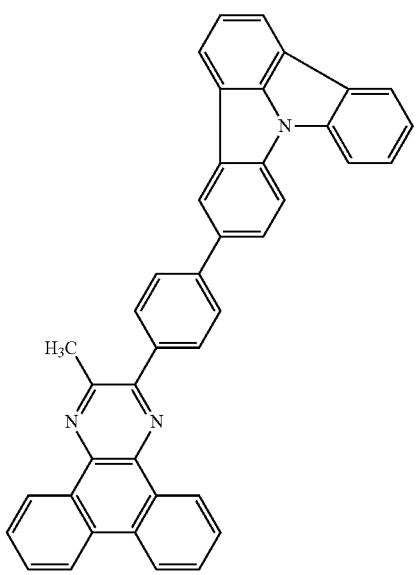

(116) 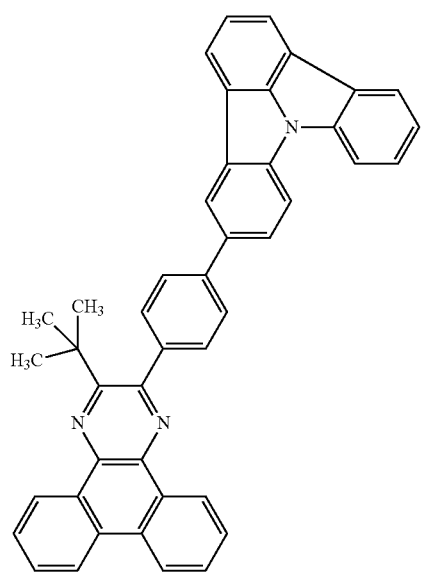
(117) 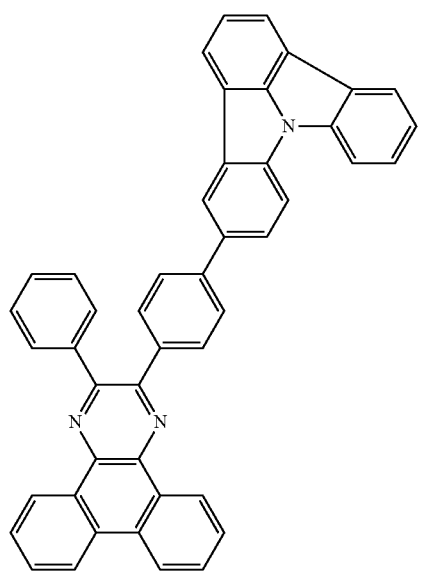
(118) 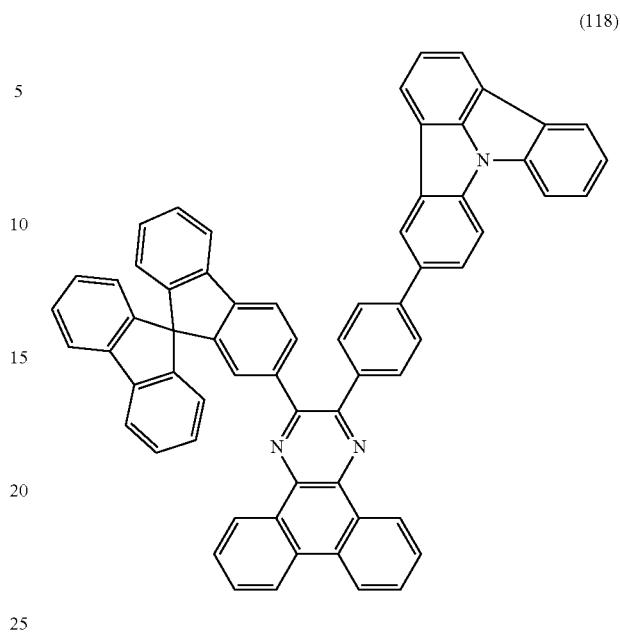
(119) 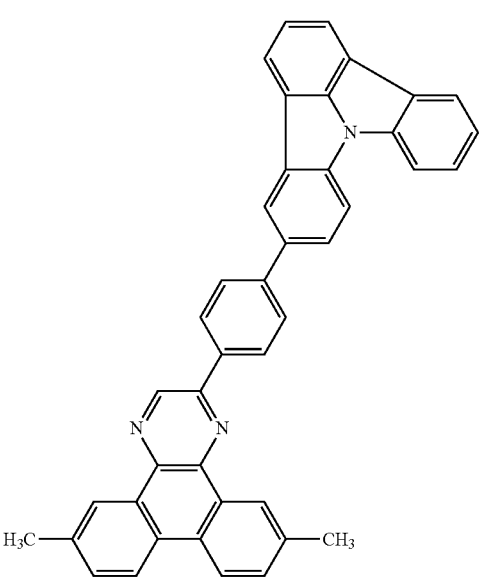

(120)
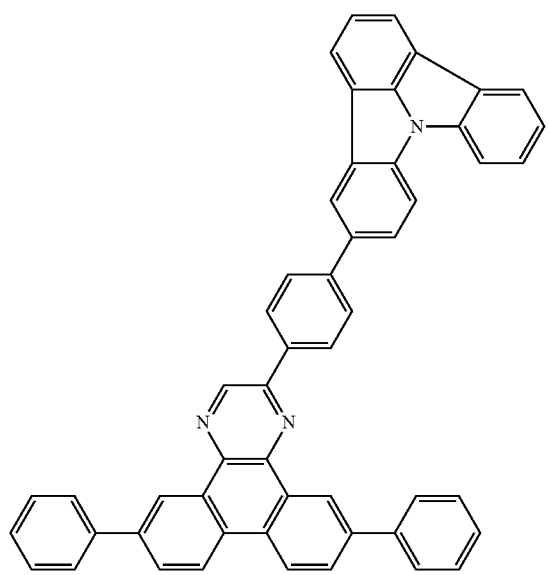
(122)
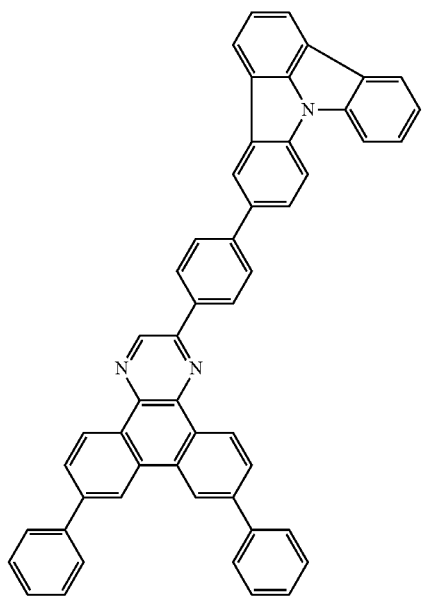
(121)
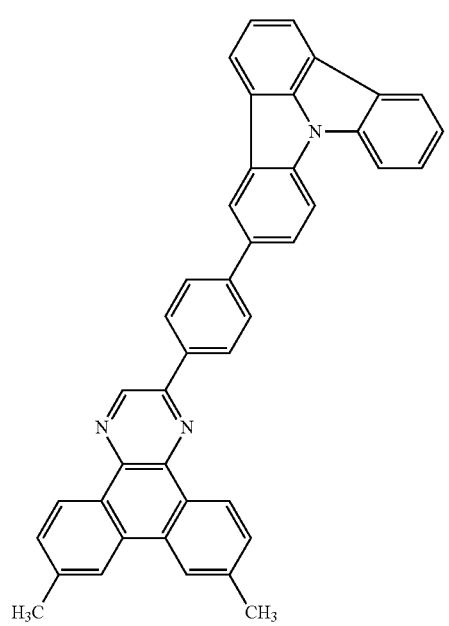
(123)
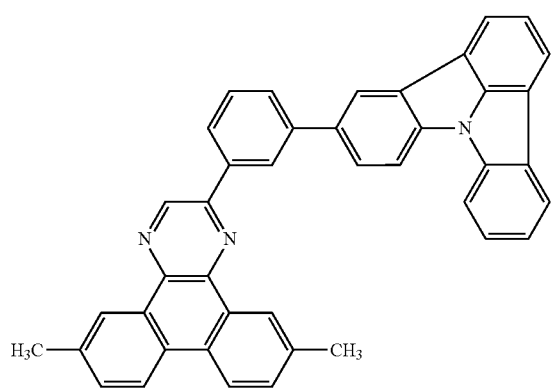
(124)
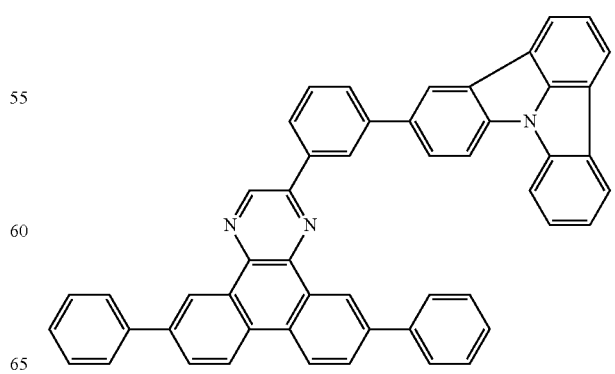

(125)
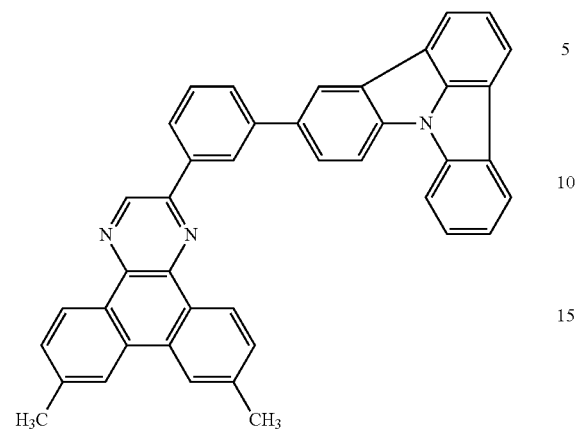
(126)
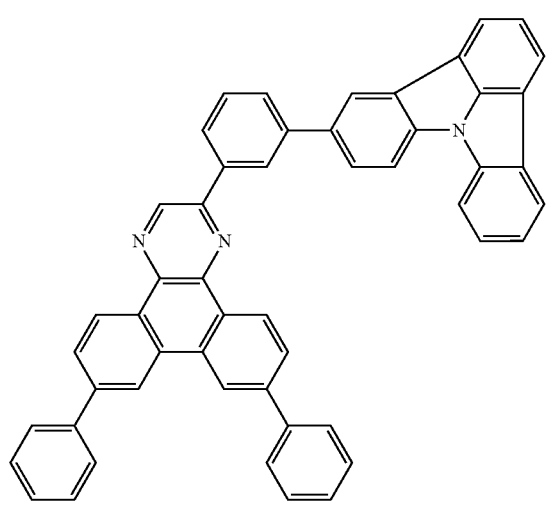
(127)
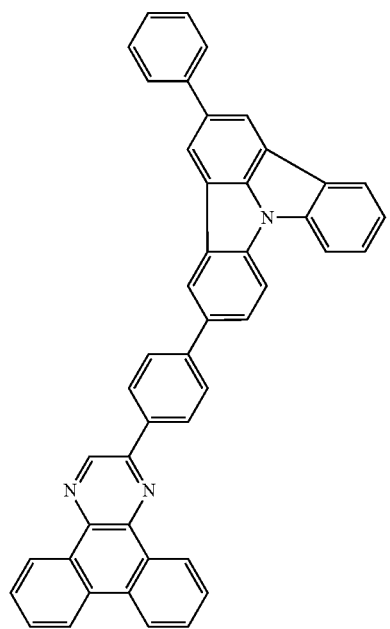
(128)
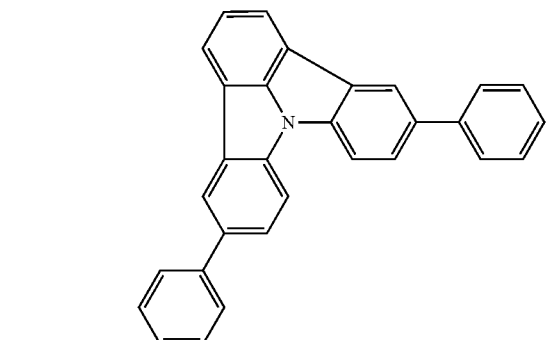
(129)
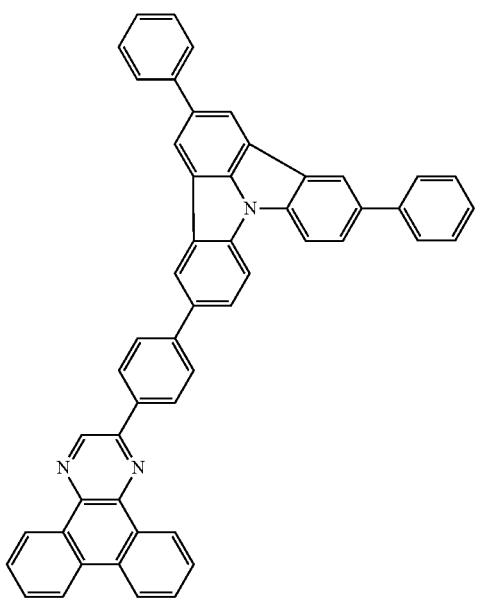

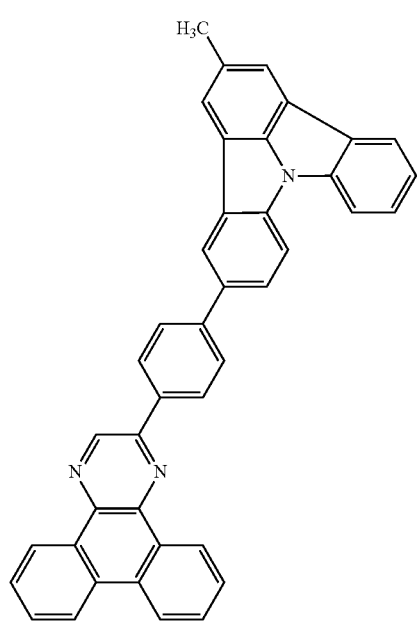
(130)
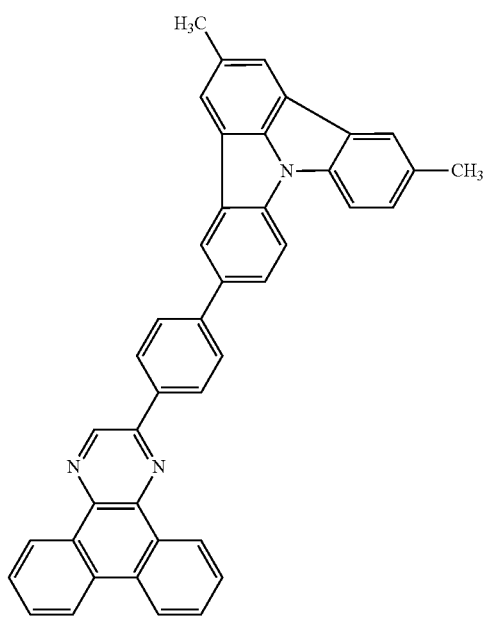
(132)
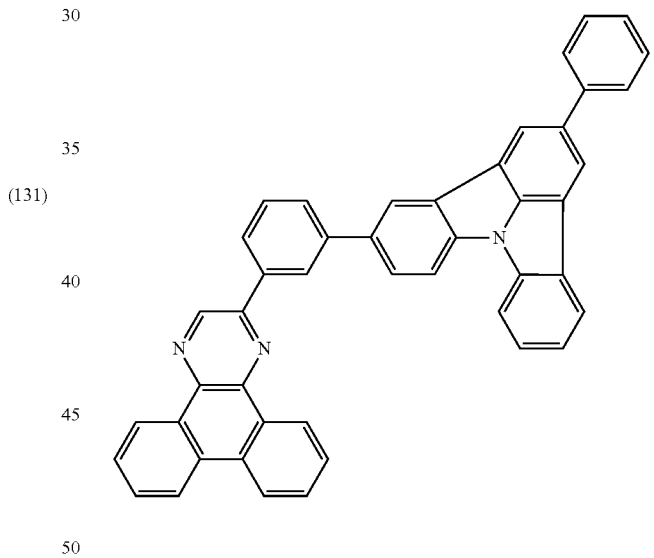
(133)
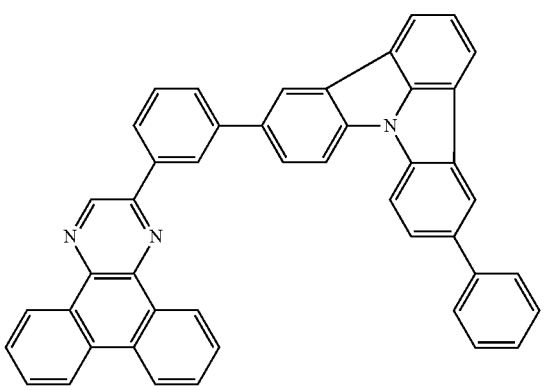
(134)
(131)

(135)
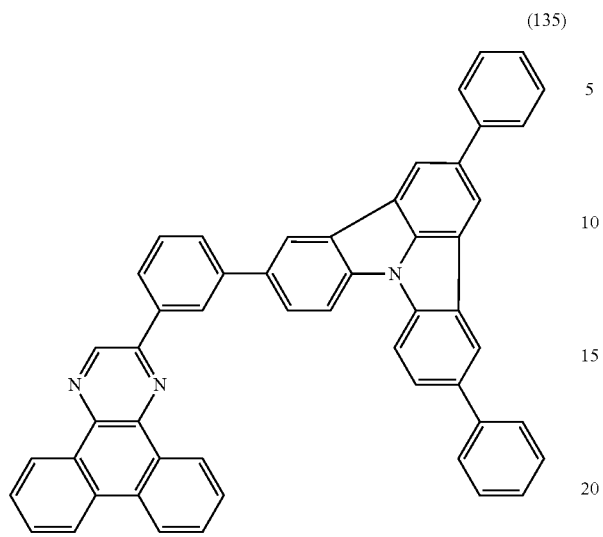
(136)
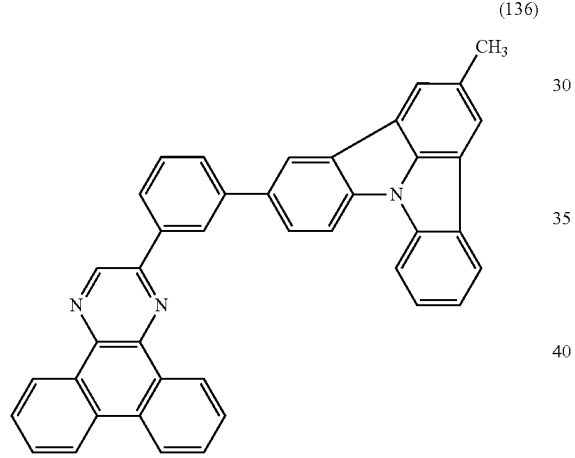
(137)
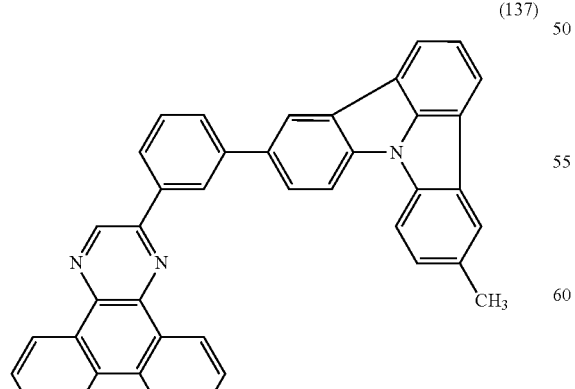
(138)
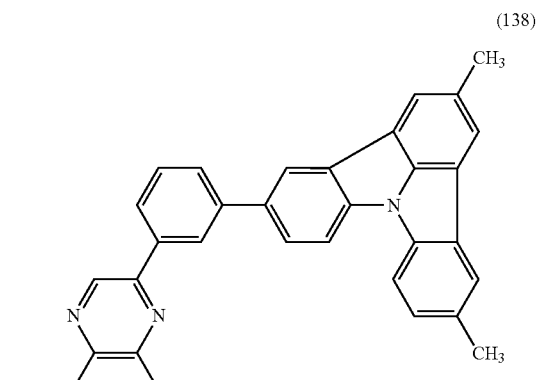
(139)
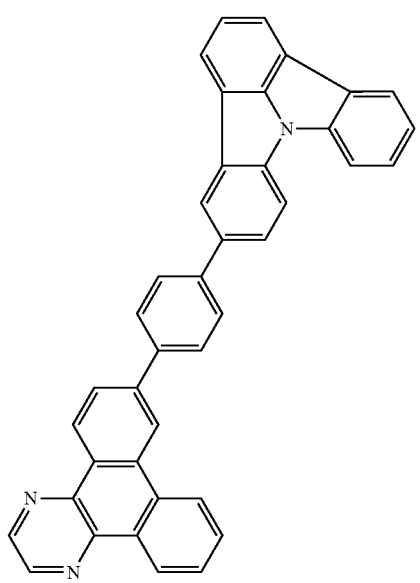
(140)
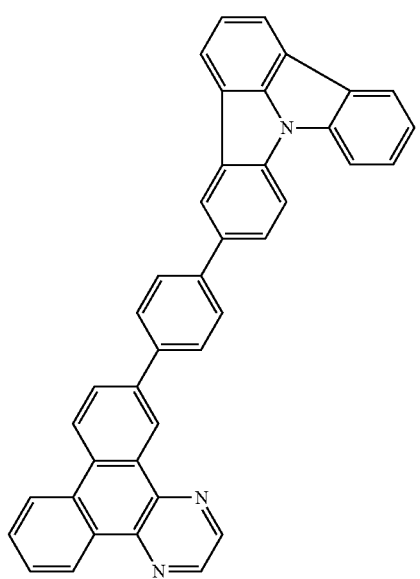

(141)
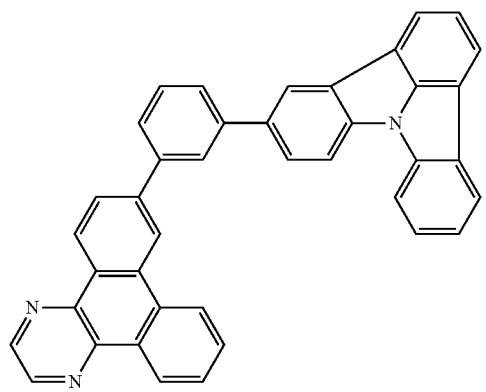
(142)
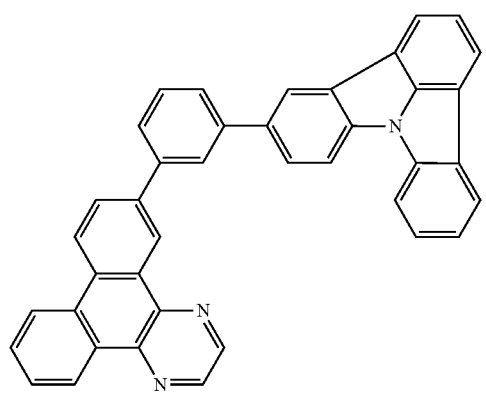
(143)
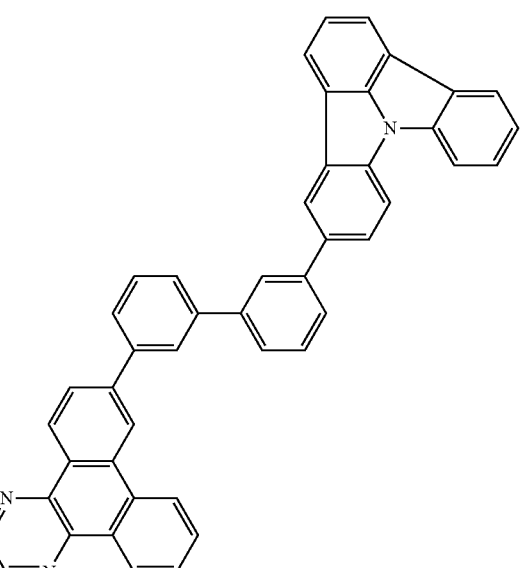
(144)
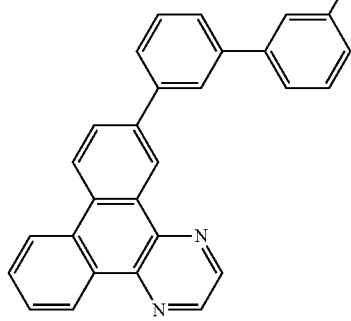
(145)
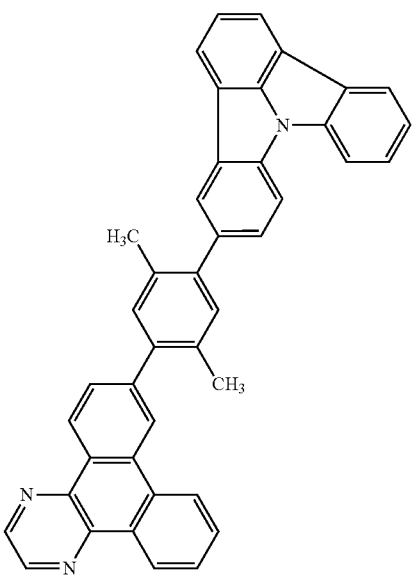

(146)
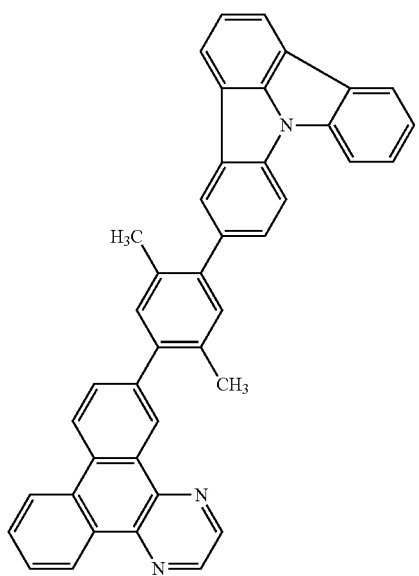
(148)
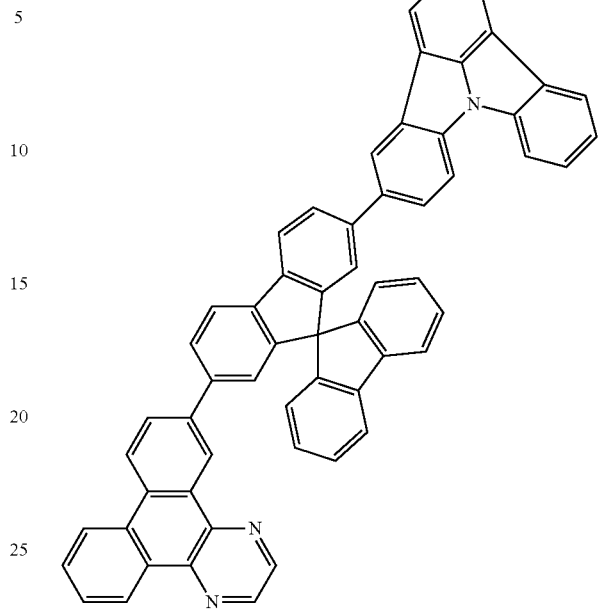
(147)
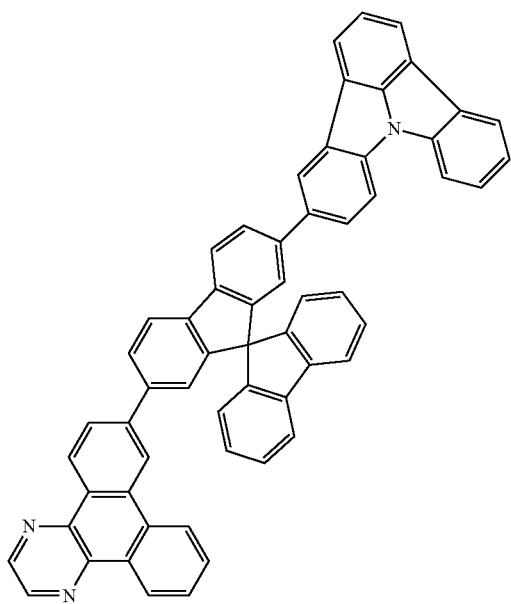
(149)
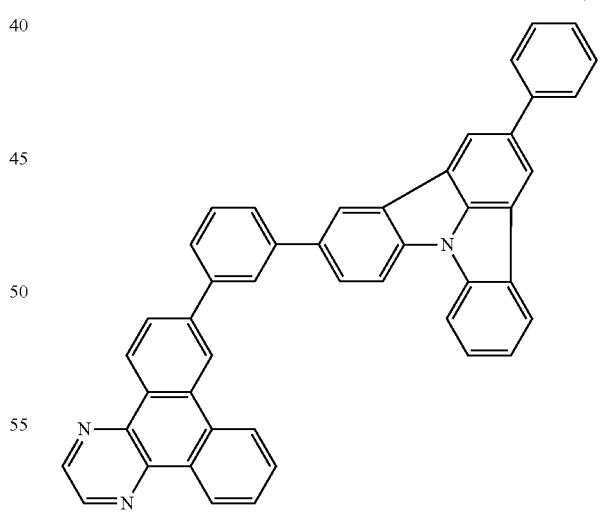

(150)
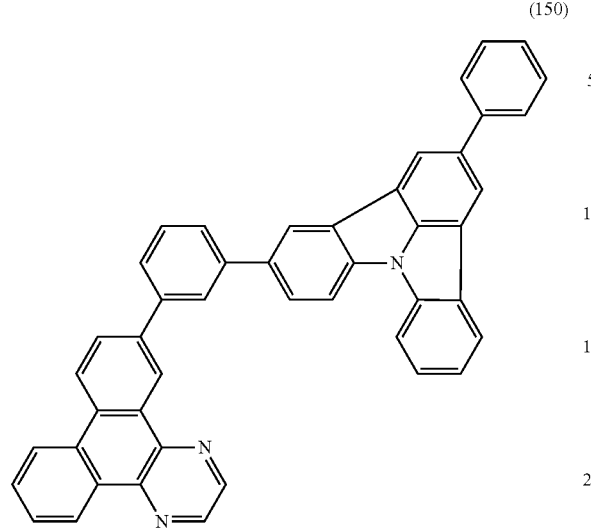
(151)
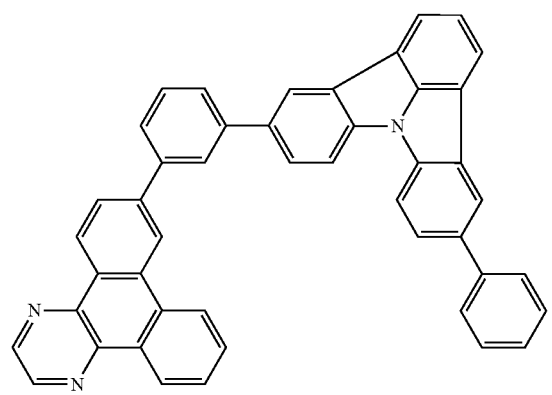
(152)
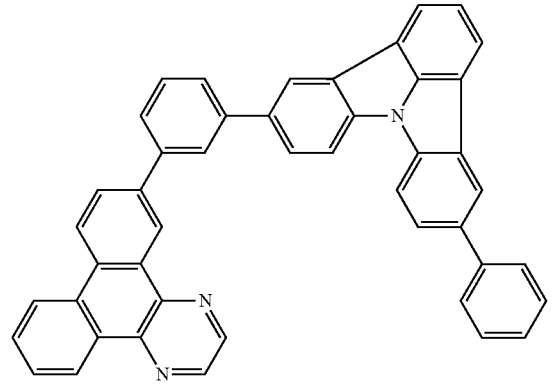
(153)
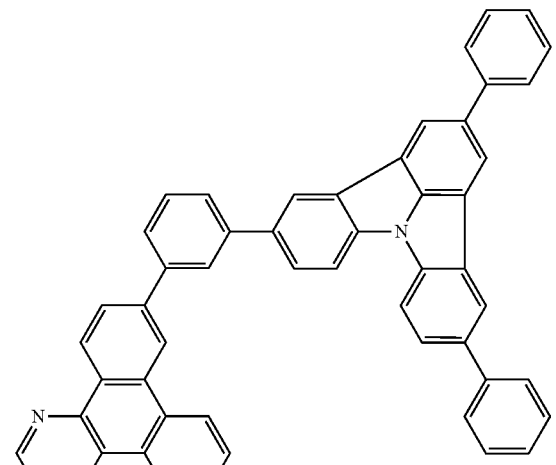
(154)
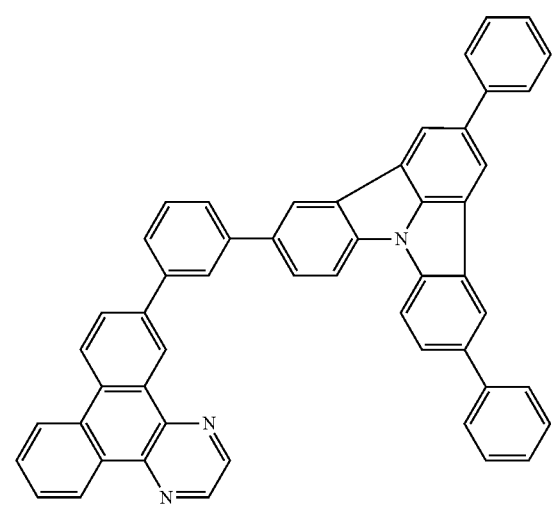
(155)
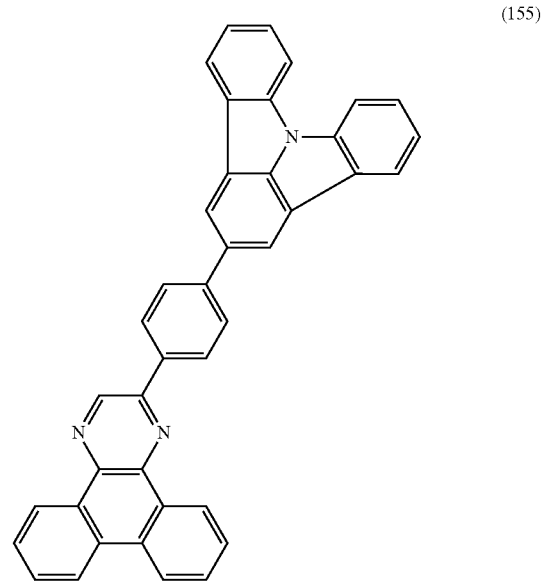

(156)
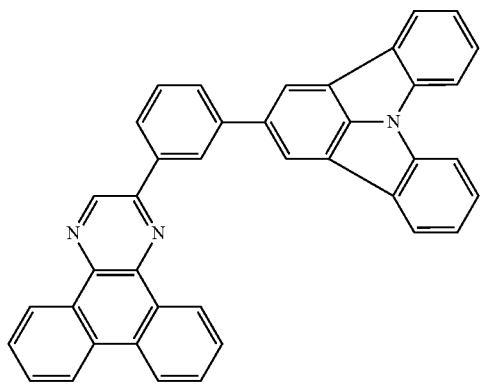

(159)
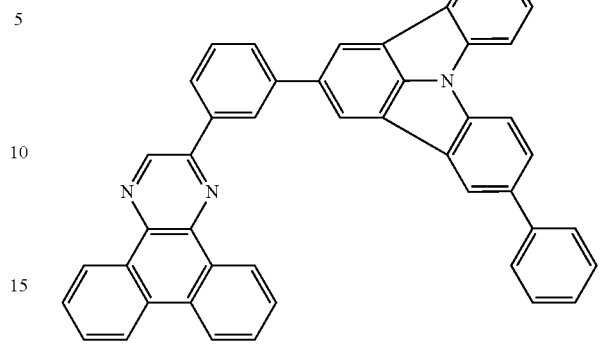

(157)
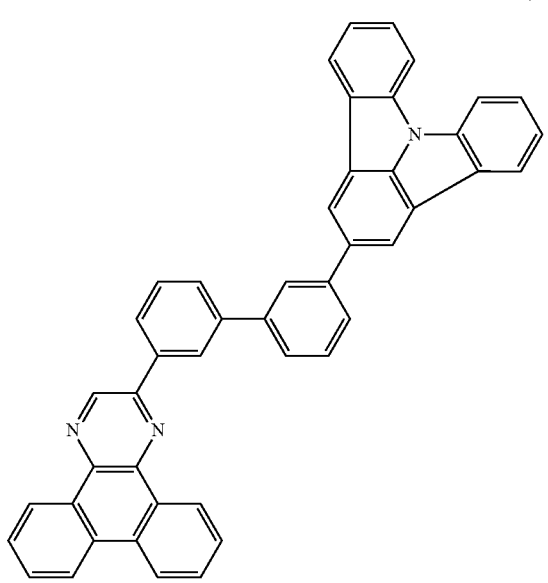

(160)
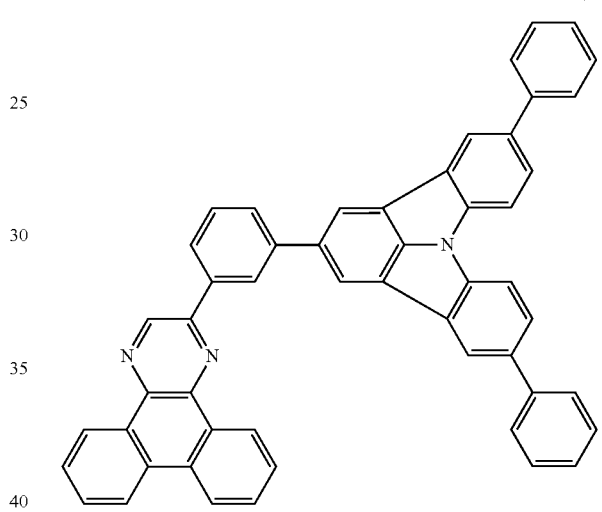

(158)
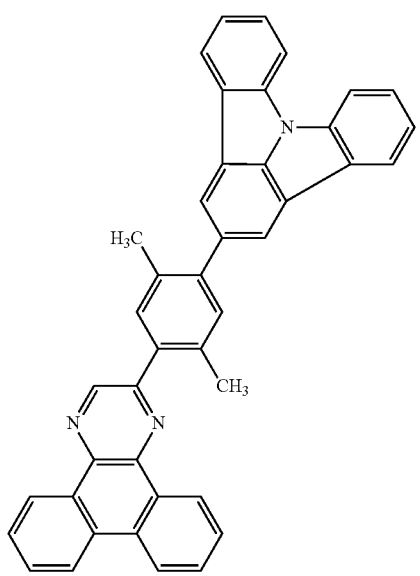

Any of the above heterocyclic compounds is suitable as a carrier-transport material or a host material because of its high carrier-transport property. Hence, a light-emitting element with a low driving voltage can also be provided. Furthermore, a phosphorescent light-emitting element having a high emission efficiency can be obtained because of the high $T_1$ level of the heterocyclic compounds. Moreover, the high $T_1$ level means that the heterocyclic compounds have a wide band gap, which allows a blue-emissive fluorescent light-emitting element to efficiently emit light.

Furthermore, the heterocyclic compound of this embodiment can be used as a light-emitting material that emits blue to ultraviolet light.

Subsequently, a method of synthesizing these heterocyclic compounds is described. As shown in the following synthesis scheme (A-1), a halide of a dibenzo[f,h]quinoxaline derivative or a dibenzo[f,h]quinoxaline derivative that has a triflate group as a substituent (compound 1) may be coupled with an organoboron compound or a boronic acid (compound 2) of an indolo[3,2,1-jk]carbazole derivative by the Suzuki-Miyaura reaction, whereby an objective compound represented by the above structural formula (G1) can be provided.

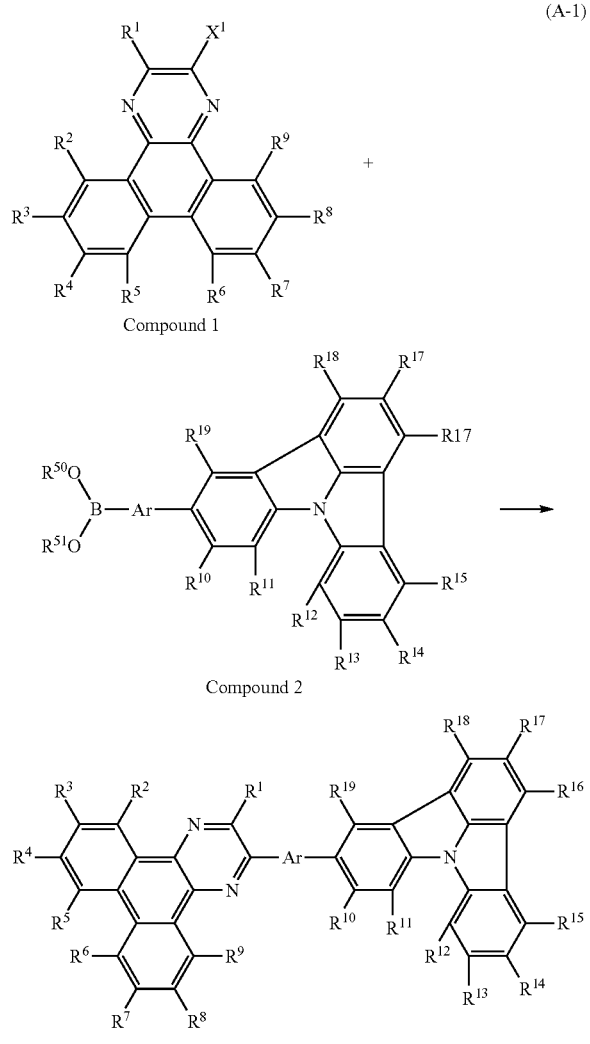

Compound 1

Compound 2

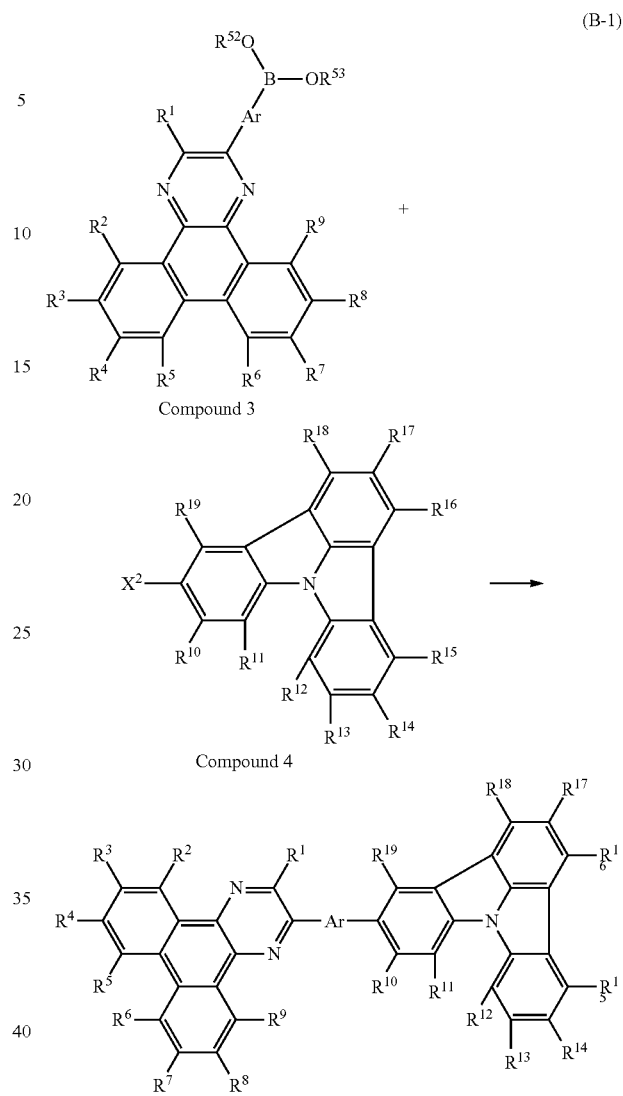

Compound 3

Compound 4

In the above synthesis scheme (A-1), $R^1$ to $R^{19}$ each independently represent hydrogen, an alkyl group having 1 to 6 carbon atoms, or a substituted or unsubstituted aryl group having 6 to 13 carbon atoms, and Ar represents a substituted or unsubstituted arylene group having 6 to 13 carbon atoms. $R^{50o}$ and $R^{51}$ each independently represent either hydrogen or an alkyl group having 1 to 6 carbon atoms, and $R^{50o}$ and $R^{51}$ may be bonded to each other to form a ring. $X^1$ represents either a halogen or a triflate group.

Furthermore, in the Suzuki-Miyaura coupling reaction shown in the synthesis scheme (A-1), an organoboron compound or a boronic acid of a dibenzo[f,h]quinoxaline derivative may be coupled with a halide of an indolo[3,2,1-jk]carbazole derivative or an indolo[3,2,1-jk]carbazole derivative that has a triflate group as a substituent by the Suzuki-Miyaura reaction.

As in the following synthesis scheme (B-1), an organoboron compound or a boronic acid (compound 3) of a dibenzo[f,h]quinoxaline derivative may be coupled with a halide of an indolo[3,2,1-jk]carbazole derivative or an indolo[3,2,1-jk]carbazole derivative that has a triflate group as a substituent (compound 4) by the Suzuki-Miyaura reaction, whereby the above heterocyclic compounds are synthesized.

In the above synthesis scheme (B-1), $R^1$ to $R^{19}$ each independently represent hydrogen, an alkyl group having 1 to 6 carbon atoms, or a substituted or unsubstituted aryl group having 6 to 13 carbon atoms. In addition, Ar represents a substituted or unsubstituted arylene group having 6 to 13 carbon atoms. Moreover, $R^{52}$ and $R^{53}$ each independently represent either hydrogen or an alkyl group having 1 to 6 carbon atoms, and $R^{52}$ and $R^{53}$ may be bonded to each other and form a ring. Furthermore, $X^2$ represents either a halogen or a triflate group.

The Suzuki-Miyaura reaction shown in the synthesis schemes (A-1) and (B-1) may be replaced with a cross coupling reaction using an organoaluminum compound, an organozirconium compound, an organozinc compound, an organotin compound, or the like as well as the organoboron compound or boronic acid represented by the compounds 2 and 3. However, the present invention is not limited thereto.

Furthermore, in the Suzuki-Miyaura coupling reaction shown in the synthesis scheme (B-1), an organoboron compound or a boronic acid of an indolo[3,2,1-jk]carbazole derivative may be coupled with a halide of dibenzo[f,h]quinoxaline derivative or a dibenzo[f,h]quinoxaline derivative that has a triflate group as a substituent by the Suzuki-Miyaura reaction.

Examples of a palladium complex that is used in the synthesis scheme (A-1) or (B-1) include palladium(II) acetate, tetrakis(triphenylphosphine)palladium(0), and bis(triphenylphosphine)palladium(II) dichloride, and another palladium catalyst may be used. Examples of a ligand of the palladium complex include tri(ortho-tolyl)phosphine, triphenylphosphine, and tricyclohexylphosphine, and another ligand may also be used. Examples of a base that is used in the synthesis scheme (A-1) or (B-1) include an organic base such as sodium tert-butoxide and an inorganic base such as potassium carbonate or sodium carbonate, and another base may also be used. Examples of solvents that is used in the synthesis scheme (A-1) or (B-1) include, but are not limited to, a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; and a mixed solvent of an ether such as ethylene glycol dimethyl ether and water. Note that a mixed solvent of toluene and water; a mixed solvent of toluene, ethanol, and water; or a mixed solvent of an ether such as ethylene glycol dimethyl ether and water is further preferable.

As described above, the heterocyclic compound of this embodiment can be synthesized.

[Embodiment 2]

In this embodiment, an example will be described in which the heterocyclic compound represented by the following general formula (G1) described in Embodiment 1 is used for an active layer of a vertical transistor (SIT), which is a kind of an organic semiconductor element. In the following general formula (G1), $R^1$ to $R^{19}$ each independently represent any one of hydrogen, an alkyl group having 1 to 6 carbon atoms, and an aryl group having 6 to 13 carbon atoms, and Ar represents an arylene group having 6 to 13 carbon atoms.

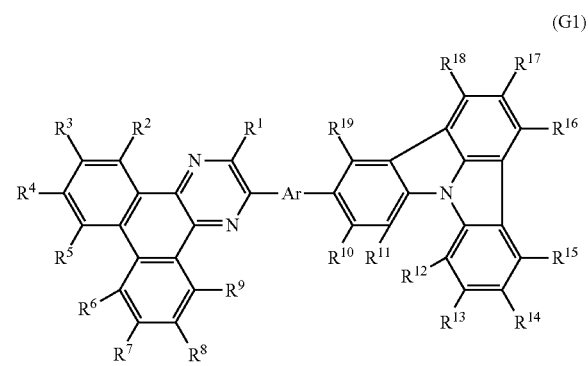

(G1)

Figure 2:
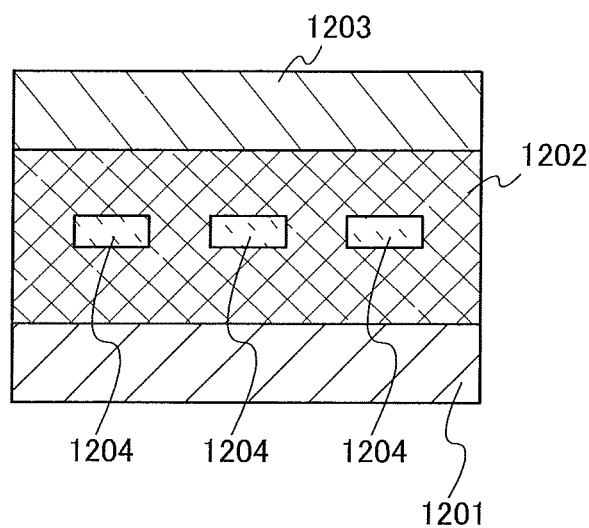
FIG. 2 is a conceptual diagram of an organic semiconductor element.

The element has a structure in which a thin-film active layer 1202 containing the heterocyclic compound represented by the general formula (G1) is interposed between a source electrode 1201 and a drain electrode 1203, and a gate electrode 1204 is embedded in the active layer 1202, as illustrated in FIG. 2. The gate electrode 1204 is electrically connected to a unit to apply a gate voltage, and the source electrode 1201 and the drain electrode 1203 are electrically connected to a unit to control the voltage between a source and a drain.

In such an element structure, when a voltage is applied between the source and the drain under the condition that a gate voltage is not applied, a current flows (an ON state). Then, when a gate voltage is applied in this state, a depletion layer is generated in the periphery of the gate electrode 1204, and thus a current does not flow (an OFF state). With such a mechanism, the element operates as a transistor.

In a vertical transistor, a material which has both a carrier-transport property and favorable film quality are required for an active layer like in a light-emitting element. Any of the heterocyclic compounds represented by the general formula (G1) can be suitably used because it sufficiently meets these requirements.

[Embodiment 3]

In this embodiment, one mode of a light-emitting element that contains a heterocyclic compound of one embodiment of the present invention will be described with reference to FIG. 1A.

The light-emitting element of this embodiment has a plurality of layers between a pair of electrodes. In this embodiment, the light-emitting element includes a first electrode 101, a second electrode 102, and an EL layer 103 provided between the first electrode 101 and the second electrode 102. Note that in FIG. 1A, the first electrode 101 functions as an anode and the second electrode 102 functions as a cathode. In other words, when a voltage is applied between the first electrode 101 and the second electrode 102 such that the potential of the first electrode 101 is higher than that of the second electrode 102, light emission can be obtained. Of course, a structure in which the first electrode functions as a cathode and the second electrode functions as an anode can be employed. Note that in the light-emitting element of this embodiment, any layer in the EL layer 103 may contain the heterocyclic compound of one embodiment of the present invention. Note that a layer that contains the heterocyclic compound of one embodiment of the present invention is preferably a light-emitting layer or an electron-transport layer because characteristics of the heterocyclic compound can be utilized and a light-emitting element having favorable characteristics can be obtained.

For the electrode functioning as an anode, any of metals, alloys, electrically conductive compounds, and mixtures thereof which have a high work function (specifically, a work function of 4.0 eV or more) or the like is preferably used. Specifically, for example, indium oxide-tin oxide (ITO: indium tin oxide), indium oxide-tin oxide containing silicon or silicon oxide, indium oxide-zinc oxide, and indium oxide containing tungsten oxide and zinc oxide (IWZO) can be given. Films of these electrically conductive metal oxides are usually formed by a sputtering method but may be formed by application of a sol-gel method or the like. For example, a film of indium oxide-zinc oxide can be formed by a sputtering method using a target obtained by adding 1 wt % to 20 wt % of zinc oxide to indium oxide. Further, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Besides, gold (Au), platinum (Pt), nickel (Ni), tungsten (W), chromium (Cr), molybdenum (Mo), iron (Fe), cobalt (Co), copper (Cu), palladium (Pd), nitrides of metal materials (e.g., titanium nitride), and the like can be given. In addition, graphene may be used.

There is no particular limitation on a stacked-layer structure of the EL layer 103. The EL layer 103 can be formed by combining as appropriate a layer that contains a substance having a high electron-transport property, a layer that contains a substance having a high hole-transport property, a layer that contains a substance having a high electron-injection property, a layer that contains a substance having a high hole-injection property, a layer that contains a bipolar substance (a substance having a high electron-transport and hole-transport property), a layer having a carrier-blocking property, and the like. In this embodiment, the EL layer 103 has a structure in which a hole-injection layer 111, a hole-transport layer 112, a light-emitting layer 113, an electron-transport layer 114, and an electron-injection layer 115 are stacked in this order from the side of the electrode functioning as an anode. Materials included in the layers are specifically given below.

The hole-injection layer 111 is a layer containing a substance having a hole-injection property. Molybdenum oxide, vanadium oxide, ruthenium oxide, tungsten oxide, manganese oxide, or the like can be used. Alternatively, the hole-injection layer 111 can be formed with a phthalocyanine-based compound such as phthalocyanine (abbreviation: H$_2$Pc) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-dia mine (abbreviation: DNTPD), a high molecular compound such as poly(ethylenedioxythiophene)/poly(styrenesulfonic acid) (PEDOT/PSS), or the like.

The hole-injection layer 111 can be formed using a composite material in which a substance exhibiting an electron-accepting property (hereinafter simply referred to as "electron-accepting substance") with respect to a substance having a hole-transport property is contained in the substance having a hole-transport property. In this specification, the composite material refers to not a material in which two materials are simply mixed but a material in the state where charge transfer between the materials can be caused by a mixture of a plurality of materials. This charge transfer includes the charge transfer that occurs only when an electric field exists.

Note that the use of such a substance having a hole-transport property which contains an electron-accepting substance enables selection of a material used to form an electrode regardless of its work function. In other words, besides a material having a high work function, a material having a low work function can also be used for the electrode functioning as an anode. As the electron-accepting substance, 7,7,8,8-tetracyano-2,3,5,6-tetrafluoroquinodimethane (abbreviation: F$_4$-TCNQ), chloranil, and the like can be given. A transition metal oxide can also be used. Oxides of the metals that belong to Group 4 to Group 8 of the periodic table can be suitably used. Specifically, vanadium oxide, niobium oxide, tantalum oxide, chromium oxide, molybdenum oxide, tungsten oxide, manganese oxide, and rhenium oxide are preferable in that their electron-accepting property is high. Among these oxides, molybdenum oxide can be suitably used as the electron-accepting substance because it is stable in the air, has a low hygroscopic property, and is easily treated.

As the substance having a hole-transport property used for the composite material, a variety of organic compounds such as aromatic amine compounds, carbazole compounds, aromatic hydrocarbons, and high molecular compounds (e.g., oligomers, dendrimers, or polymers) can be used. Note that the organic compound used for the composite material is preferably an organic compound having a high hole-transport property. Specifically, a substance having a hole mobility of $1\times10^{-6}$ cm$^2$/Vs or more is preferably used. However, any other substances may be used as long as the substance has a hole-transport property higher than an electron-transport property. Organic compounds that can be used as the substance having a hole-transport property in the composite material are specifically given below.

Examples of the aromatic amine compounds include N,N'-di(p-tolyl)-N,N'-diphenyl-p-phenylenediamine (abbreviation: DTDPPA), DPAB, DNTPD, and 1,3,5-tris[N-(4-diphenylaminophenyl)-N-phenylamino]benzene (abbreviation: DPA3B).

Specific examples of the carbazole compounds that can be used for the composite material include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Other examples of the carbazole compounds that can be used for the composite material include 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene.

Examples of the aromatic hydrocarbons that can be used for the composite material include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Besides, pentacene, coronene, or the like can also be used. As these aromatic hydrocarbons given here, it is preferable that an aromatic hydrocarbon having a hole mobility of $1\times10^{-6}$ cm$^2$/Vs or more and having 14 to 42 carbon atoms be used.

Note that the aromatic hydrocarbons that can be used for the composite material may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA).

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N-bis(phenyl)benzidine] (abbreviation: poly-TPD) can also be used.

The hole-transport layer 112 is a layer containing a substance having a hole-transport property. As the substance having a hole-transport property, those given above as the substances having hole-transport properties can be used. Note that detailed description is omitted to avoid repetition. Refer to the description of the composite material.

The light-emitting layer 113 is a layer containing a light-emitting substance. The light-emitting layer 113 may be formed with a film containing only a light-emitting substance or a film in which the light-emitting substance is dispersed in a host material.

There is no particular limitation on a material that can be used as the light-emitting substance in the light-emitting layer 113, and light emitted from the material may be either fluorescence or phosphorescence. The following substances can be used as the light-emitting substance. Examples of fluorescent substances include N,N'-bis[4-(9-phenyl-9H-fluoren-9-yl)phenyl]-N,N'-diphenyl-pyrene-1,6-diamine (abbreviation: 1,6FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N''',N'''-octaphenyldibenzo[g,p]chrysene-2,7,10,15-tetraamine (abbreviation: DBC 1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]N,9-diphenyl-9H-carbazol-3-amine (abbreviation: 2PCABPhA), N-(9,10-diphenyl-2-anthryl)-N,N'nN''-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1t-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM). Examples of blue-emissive phosphorescent materials include an organometallic iridium complex having a 4H-triazole skeleton, such as tris {2-[5-(2-methylphenyl)-4-(2,6-dimethylphenyl)-4H-1,2,4-triazol-3-yl-κN2]phenyl-κC}iridium (III) (abbreviation: Ir(mpptz-dmp)$_3$), tris(5-methyl-3,4-diphenyl-4H-1,2,4-triazolato)iridium(III) (abbreviation: Ir(Mptz)$_3$), or tris[4-(3-biphenyl)-5-isopropyl-3-phenyl-4H-1,2,4-triazolato]iridium(III) (abbreviation: Ir(iPrptz-3b)$_3$); an organometallic iridium complex having a 1H-triazole skeleton, such as tris[3-methyl-1-(2-methylphenyl)-5-phenyl-1H-1,2,4-triazolato]iridium(III) (abbreviation: Ir(Mptz1-mp)$_3$) or tris(1-methyl-5-phenyl-3-propyl-1H-1,2,4-triazolato)iridium(III) (abbreviation: Ir(Prptz1-Me)$_3$); an organometallic iridium complex having an imidazole skeleton, such as fac-tris[1-(2,6-diisopropylphenyl)-2-phenyl-1H-imidazole]iridium(III) (abbreviation: Ir(iPrpmi)$_3$), or tris[3-(2,6-dimethylphenyl)-7-methylimidazo[1,2-f]phenanthridinato]iridium(III) (abbreviation: Ir(dmpimpt-Me)$_3$); and an organometallic iridium complex in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: Flrpic), bis{2-[3',5'-bis(trifluoromethyl)phenyl]pyridinato-N,C$^{2'}$}iridium(III) picolinate (abbreviation: Ir(CF$_3$ ppy)$_2$(pic)), or bis[2-(4',6'-difluorophenyl)pyridinato-N,C$^{2'}$]iridium(III) acetylacetonate (abbreviation: FIr(acac)). Note that an organometallic iridium complex having a 4H-triazole skeleton has excellent reliability and emission efficiency and thus is particularly preferable. Examples of green-emissive phosphorescent materials include an organometallic iridium complex having a pyrimidine skeleton, such as tris(4-methyl-6-phenylpyrimidinato)iridium(III) (abbreviation: Ir(mppm)$_3$), tris(4-t-butyl-6-phenylpyrimidinato)iridium(III) (abbreviation: Ir(tBuppm)$_3$), (acetylacetonato)bis(6-methyl-4-phenylpyrimidinato)iridium(III) (abbreviation: Ir(mppm)$_2$(acac)), (acetylacetonato)bis(6-tert-butyl-4-phenylpyrimidinato)iridium(III) (abbreviation: Ir(tBuppm)$_2$(acac)), (acetylacetonato)bis[6-(2-norbornyl)-4-phenylpyrimidinato]iridium(III) (abbreviation: Ir(nbppm)$_2$(acac)), (acetylacetonato)bis[5-methyl-6-(2-methylphenyl)-4-phenylpyrimidinato]iridium(III) (abbreviation: Ir(mpmppm)$_2$(acac)), or (acetylacetonato)bis(4,6-diphenylpyrimidinato)iridium(III) (abbreviation: Ir(dppm)$_2$(acac)); an organometallic iridium complex having a pyrazine skeleton, such as (acetylacetonato)bis(3,5-dimethyl-2-phenylpyrazinato)iridium(III) (abbreviation: Ir(mppr-Me)$_2$(acac)) or (acetylacetonato)bis(5-isopropyl-3-methyl-2-phenylpyrazinato)iridium(III) (abbreviation: Ir(mppr-iPr)$_2$(acac)); an organometallic iridium complex having a pyridine skeleton, such as tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation: Ir(ppy)$_2$(acac)), bis(benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), tris(2-phenylquinolinato-N,C$^{2'}$)iridium(III) (abbreviation: Ir(pq)$_3$), or bis(2-phenylquinolinato-N,C$^{2'}$)iridium(III) acetylacetonate (abbreviation: Ir(pq)$_2$(acac)); and a rare earth metal complex such as tris(acetylacetonato)(monophenanthroline)terbium(III) (abbreviation: Tb(acac)$_3$(Phen)). Examples of red-emissive phosphorescent materials include an organometallic iridium complex having a pyrimidine skeleton, such as (diisobutyrylmethano)bis[4,6-bis(3-methylphenyl)pyrimidinato]iridium(III) (abbreviation: Ir(5mdppm)$_2$(dibm)), bis[4,6-bis(3-methylphenyl)pyrimidinato](dipivaloylmethanato)iridium(III) (abbreviation: Ir(5mdppm)$_2$(dpm)), or bis[4,6-di(naphthalen-1-yl)pyrimidinato](dipivaloylmethanato)iridium(III) (abbreviation: Ir(dlnpm)$_2$(dpm)); an organometallic iridium complex having a pyrazine skeleton, such as (acetylacetonato)bis(2,3,5-triphenylpyrazinato)iridium(III) (abbreviation: Ir(tppr)$_2$(acac)), bis(2,3,5-triphenylpyrazinato)(dipivaloylmethanato)iridium(III) (abbreviation: Ir(tppr)$_2$(dpm)), or (acetylacetonato)bis[2,3-bis(4-fluorophenyl)quinoxalinato]iridium(III) (abbreviation: Ir(Fdpq)$_2$(acac)); an organometallic iridium complex having an isoquinoline skeleton, such as tris(1-phenylisoquinolinato-N,C$^{2'}$)iridium(III) (abbreviation: Ir(piq)$_3$) or bis(1-phenylisoquinolinato-N,C$^{2'}$)iridium(III)acetylacetonate (abbreviation: Ir(piq)$_2$(acac)); a platinum complex such as 2,3,7,8,12,13,17,18-octaethyl-21H, 23H-porphyrin platinum(II) (abbreviation: PtOEP); and a rare earth metal complex such as tris(1,3-diphenyl-1,3-propanedionato)(monophenanthroline)europium(III) (abbreviation: Eu(DBM)$_3$(Phen)) or tris[1-(2-thenoyl)-3,3,3-trifluoroacetonato](monophenanthroline)europium(III) (abbreviation: Eu(TTA)$_3$(Phen)). Note that an organometallic iridium complex having a pyrimidine skeleton has distinctively high reliability and emission efficiency and thus is particularly preferable. Further, because an organometallic iridium complex having a pyrazine skeleton can provide red light emission with favorable chromaticity, the use of the organometallic iridium complex improves a color rendering property of a white-emissive light-emitting element. Note that the heterocyclic compound of one embodiment of the present invention also emits blue to ultraviolet light and thus can be used as a light-emitting substance.

The light-emitting substance may be selected from known substances as well as from the substances given above.

As a host material in which the light-emitting substance is dispersed, the heterocyclic compound of one embodiment of the present invention is suitably used.

Since the heterocyclic compound of one embodiment of the present invention has a wide band gap and a high T$_1$ level, the heterocyclic compound can be suitably used particularly as a host material in which a light-emitting substance emitting high-energy light is dispersed, such as a blue-emissive fluorescent substance or a green-emissive phosphorescent substance. Needless to say, the heterocyclic compound can also be used as a host material in which a fluorescent substance emitting light having a wavelength longer than the blue light wavelength or a phosphorescent substance emitting light having a wavelength longer than the green light wavelength is dispersed. In addition, it is effective to use the heterocyclic compound as a material of a carrier-transport layer (preferably an electron-transport layer) adjacent to a light-emitting layer. Since the heterocyclic compound has a wide band gap or a high T$_1$ level, even when the light-emitting substance is a material emitting high-energy light, such as a blue-emissive fluorescent substance or a green-emissive phosphorescent substance, the energy of carriers to be recombined in a host material can be effectively transferred to the light-emitting substance. Thus, a light-emitting element having a high emission efficiency can be manufactured. Note that in the case where the heterocyclic compound is used as a host material or a material of a carrier-transport layer, the light-emitting substance is preferably, but not limited to, a substance having a narrower band gap than the heterocyclic compound or a substance having a lower singlet or T$_1$ level than the heterocyclic compound.

The heterocyclic compound of one embodiment of the present invention preferably has the structure in which the indolo[3,2,1-jk]carbazole skeleton and the dibenzo[f,h]quinoxaline skeleton are bonded to each other through an arylene group to achieve a wide band gap or a high T$_1$ level. The heterocyclic compound with such a structure has advantages in that the quality of a film fainted by evaporation is favorable and synthesis can be easily performed.

The heterocyclic compound described in Embodiment 1 (the heterocyclic compound represented by the general formula (G1)), which forms part of the heterocyclic compound of one embodiment of the present invention, is more preferable.

In the case where the above heterocyclic compound of one embodiment of the present invention is not used for the host material, a known material can be used for the host material.

Examples of materials which can be used as the above host material are given below. The following are examples of materials having an electron-transport property: a metal complex such as bis(10-hydroxybenzo[h]quinolinato)beryllium (II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ); a heterocyclic compound having a polyazole skeleton such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II); a heterocyclic compound having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyrimidine (abbreviation: 4,6mDBTP2 Pm-II); and a heterocyclic compound having a pyridine skeleton such as 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB). Among the above materials, a heterocyclic compound having a diazine skeleton and a heterocyclic compound having a pyridine skeleton have high reliability and are thus preferable. Specifically, a heterocyclic compound having a diazine (pyrimidine or pyrazine) skeleton has a high electron-transport property to contribute to a reduction in driving voltage. Note that the heterocyclic compound of one embodiment of the present invention has a relatively large electron-transport property and thus classified into a material having an electron-transport property.

The following are examples of materials which have a hole-transport property: a compound having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(Spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF); a compound having a carbazole skeleton such as 1,3-bis(N-carbazolyl)benzene (abbreviation: mCP), CBP, 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl- 9H-fluoren-9-yl)phenyl]-6-phenyldibenzothiophene (abbreviation: DBTFLP-IV); and a compound having a furan skeleton such as 4,4',4''-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II). Among the above materials, a compound having an aromatic amine skeleton and a compound having a carbazole skeleton are preferable because these compounds are highly reliable and have high carrier-transport properties to contribute to a reduction in driving voltage.

Note that when the light-emitting substance is a phosphorescent material, a substance having larger $T_1$ level than the emissive phosphorescent material is preferably selected as the host material, and when the light-emitting substance is a fluorescent material, a substance having a wider band gap of a singlet than the emissive fluorescent material is preferably selected as the host material. The light-emitting layer may contain a third substance in addition to the host material and the phosphorescent substance. Note that this statement does not exclude the possibility that the light-emitting layer contains a component other than the host materials, the phosphorescent substances, and the third substance.

Here, to achieve a high emission efficiency of a light-emitting element that uses a phosphorescent material, energy transfer between the host material and the phosphorescent substance will be considered. Carrier recombination occurs in both the host material and the phosphorescent substance; thus, efficient energy transfer from the host material to the phosphorescent substance is needed to increase emission efficiency.

In this embodiment, a phosphorescent substance is used as the light-emitting substance. In an absorption spectrum of the phosphorescent substance, an absorption band that is considered to contribute to light emission most greatly is that corresponding to direct transition from a ground state to a triplet excited state, which is on the longest wavelength side. Therefore, it is preferable that the emission spectrum (a fluorescence spectrum and a phosphorescence spectrum) of the host material overlap with the absorption band on the longest wavelength side of the phosphorescent substance.

Thus, it is preferable that the light-emitting layer include a third substance in addition to the host material and the light-emitting substance and a combination of the host material and the third substance form an exciplex (also referred to as an excited complex).

In that case, at the time of recombination of carriers (electrons and holes) in the light-emitting layer, the host material and the third substance form an exciplex. A fluorescence spectrum of the exciplex is on a longer wavelength side than a fluorescence spectrum of the host material alone or the third substance alone. Therefore, energy transfer from a singlet excited state of the exciplex can be maximized while the $T_1$ levels of the host material and the third substance are kept higher than the $T_1$ level of the phosphorescent substance. In addition, the $T_1$ level and the $S_1$ level of the exciplex are close to each other; therefore, the fluorescence spectrum and the phosphorescence spectrum exist at substantially the same position. Accordingly, both the fluorescence spectrum and the phosphorescence spectrum of the exciplex can have a large overlap with an absorption corresponding to the transition of the phosphorescent substance from the singlet ground state to the triplet excited state (a broad absorption band of the phosphorescent substance existing on the longest wavelength side), and thus a light-emitting element having a high energy transfer efficiency can be obtained.

As the third substance, the above material which can be used as the host material can be used. There is no particular limitation on the host materials and the third substance as long as they can form an exciplex; a combination of a compound which readily accepts electrons (a compound having an electron-transport property) and a compound which readily accepts holes (a compound having a hole-transport property) is preferably employed.

In the case where a compound having an electron-transport property and a compound having a hole-transport property are used for the host material and the third substance, carrier balance can be controlled by the mixture ratio of the compounds. Specifically, the ratio of the host material to the third substance is preferably from 1:9 to 9:1. Note that in that case, the following structure may be employed: a light-emitting layer in which one kind of a light-emitting substance is dispersed is divided into two layers, and the two layers have different mixture ratios of the host material to the third substance. With this structure, the carrier balance of the light-emitting element can be optimized, so that the lifetime of the light-emitting element can be improved. Furthermore, one of the light-emitting layers may function as a hole-transport layer and the other of the light-emitting layers may function as an electron-transport layer.

In the case where the light-emitting layer having the above-described structure is formed using a plurality of materials, the light-emitting layer can be formed using co-evaporation by a vacuum evaporation method; or an ink-jet method, a spin coating method, a dip coating method, or the like using a solution of the materials. Note that co-evaporation is an evaporation method in which a plurality of different substances are concurrently vaporized from respective different evaporation sources.

The electron-transport layer 114 is a layer containing a substance having an electron-transport property. For example, the electron-transport layer 114 is formed using a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), BeBq$_2$, or BAlq. A metal complex having an oxazole-based or thiazole-based ligand, such as ZnPBO or ZnBTZ can also be used. Other than the metal complexes, PBD, OXD-7, TAZ, bathophenanthroline (abbreviation: BPhen), bathocuproine (abbreviation: BCP), or the like can also be used. The substances given here are mainly ones having an electron mobility of $10^{-6}$ cm$^2$/Vs or higher. Note that any substance other than the above substances may be used for the electron-transport layer as long as the substance has an electron-transport property higher than a hole-transport property.

Alternatively, the heterocyclic compound of one embodiment of the present invention may be used as a material of the electron-transport layer 114. The heterocyclic compound of one embodiment of the present invention has a wide band gap and a high $T_1$ level and thus can effectively prevent transfer of excitation energy in the light-emitting layer to the electron-transport layer 114 to inhibit a reduction in emission efficiency due to the excitation energy transfer, leading to the formation of a light-emitting element having a high emission efficiency. Moreover, the heterocyclic compound of one embodiment of the present invention has a high carrier-transport property; thus, a light-emitting element with a low driving voltage can be provided.

The electron-transport layer is not limited to a single layer, and may be a stack including two or more layers containing any of the above substances.

Between the electron-transport layer and the light-emitting layer, a layer that controls transport of electron carriers may be provided. This is a layer formed by addition of a small amount of a substance having a high electron-trapping property to the above materials having a high electron-transport property, and the layer is capable of adjusting carrier balance by retarding transport of electron carriers. Such a structure is very effective in preventing a problem (such as a reduction in element lifetime) caused when electrons pass through the light-emitting layer.

It is preferable that the host material in the light-emitting layer and a material of the electron-transport layer have the same skeleton, in which case the transport of carriers can be smooth and thus the driving voltage can be reduced. Moreover, it is effective that the host material and the material of the electron-transport layer be the same material.

An electron-injection layer 115 may be provided in contact with the second electrode 102 between the electron-transport layer 114 and the second electrode 102. For the electron-injection layer 115, lithium, calcium, lithium fluoride (LiF), cesium fluoride (CsF), calcium fluoride (CaF$_2$), or the like can be used. A composite material of a substance having an electron-transport property and a substance exhibiting an electron-donating property (hereinafter simply referred to as electron-donating substance) with respect to the substance having an electron-transport property can also be used. Examples of the electron-donating substance include an alkali metal, an alkaline earth metal, and compounds thereof. Note that such a composite material is preferably used for the electron-injection layer 115, in which case electrons are injected efficiently from the second electrode 102. With this structure, a conductive material as well as a material having a low work function can be used for the cathode.

For the electrode functioning as a cathode, any of metals, alloys, electrically conductive compounds, and mixtures thereof which have a low work function (specifically, a work function of 3.8 eV or less) or the like can be used. Specific examples of such a cathode material are elements belonging to Groups 1 and 2 of the periodic table, such as lithium (Li), cesium (Cs), magnesium (Mg), calcium (Ca), and strontium (Sr), alloys thereof (e.g., MgAg and AlLi), rare earth metals such as europium (Eu) and ytterbium (Yb), alloys thereof, and the like. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of the work function. Films of these electrically conductive materials can be formed by a sputtering method, an ink-jet method, a spin coating method, or the like.

Any of a variety of methods can be used to form the EL layer 103 regardless whether it is a dry process or a wet process. For example, a vacuum evaporation method, an ink-jet method, or a spin coating method may be used. Different formation methods may be used for the electrodes or the layers.

The electrode may be formed by a wet method using a sol-gel method, or by a wet method using paste of a metal material. Alternatively, the electrode may be formed by a dry method such as a sputtering method or a vacuum evaporation method.

Note that the structure of the EL layer provided between the first electrode 101 and the second electrode 102 is not limited to the above structure. However, it is preferable that a light-emitting region where holes and electrons recombine be positioned away from the first electrode 101 and the second electrode 102 so as to prevent quenching due to the proximity of the light-emitting region and a metal used for an electrode or a carrier-injection layer.

In order to prevent transfer of energy from an exciton generated in the light-emitting layer, the hole-transport layer and the electron-transport layer which are in direct contact with the light-emitting layer, particularly a carrier-transport layer in contact with a side closer to the light-emitting region in the light-emitting layer 113 is formed with a substance having a wider band gap than the light-emitting substance included in the light-emitting layer.

In the light-emitting element having the above-described structure, current flows due to a potential difference applied between the first electrode 101 and the second electrode 102, and holes and electrons recombine in the light-emitting layer 113 which contains a substance having a high light-emitting property, so that light is emitted. In other words, a light-emitting region is formed in the light-emitting layer 113.

Light is extracted out through one or both of the first electrode 101 and the second electrode 102. Therefore, one or both of the first electrode 101 and the second electrode 102 are light-transmitting electrodes. In the case where only the first electrode 101 is a light-transmitting electrode, light is extracted from the substrate side through the first electrode 101. In contrast, when only the second electrode 102 is a light-transmitting electrode, light is extracted from the side opposite to the substrate side through the second electrode 102. In the case where both the first electrode 101 and the second electrode 102 are light-transmitting electrodes, light is extracted from both the substrate side and the side opposite to the substrate side through the first electrode 101 and the second electrode 102.

Since the light-emitting element of this embodiment is formed using the heterocyclic compound of one embodiment of the present invention, which has a wide band gap, efficient light emission can be obtained even if a light-emitting substance has a wide band gap and emits blue fluorescence or green phosphorescence, and the light-emitting element can have a high emission efficiency. Thus, a light-emitting element with lower power consumption can be provided. Moreover, the heterocyclic compound of one embodiment of the present invention has a high carrier-transport property; thus, a light-emitting element with a low driving voltage can be provided.

[Embodiment 4]

In this embodiment, one embodiment of a light-emitting element having a structure in which a plurality of light-emitting units are stacked (hereinafter also referred to as stacked-type element) will be described with reference to FIG. 1B. This light-emitting element includes a plurality of light-emitting units between a first electrode and a second electrode. Each light-emitting unit can have the same structure as the EL layer 103 which is described in Embodiment 3. In other words, the light-emitting element described in Embodiment 3 is a light-emitting element having one light-emitting unit while the light-emitting element described in this embodiment is a light-emitting element having a plurality of light-emitting units.

Figure 1B:
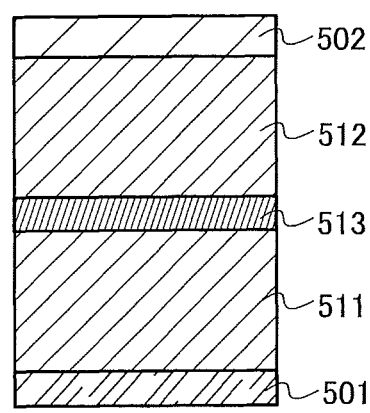

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 respectively correspond to the first electrode 101 and the second electrode 102 in Embodiment 3, and materials described in Embodiment 3 can be used. Furthermore, the structures of the first light-emitting unit 511 and the second light-emitting unit 512 may be the same or different.

The charge generation layer 513 includes a composite material of an organic compound and a metal oxide. As this composite material of an organic compound and a metal oxide, the composite material that can be used for the hole-injection layer and described in Embodiment 3 can be used. Note that in the light-emitting unit whose anode side surface is in contact with the charge generation layer, a hole-transport layer is not necessarily provided because the charge generation layer can also function as the hole-transport layer.

The charge generation layer 513 may have a stacked-layer structure of a layer containing the composite material and a layer containing another material. For example, a layer containing the composite material may be combined with a layer containing a compound of a substance selected from electron-donating substances and a compound having a high electron-transport property. Moreover, the charge generation layer 513 may be formed by combining a layer containing the composite material with a transparent conductive film The charge generation layer 513 may have any structure as long as electrons can be injected to a light-emitting unit on one side and holes can be injected to a light-emitting unit on the other side when a voltage is applied between the first electrode 501 and the second electrode 502. For example, in FIG. 1B, any layer can be used as the charge generation layer 513 as long as the layer injects electrons into the first light-emitting unit 511 and holes into the second light-emitting unit 512 when a voltage is applied such that the potential of the first electrode is higher than that of the second electrode.

Although the light-emitting element having two light-emitting units is described in this embodiment, the present invention can be similarly applied to a light-emitting element in which three or more light-emitting units are stacked. With a plurality of light-emitting units partitioned by the charge generation layer between a pair of electrodes, as in the light-emitting element of this embodiment, light with high luminance can be obtained while current density is kept low; thus, a light-emitting element having a long lifetime can be obtained. In addition, a low power consumption light-emitting device which can be driven at a low voltage can be achieved.

By making the light-emitting units emit light of different colors from each other, the light-emitting element can provide light emission of a desired color as a whole. For example, by forming a light-emitting element having two light-emitting units such that the emission color of the first light-emitting unit and the emission color of the second light-emitting unit are complementary colors, the light-emitting element can provide white light emission as a whole. Note that the word "complementary" means color relationship in which an achromatic color is obtained when colors are mixed. In other words, when lights obtained from substances which emit light of complementary colors are mixed, white light emission can be obtained. Furthermore, the same can be applied to a light-emitting element having three light-emitting units. For example, the light-emitting element as a whole can provide white light emission when the emission color of the first light-emitting unit is red, the emission color of the second light-emitting unit is green, and the emission color of the third light-emitting unit is blue. Alternatively, in the case of employing a light-emitting element in which a phosphorescent substance is used for a light-emitting layer of one light-emitting unit and a fluorescent substance is used for a light-emitting layer of the other light-emitting unit, both fluorescence and phosphorescence can be efficiently emitted from the light-emitting element. For example, when red phosphorescence and green phosphorescence are obtained from one light-emitting unit and blue fluorescence is obtained from the other light-emitting unit, white light with a high emission efficiency can be obtained.

Since the light-emitting element of this embodiment contains the heterocyclic compound of one embodiment of the present invention, the light-emitting element can have a high emission efficiency or operate at a low driving voltage. In addition, since light emission derived from the light-emitting substance can be obtained from the light-emitting unit that contains the heterocyclic compound, color adjustment of the light-emitting element as a whole is easy.

Note that this embodiment can be combined with any of the other embodiments and examples as appropriate.

[Embodiment 5]

In this embodiment, a light-emitting device which includes a light-emitting element that contains the heterocyclic compound of one embodiment of the present invention will be described.

Figure 3A:
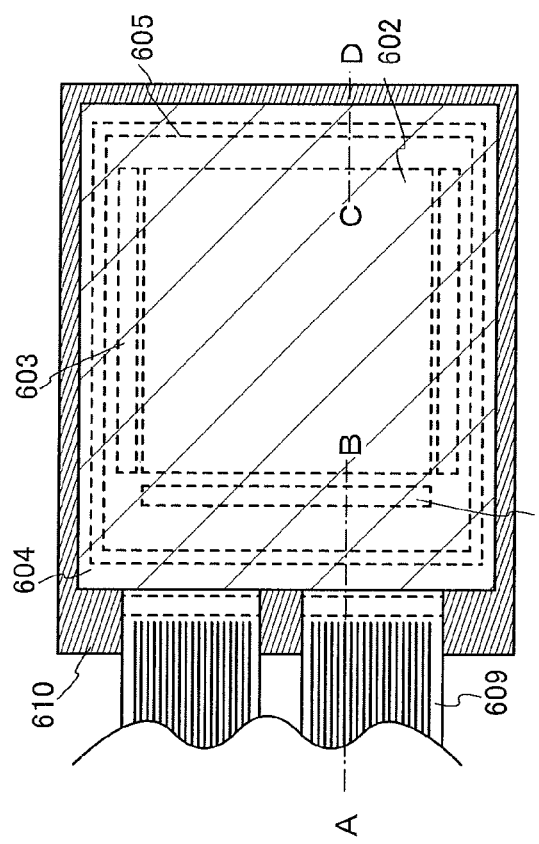
FIGS. 3A and 3B are conceptual diagrams of an active matrix light-emitting device.
Figure 3B:
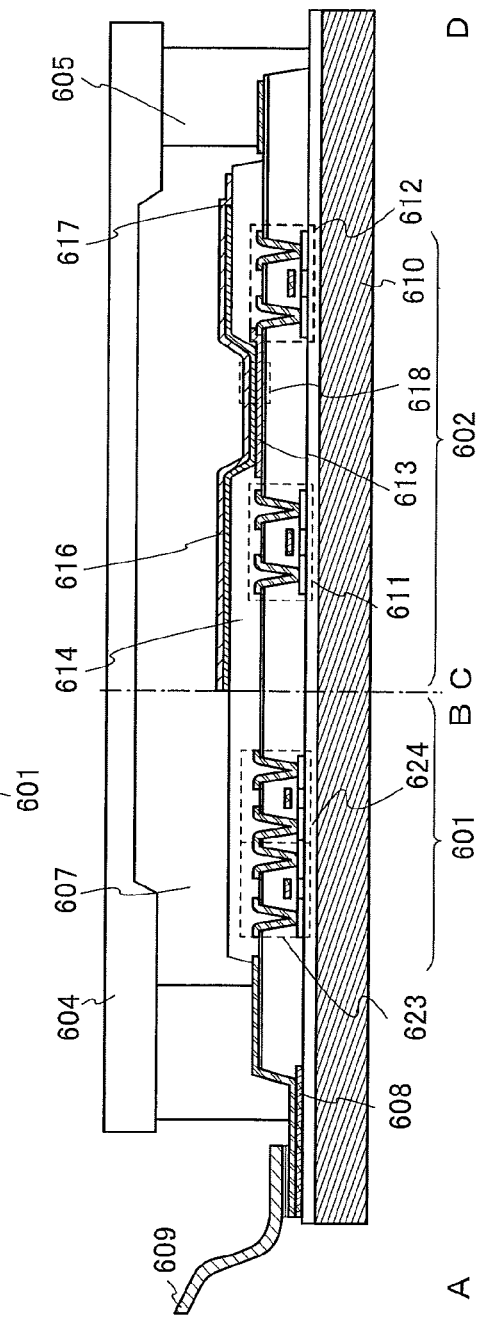

In this embodiment, an example of the light-emitting device manufactured using a light-emitting element that contains the heterocyclic compound of one embodiment of the present invention will be described with reference to FIGS. 3A and 3B. Note that FIG. 3A is a top view of the light-emitting device and FIG. 3B is a cross-sectional view taken along lines A-B and C-D in FIG. 3A. This light-emitting device includes a driver circuit portion (source side driver circuit) 601, a pixel portion 602, and a driver circuit portion (gate side driver circuit) 603, which control light emission of a light-emitting element and are denoted by dotted lines. A reference numeral 604 denotes a sealing substrate; 605, a sealant; and 607, a space surrounded by the sealant 605.

Reference numeral 608 denotes a wiring for transmitting signals to be input to the source side driver circuit 601 and the gate side driver circuit 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

A cross-sectional structure is described with reference to FIG. 3B. The driver circuit portions 601 and 603 and the pixel portion 602 are formed over an element substrate 610; here, the source side driver circuit 601, which is a driver circuit portion, and one of the pixels in the pixel portion 602 are shown.

As the source side driver circuit 601, a CMOS circuit in which an n-channel transistor 623 and a p-channel transistor 624 are combined is formed. In addition, the driver circuit may be formed with any of a variety of circuits such as a CMOS circuit, a PMOS circuit, and an NMOS circuit. Although a driver integrated type in which the driver circuit is formed over the substrate is illustrated in this embodiment, the driver circuit is not necessarily formed over the substrate, and the driver circuit can be formed outside, not over the substrate. Either a staggered transistor or an inverted staggered transistor may be employed. A semiconductor layer for forming the transistors may be formed using any material as long as the material exhibits semiconductor characteristics; for example, an element belonging to Group 14 of the periodic table such as silicon (Si) and germanium (Ge), a compound such as gallium arsenide and indium phosphide, and an oxide such as zinc oxide and tin oxide can be given. For the oxide exhibiting semiconductor characteristics (oxide semiconductor), a composite oxide of an element selected from indium, gallium, aluminum, zinc, and tin can be used.

Examples thereof are zinc oxide (ZnO), indium oxide containing zinc oxide (indium zinc oxide), and oxide containing indium oxide, gallium oxide, and zinc oxide (IGZO: indium gallium zinc oxide). An organic semiconductor may also be used. The semiconductor layer may have either a crystalline structure or an amorphous structure. Specific examples of the crystalline semiconductor layer are a single crystal semiconductor, a polycrystalline semiconductor, and a microcrystalline semiconductor.

The pixel portion 602 includes a plurality of pixels including a switching transistor 611, a current controlling transistor 612, and a first electrode 613 electrically connected to a drain of the current controlling transistor 612. Note that to cover an end portion of the first electrode 613, an insulator 614 is formed, for which a positive photosensitive resin film is used here.

In order to improve coverage of a film formed over the insulator 614, the insulator 614 is formed to have a curved surface with curvature at its upper or lower end portion. For example, in the case where a positive photosensitive acrylic resin is used for a material of the insulator 614, only the upper end portion of the insulator 614 preferably has a surface with a curvature radius (0.2 µm to 3 µm). As the insulator 614, either a negative photosensitive material or a positive photosensitive material can be used.

An EL layer 616 and a second electrode 617 are formed over the first electrode 613. As a material used for the first electrode 613, the materials described in Embodiment 3 can be used. For example, a stack including a titanium nitride film and a film containing aluminum as its main component, or a stack including three layers of a titanium nitride film, a film containing aluminum as its main component, and a titanium nitride film can be used. The stacked structure achieves low wiring resistance, a favorable ohmic contact, and a function as an anode.

The EL layer 616 is formed by any of a variety of methods such as an evaporation method using an evaporation mask, an ink-jet method, and a spin coating method. The EL layer 616 contains the heterocyclic compound of one embodiment of the present invention. Furthermore, for another material included in the EL layer 616, any of low molecular-weight compounds and polymeric compounds (including oligomers and dendrimers) may be used.

As a material used for the second electrode 617, those described in Embodiment 3 used. In the case where light generated in the EL layer 616 passes through the second electrode 617, a stack including a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that a light-emitting element 618 is fainted with the first electrode 613, the EL layer 616, and the second electrode 617. The light-emitting element has the structure described in Embodiment 3 or 4. In the light-emitting device of this embodiment, the pixel portion 602, which includes a plurality of light-emitting elements, may include both the light-emitting element with the structure described in Embodiment 3 or 4 and a light-emitting element with a structure other than those structures.

The sealing substrate 604 is attached to the element substrate 610 with the sealant 605, so that the light-emitting element 618 is provided in the space 607 surrounded by the element substrate 610, the sealing substrate 604, and the sealant 605. The space 607 is filled with filler. The filler may be an inert gas (such as nitrogen or argon), or a resin and/or a desiccant.

An epoxy-based resin or glass frit is preferably used for the sealant 605. It is preferable that such a material do not transmit moisture or oxygen as much as possible. As the element substrate 610 and sealing substrate 604, a glass substrate, a quartz substrate, or a plastic substrate formed of fiber reinforced plastic (FRP), poly(vinyl fluoride) (PVF), a polyester, an acrylic resin, or the like can be used.

As described above, the light-emitting device manufactured by using the light-emitting element that contains the heterocyclic compound of one embodiment of the present invention can be obtained.

FIGS. 4A and 4B illustrate examples of light-emitting devices in which full color display is achieved by forming a white-emissive light-emitting element and providing a coloring layer (a color filter) and the like. In FIG. 4A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition wall 1025, an EL layer 1028, a second electrode 1029 of the light-emitting elements, a sealing substrate 1031, a sealant 1032, and the like are illustrated.

In FIG. 4A, coloring layers (a red coloring layer 1034R, a green coloring layer 1034G, and a blue coloring layer 1034B) are provided on a transparent base material 1033. Furthermore, a black layer (a black matrix) 1035 may be additionally provided. The transparent base material 1033 provided with the coloring layers and the black layer is fixed to the substrate 1001. Note that the coloring layers and the black layer are covered with an overcoat layer 1036. As shown in FIG. 4A, emitted light is extracted without passing through any of the coloring layers in an emission region 1044W, while the emitted light is extracted through the coloring layers in emission regions 1044R, 1044B, and 1044G. Since light which does not pass through the coloring layers is white and light which passes through any one of the coloring layers is red, blue, or green, an image can be displayed using pixels of the four colors.

FIG. 4B illustrates an example in which coloring layers (a red coloring layer 1034R, a green coloring layer 1034G, and a blue coloring layer 1034B) are formed between the gate insulating film 1003 and the first interlayer insulating film 1020. As illustrated in FIG. 4B, the coloring layers may be provided between the substrate 1001 and the sealing substrate 1031.

Figure 5:
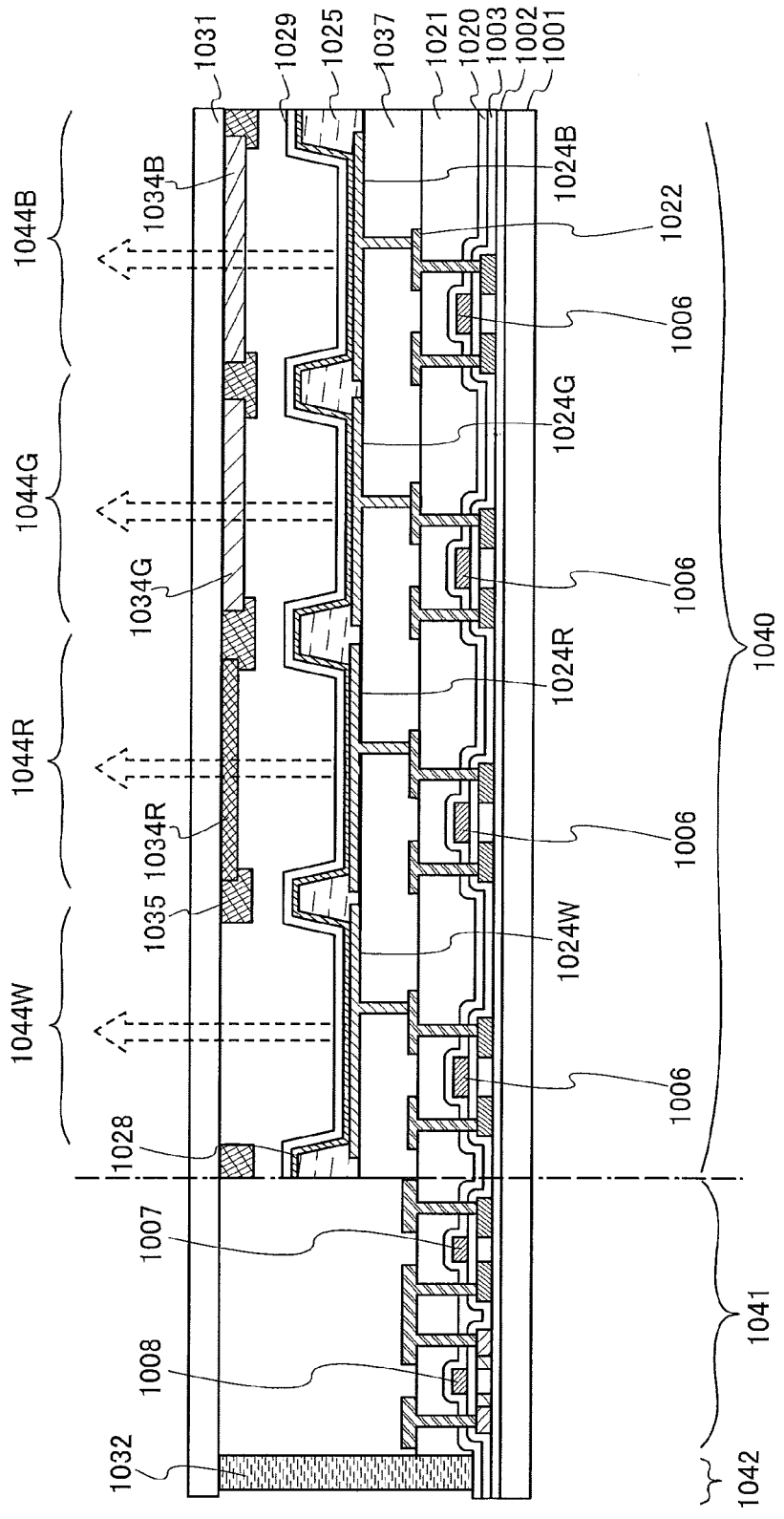
FIG. 5 is a conceptual diagram of an active matrix light-emitting device.

The above-described light-emitting devices have a structure in which light is extracted from the substrate 1001 side where the transistors are formed (a bottom emission structure), but may have a structure in which light is extracted from the sealing substrate 1031 side (a top emission structure). FIG. 5 is a cross-sectional view of a light-emitting device having a top emission structure. In this case, a substrate which does not transmit light can be used as the substrate 1001.

The first electrodes 1024W, 10248, 1024G, and 1024B are reflective electrodes. The EL layer 1028 is formed to have a structure similar to the structure described in Embodiments 3 and 4, with which white light emission can be obtained. For example, [0188] a plurality of light-emitting layers is used or a plurality of light-emitting units are employed.

In the case of a top emission structure as illustrated in FIG. 5, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer 1035 which is positioned between pixels. The coloring layers and the black layer may be covered with an overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue may be performed.

Since the light-emitting device of this embodiment uses the light-emitting element described in Embodiment 3 or 4 (the light-emitting element that contains the heterocyclic compound of one embodiment of the present invention), the light-emitting device can have favorable characteristics. Specifically, the heterocyclic compound of one embodiment of the present invention has a wide band gap and can inhibit energy transfer from a light-emitting substance; thus, a light-emitting element having a high emission efficiency can be provided, leading to a light-emitting device having reduced power consumption. Moreover, the heterocyclic compound of one embodiment of the present invention has a high carrier-transport property; thus, a light-emitting element with a low driving voltage can be provided, leading to a light-emitting device with a low driving voltage.

Figure 6A:
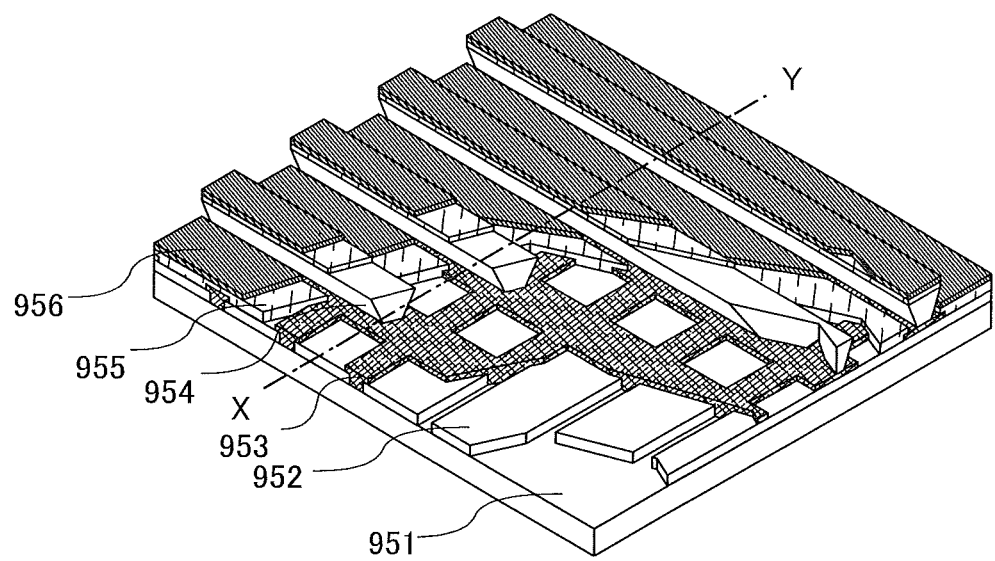
FIGS. 6A and 6B are conceptual diagrams of a passive matrix light-emitting device.
Figure 6B:
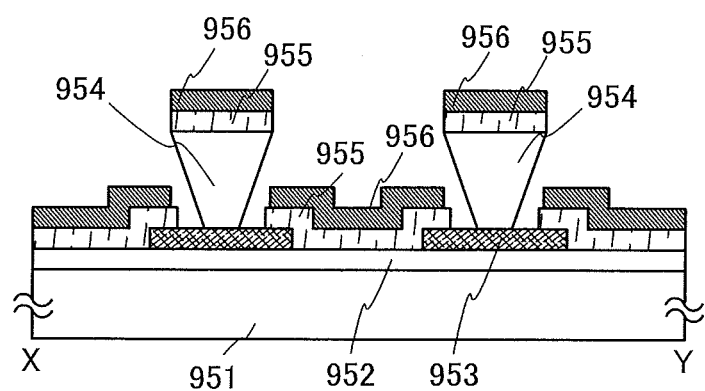

An active matrix light-emitting device is described above, whereas a passive matrix light-emitting device is described below. FIGS. 6A and 6B illustrate a passive matrix light-emitting device manufactured by application of the present invention. FIG. 6A is a perspective view of the light-emitting device, and FIG. 6B is a cross-sectional view of FIG. 6A taken along line X-Y. In FIGS. 6A and 6B, over a substrate 951, an EL layer 955 is provided between an electrode 952 and an electrode 956. An edge portion of the electrode 952 is covered with an insulating layer 953. A partition layer 954 is provided over the insulating layer 953. The sidewalls of the partition layer 954 slope so that the distance between one sidewall and the other sidewall gradually decreases toward the surface of the substrate. In other words, a cross section taken along the direction of the short side of the partition layer 954 is trapezoidal, and the base (a side in contact with the insulating layer 953) is shorter than the upper side (a side which is not in contact with the insulating layer 953). By providing the partition layer 954 in such a manner, a defect of the light-emitting element due to crosstalk can be prevented. The passive matrix light-emitting device can also be driven with low power consumption by including the light-emitting element described in Embodiment 3 or 4 (the light-emitting element that contains the heterocyclic compound of one embodiment of the present invention) capable of operating at a low driving voltage. Furthermore, the passive matrix light-emitting device can be driven with low power consumption by including the light-emitting element having a high emission efficiency (the light-emitting element described in Embodiment 3 or 4) because the light-emitting element includes the heterocyclic compound of one embodiment of the present invention.

Since many minute light-emitting elements arranged in a matrix in the light-emitting device described above can each be controlled, the light-emitting device can be suitably used as a display device for displaying images.

[Embodiment 6]

In this embodiment, electronic devices and lighting devices each including the light-emitting element described in Embodiment 3 or 4 will be described. The light-emitting element described in Embodiment 3 or 4 contains the heterocyclic compound of one embodiment of the present invention and thus has reduced power consumption; as a result, the electronic devices including a display portion and the lighting devices have reduced power consumption. In addition, the electronic devices and the lighting devices can have a low driving voltage because the light-emitting element described in Embodiment 3 or 4 has a low driving voltage.

Examples of the electronic device to which the above light-emitting element is applied include television devices (also referred to as TV or television receivers), monitors for computers and the like, cameras such as digital cameras and digital video cameras, digital photo frames, cellular phones (also referred to as mobile phones or mobile phone devices), portable game machines, portable information terminals, audio playback devices, large game machines such as pachinko machines, and the like. Specific examples of these electronic devices are given below.

Figure 7A:
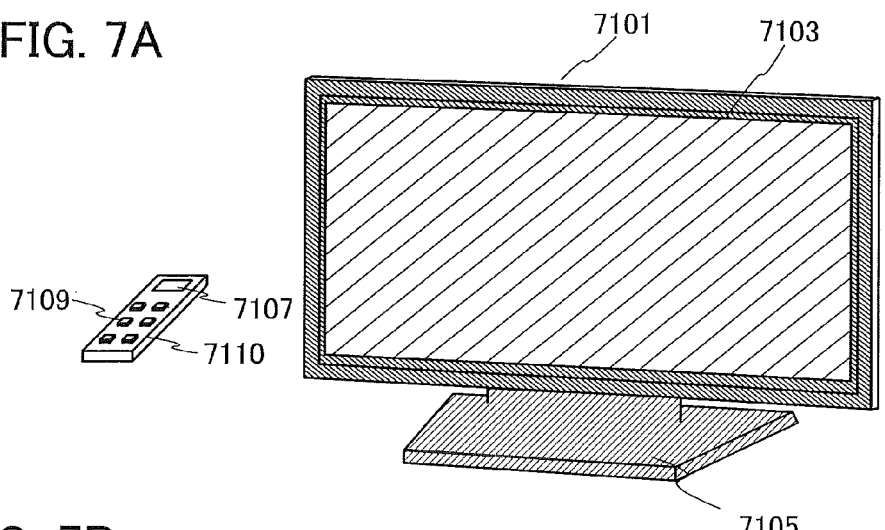
FIGS. 7A to 7D illustrate electronic devices.

FIG. 7A illustrates an example of a television device. In the television device, a display portion 7103 is incorporated in a housing 7101. Here, the housing 7101 is supported by a stand 7105. The display portion 7103 enables display of images and includes the light-emitting elements which are the same as the light-emitting element described in Embodiment 3 or 4 and arranged in a matrix.

The television device can operate with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

Figure 7B:
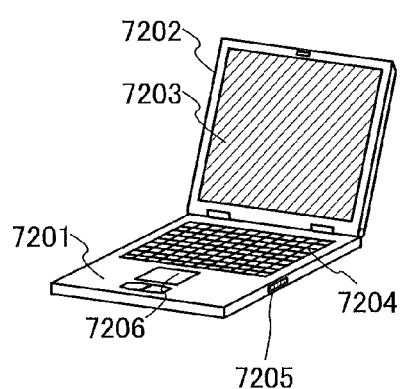

FIG. 7B illustrates a computer, which includes a main body 7201, a housing 7202, a display portion 7203, a keyboard 7204, an external connection port 7205, a pointing device 7206, and the like. Note that this computer is manufactured by using the light-emitting elements which are the same as that described in Embodiment 3 or 4 and arranged in a matrix in the display portion 7203.

Figure 7C:
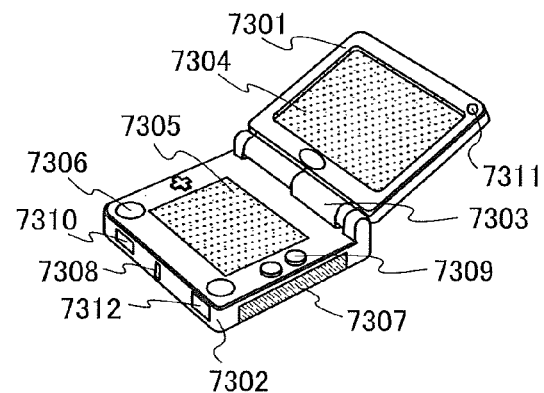

FIG. 7C illustrates a portable game machine having two housings, a housing 7301 and a housing 7302, which are connected with a joint portion 7303 so that the portable game machine can be opened or folded. A display portion 7304 including the light-emitting elements which are the same as that described in Embodiment 3 or 4 and arranged in a matrix is incorporated in the housing 7301, and a display portion 7305 is incorporated in the housing 7302. In addition, the portable game machine illustrated in FIG. 7C includes a speaker portion 7306, a recording medium insertion portion 7307, an LED lamp 7308, an input unit (an operation key 7309, a connection terminal 7310), and a microphone 7312, a sensor 7311 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and the like. Needless to say, the structure of the portable game machine is not limited to the above structure as far as the display portion including the light-emitting elements which are the same as that described in Embodiment 3 or 4 and arranged in a matrix is used as at least either the display portion 7304 or the display portion 7305, or both. The portable game machine can include other accessories as appropriate. The portable game machine illustrated in FIG. 7C has a function of reading out a program or data stored in a storage medium to display it on the display portion, and a function of sharing information with another portable game machine by wireless communication. The portable game machine illustrated in FIG. 7C can have a variety of functions without limitation to the above functions.

Figure 7D:
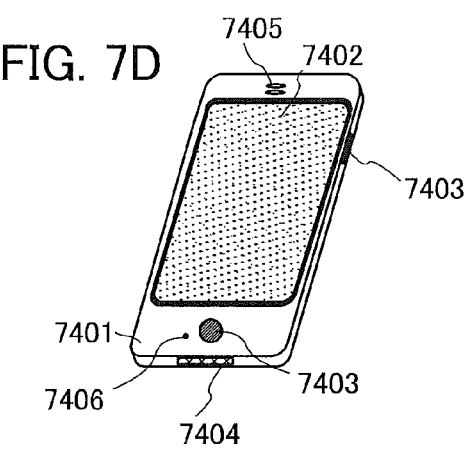

FIG. 7D illustrates an example of a mobile phone. The mobile phone is provided with a display portion 7402 incorporated in a housing 7401, operation buttons 7403, an external connection port 7404, a speaker 7405, a microphone 7406, and the like. Note that the mobile phone 7400 has the display portion 7402 including the light-emitting elements which are the same as that described in Embodiment 3 or 4 and arranged in a matrix. The light-emitting element can operate at a low driving voltage. Therefore, the mobile phone including the display portion 7402 which is formed using the light-emitting elements can have reduced power consumption and a low driving voltage.

When the display portion 7402 of the mobile phone illustrated in FIG. 7D is touched with a finger or the like, data can be input into the mobile phone. In this case, operations such as making a call and creating e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone, display on the screen of the display portion 7402 can be automatically changed by determining the orientation of the mobile phone (whether the cellular phone is placed horizontally or vertically for a landscape mode or a portrait mode).

The screen modes are switched by touch on the display portion 7402 or operation with the operation buttons 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

In the input mode, when input by touching the display portion 7402 is judged not to have been performed within a specified period by an optical sensor in the display portion 7402, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a backlight or a sensing light source which emits a near-infrared light in the display portion, an image of a finger vein, a palm vein, or the like can be taken.

The light-emitting element that contains the heterocyclic compound of one embodiment of the present invention can also be used for a light source device, and its application mode is described with reference to FIG. 8. Note that the light source device includes a light-emitting element that contains the heterocyclic compound of one embodiment of the present invention as a light irradiation unit and at least includes an input-output terminal portion which supplies current to the light-emitting element.

Figure 8:
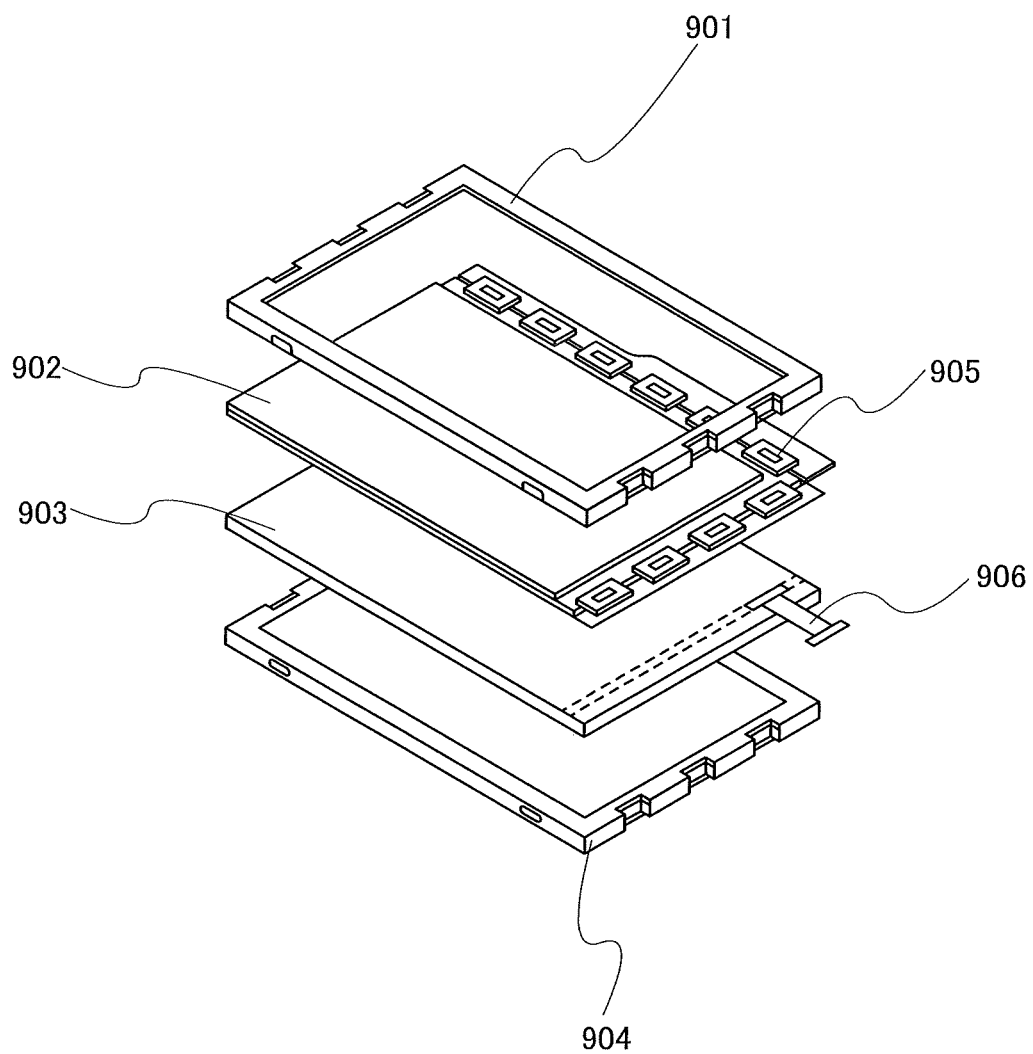
FIG. 8 illustrates a light source device.

FIG. 8 illustrates an example of a liquid crystal display device using the light-emitting elements that contains the heterocyclic compound of one embodiment of the present invention for a backlight. The liquid crystal display device illustrated in FIG. 8 includes a housing 901, a liquid crystal layer 902, a backlight 903, and a housing 904. The liquid crystal layer 902 is connected to a driver IC 905. The light-emitting element that contains the above heterocyclic compound is used for the backlight 903, to which current is supplied through a terminal 906.

The light-emitting element that contains the above heterocyclic compound is used for the backlight of the liquid crystal display device; thus, the backlight can have reduced power consumption. In addition, the use of the light-emitting element that contains the above heterocyclic compound enables manufacture of a planar-emission lighting device and further a larger-area planar-emission lighting device; therefore, the backlight can be a larger-area backlight, and the liquid crystal display device can also be a larger-area device. Furthermore, the backlight using the light-emitting element that contains the above heterocyclic compound can be thinner than a conventional one; accordingly, the display device can also be thinner.

Figure 9:
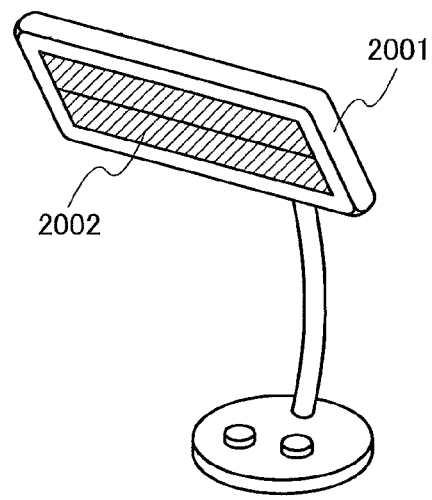
FIG. 9 illustrates a lighting device.

FIG. 9 illustrates an example in which the light-emitting element that contains the heterocyclic compound of one embodiment of the present invention is used for a table lamp which is a lighting device. The table lamp illustrated in FIG. 9 includes a housing 2001 and a light source 2002, and the light-emitting element that contains the above heterocyclic compound is used for the light source 2002.

Figure 10:
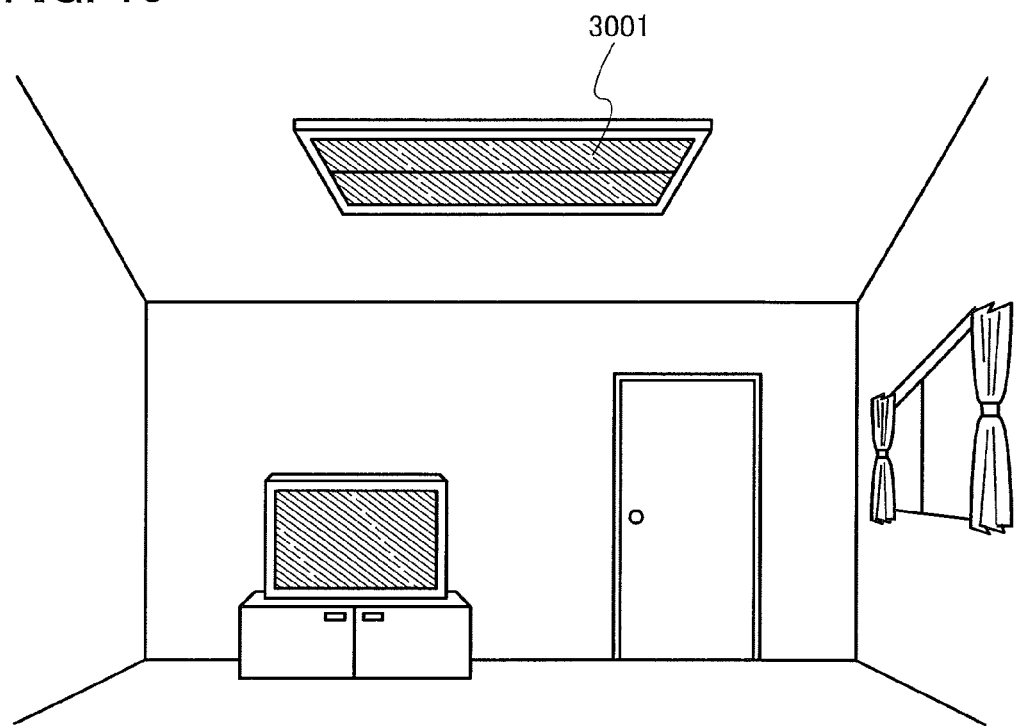
FIG. 10 illustrates a lighting device.

FIG. 10 illustrates an example in which the light-emitting element that contains the heterocyclic compound of one embodiment of the present invention is used for an indoor lighting device 3001. Since the light-emitting element that contains the above heterocyclic compound has reduced power consumption, a lighting device that has reduced power consumption can be obtained. Furthermore, since the light-emitting element that contains the above heterocyclic compound can have a large area, the light-emitting element can be used for a large-area lighting device. Moreover, since the light-emitting element that contains the above heterocyclic compound is thin, a lighting device having a reduced thickness can be manufactured.

Figure 11:
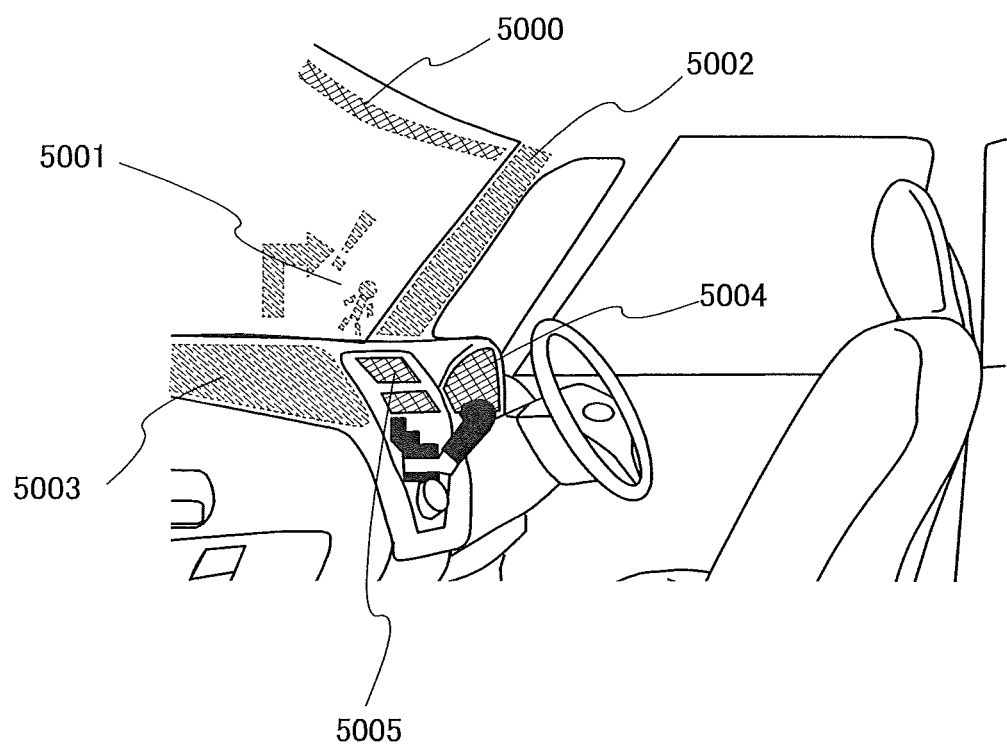
FIG. 11 illustrates in-vehicle display devices and lighting devices.

The light-emitting element that contains the heterocyclic compound of one embodiment of the present invention can also be used for an automobile windshield or an automobile dashboard. FIG. 11 illustrates one mode in which the light-emitting elements that contains the above heterocyclic compound are used for an automobile windshield and an automobile dashboard. Display regions 5000 to 5005 each include the light-emitting element that contains the above heterocyclic compound.

The display region 5000 and the display region 5001 are provided in an automobile windshield. The light-emitting element that contains the above heterocyclic compound can be formed into a so-called see-through display device, through which the opposite side can be seen, by including a first electrode and a second electrode formed of electrodes having light-transmitting properties. Such see-through display devices can be provided in the windshield of the car without hindering the vision. Note that in the case where a transistor for driving or the like is provided, a transistor having a light-transmitting property, such as an organic transistor using an organic semiconductor material or a transistor using an oxide semiconductor, is preferably used.

The display region 5002 is provided in a pillar portion. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of information by displaying navigation data, a speedometer, a tachometer, a mileage, a fuel meter, a gearshift indicator, and air-condition setting. The content or layout of the display can be changed freely by a user. Note that such information can also be shown by the display regions 5000 to 5003. The display regions 5000 to 5005 can also be used as lighting devices.

By containing the heterocyclic compound of one embodiment of the present invention, the light-emitting element that contains the above heterocyclic compound has a low driving voltage and lower power consumption. Therefore, load on a battery is small even when a number of large screens such as the display regions 5000 to 5005 are provided, which provides comfortable use. For that reason, the light-emitting device and the lighting device each of which includes the light-emitting element that contains the above heterocyclic compound can be suitably used as an in-vehicle light-emitting device and lighting device.

Figure 12A:
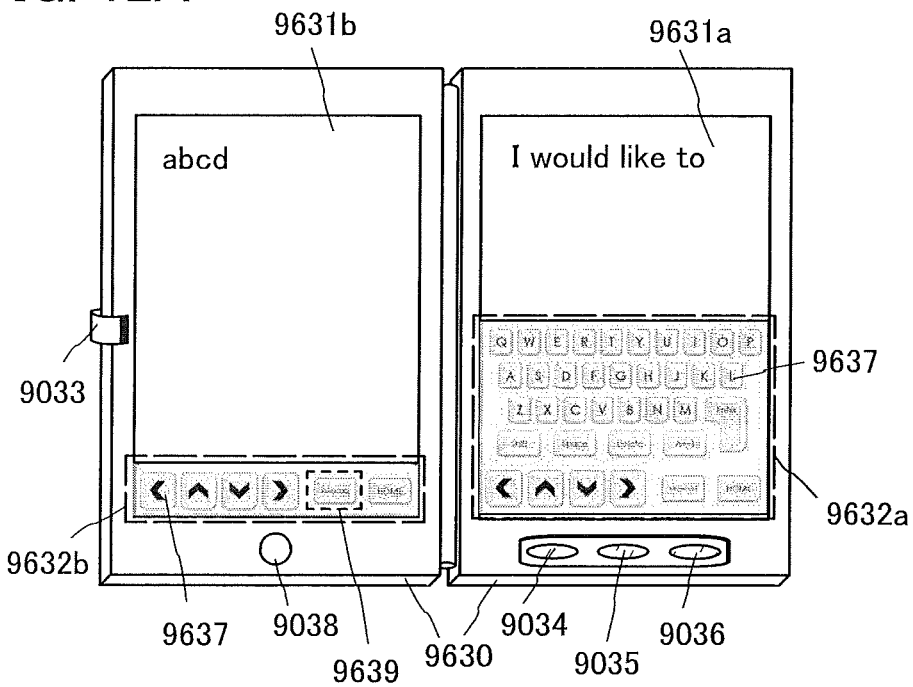
FIGS. 12A to 12C illustrate an electronic device.
Figure 12B:
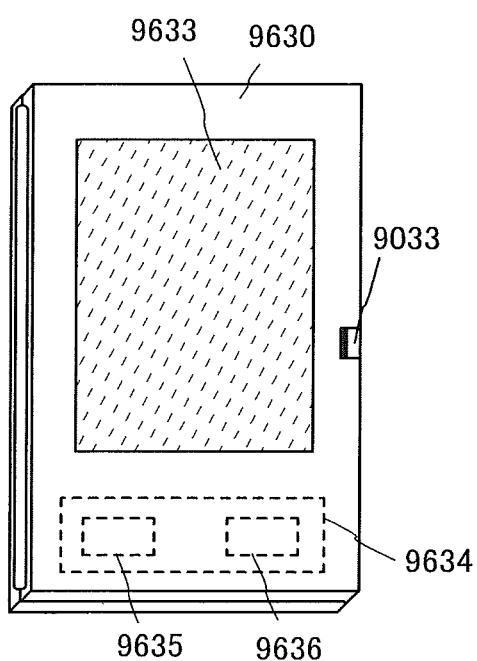

FIGS. 12A and 12B illustrate an example of a foldable tablet terminal FIG. 12A illustrates the tablet terminal which is unfolded. The tablet terminal includes a housing 9630, a display portion 9631a, a display portion 9631b, a display mode switch 9034, a power switch 9035, a power-saving mode switch 9036, a clasp 9033, and an operation switch 9038. Note that in the tablet terminal, one or both of the display portion 9631a and the display portion 9631b is/are formed using a light-emitting device which includes a light-emitting element that contains the above heterocyclic compound.

Part of the display portion 9631a can be a touchscreen region 9632a and data can be input when a displayed operation key 9637 is touched. Although half of the display portion 9631a has only a display function and the other half has a touchscreen function, one embodiment of the present invention is not limited to the structure. The whole display portion 9631a may have a touchscreen function. For example, a keyboard is displayed on the entire region of the display portion 9631a so that the display portion 9631a is used as a touchscreen; thus, the display portion 9631b can be used as a display screen.

Like the display portion 9631a, part of the display portion 9631b can be a touchscreen region 9632b. When a keyboard display switching button 9639 displayed on the touchscreen is touched with a finger, a stylus, or the like, the keyboard can be displayed on the display portion 9631b.

Touch input can be performed in the touchscreen region 9632a and the touchscreen region 9632b at the same time.

The display mode switch 9034 can switch the display between portrait mode, landscape mode, and the like, and between monochrome display and color display, for example. The power-saving switch 9036 can control display luminance in accordance with the amount of external light in use of the tablet terminal detected by an optical sensor incorporated in the tablet terminal. Another detection device including a sensor for detecting inclination, such as a gyroscope or an acceleration sensor, may be incorporated in the tablet terminal, in addition to the optical sensor.

Although FIG. 12A illustrates an example in which the display portion 9631a and the display portion 9631b have the same display area, one embodiment of the present invention is not limited to the example. The display portion 9631a and the display portion 9631b may have different display areas and different display quality. For example, one display panel may be capable of higher-definition display than the other display panel.

FIG. 12B illustrates the tablet terminal which is folded. The tablet terminal includes the housing 9630, a solar cell 9633, a charge and discharge control circuit 9634, a battery 9635, and a DC-to-DC converter 9636. As an example, FIG. 12B illustrates the charge and discharge control circuit 9634 including the battery 9635 and the DC-to-DC converter 9636.

Since the tablet terminal is foldable, the housing 9630 can be closed when the tablet terminal is not in use. As a result, the display portion 9631a and the display portion 9631b can be protected, thereby providing a tablet terminal with high endurance and high reliability for long-term use.

The tablet terminal illustrated in FIGS. 12A and 12B can have other functions such as a function of displaying various kinds of data (e.g., a still image, a moving image, and a text image), a function of displaying a calendar, a date, the time, or the like on the display portion, a touch-input function operating or editing the data displayed on the display portion by touch input, and a function controlling processing by various kinds of software (programs).

The solar cell 9633 provided on a surface of the tablet terminal can supply power to the touchscreen, the display portion, a video signal processing portion, or the like. Note that the solar cell 9633 is preferably provided on one or two surfaces of the housing 9630, in which case the battery 9635 can be charged efficiently.

Figure 12C:
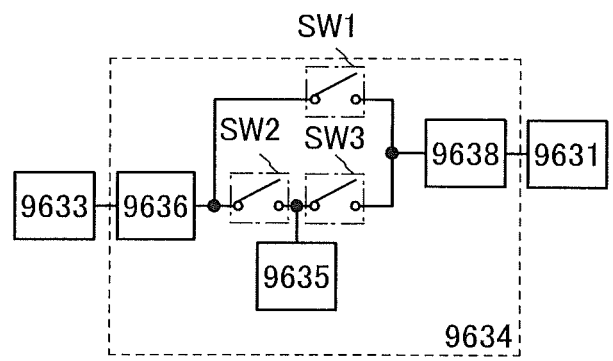

The structure and operation of the charge and discharge control circuit 9634 illustrated in FIG. 12B is described with reference to a block diagram of FIG. 12C. FIG. 12C illustrates the solar cell 9633, the battery 9635, the DC-to-DC converter 9636, a converter 9638, switches SW1 to SW3, and the display portion 9631. The battery 9635, the DC-to-DC converter 9636, the converter 9638, and the switches SW1 to SW3 correspond to the charge and discharge control circuit 9634 illustrated in FIG. 12B.

First, description is made on an example of the operation in the case where power is generated by the solar cell 9633 with the use of external light. The voltage of the power generated by the solar cell is raised or lowered by the DC-to-DC converter 9636 so as to be voltage for charging the battery 9635. Then, when power from the battery 9635 charged by the solar cell 9633 is used for the operation of the display portion 9631, the switch SW1 is turned on and the voltage of the power is raised or lowered by the converter 9638 so as to be voltage needed for the display portion 9631. When images are not displayed on the display portion 9631, the switch SW1 is turned off and the switch SW2 is turned on so that the battery 9635 is charged.

Although the solar cell 9633 is described as an example of a power generation unit, the power generation unit is not particularly limited, and the battery 9635 may be charged by another power generation unit such as a piezoelectric element or a thermoelectric conversion element (Peltier element). The battery 9635 may be charged by a non-contact power transmission module which is capable of charging by transmitting and receiving power by wireless (without contact), or another charge unit used in combination, and the power generation unit is not necessarily provided.

Needless to say, one embodiment of the present invention is not limited to the electronic device having the shape illustrated in FIGS. 12A to 12C as long as the display portion 9631 is included.

Note that the structure described in this embodiment can be combined with any of the structures described in Embodiments 1 to 5 as appropriate.

As described above, the application range of the light-emitting device having the light-emitting element described in Embodiment 3 or 4 which contains the heterocyclic compound of one embodiment of the present invention is extremely wide so that this light-emitting device can be applied to electronic devices and lighting devices in a variety of fields. By using the heterocyclic compound of one embodiment of the present invention, an electronic device and lighting devices having reduced power consumption and a low driving voltage can be obtained.

EXAMPLE 1

In this example, a synthesis method of 5-[3-(dibenzo[f,h]quinoxalin-2-yl)phenyl]indolo[3,2,1-jk]carbazole (abbreviation: 2mIcPDBq) which is a heterocyclic compound having an indolo[3,2,1-jk]carbazole skeleton and a dibenzo[f,h]quinoxaline skeleton and which is represented by the following structural formula (101) will be explained. This compound is included in a heterocyclic compound represented by a general formula (G1), and physical properties thereof will be described.

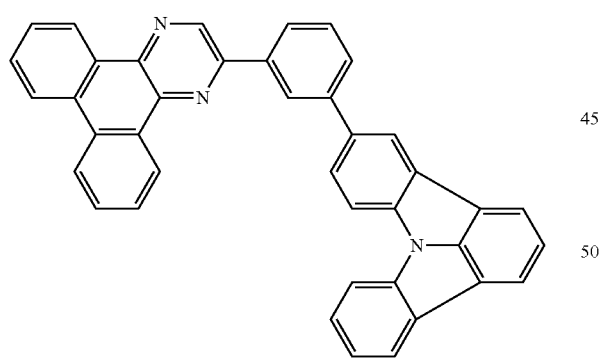

(101)

<synthesis method>

In a 100-mL three-neck flask were put 0.92 g (2.9 mmol) of 5-bromoindolo[3,2,1-jk]carbazole, 1.3 g (3.0 mmol) of 2-[3-(4,4,5,5-tetramethyl-1,3,2-dioxaborolan-2-yl)phenyl]dibenzo[f,h]quinoxaline, 0.10 g (0.33 mmol) of tris(2-methylphenyl)phosphine, 30 mL of toluene, 3 mL of ethanol, and 3 mL of a 2 M aqueous solution of potassium carbonate. The mixture was degassed by being stirred under reduced pressure, and the air in the flask was replaced with nitrogen. Then, 27 mg (0.12 mmol) of palladium(II) acetate was added to the mixture, and the mixture was stirred at 80° C. under a nitrogen stream for 6 hours. After the reaction was completed, the mixture was cooled to room temperature, water and toluene were added to the mixture, and a solid was collected by suction filtration. A methanol suspension of the obtained solid was irradiated with ultrasonic waves, and a solid was collected by suction filtration. A toluene solution of the obtained solid was suction-filtered through alumina and Celite (produced by Wako Pure Chemical Industries, Ltd., Catalog No. 531-16855), and the filtrate was concentrated to give a solid. This solid was recrystallized with toluene to give 1.1 g of a yellow powder in a yield of 70%. The synthesis scheme of this reaction is shown below.

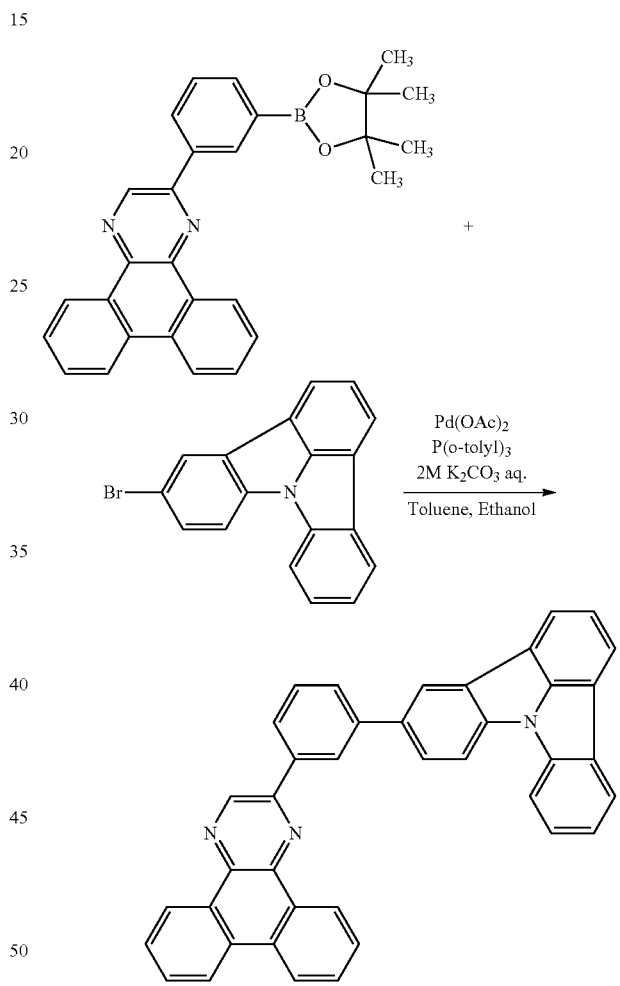

By a train sublimation method, 1.1 g of the obtained powder of 2mIcPDBq was purified. The purification was carried out by heating 2mIcPDBq, at 310° C. under the pressure of 3.5 Pa and the argon flow rate of 5.0 mL/min. After the purification, 1.0 g of a yellow powder of 2mIcPDBq was obtained at a collection rate of 95%.

The $^1$H NMR data of the obtained substance are as follows: $^1$H NMR (CDCl$_3$, 300 MHz): δ=7.41 (td, J=7.8 Hz, 0.9 Hz, 1H), 7.59-7.68 (m, 2H), 7.73-7.84 (m, 5H), 7.91-8.21 (m, 7H), 8.36 (d, J=7.8 Hz, 1H), 8.53 (d, J=1.5 Hz, 1H), 8.67-8.73 (m, 3H), 9.28 (dd, J=7.2 Hz, 2.1 Hz, 1H), 9.48 (dd, J=7.5 Hz, 2.4 Hz, 1H), 9.52 (s, 1H).

Figure 13A:
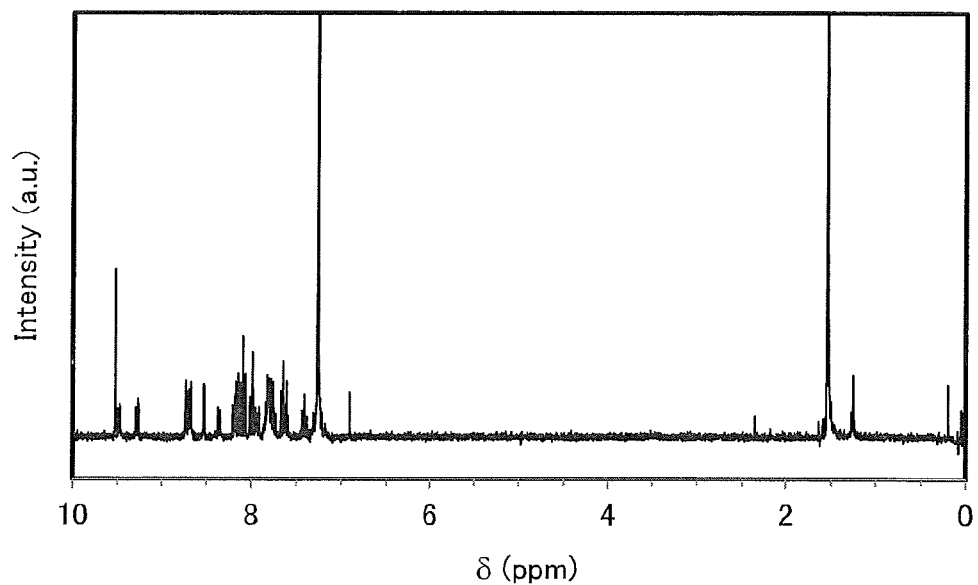
FIGS. 13A and 13B are NMR charts of 5-[3-(dibenzo[f,h]quinoxalin-2-yl)phenyl]indolo[3,2,1-jk]carbazole (2mIcP-DBq).
Figure 13B:
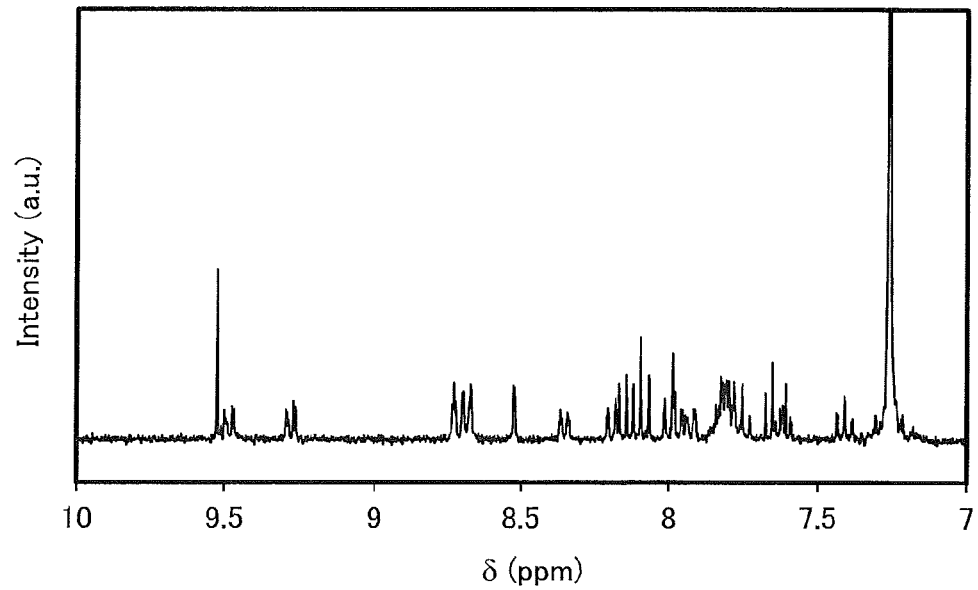

FIGS. 13A and 13B show $^1$H NMR charts. Note that FIG. 13B is a chart showing an enlarged part of FIG. 13A in the range of 7.00 ppm to 10.0 ppm. The measurement results show that 2mIcPDBq, which was the target substance, was obtained.

<<Optophysical Properties of 2mIcPDBq>>

Figure 14A:
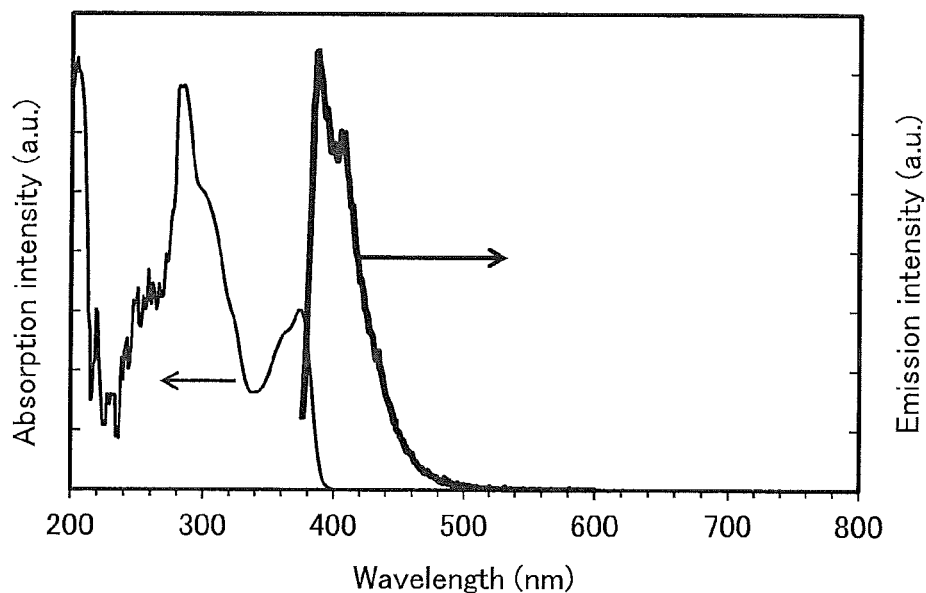
FIGS. 14A and 14B show absorption spectra and emission spectra of 2mIcPDBq.
Figure 14B:
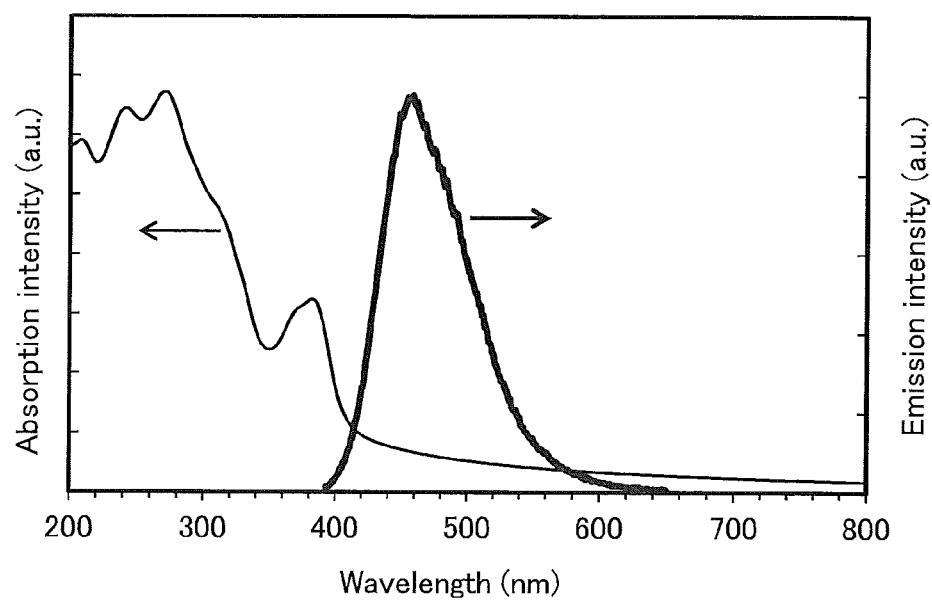

FIG. 14A shows an absorption spectrum and an emission spectrum of a toluene solution of 2mIcPDBq, and FIG. 14B shows an absorption spectrum and an emission spectrum of a thin film of 2mIcPDBq. The spectra were measured with a UV-visible spectrophotometer (V550, produced by JASCO Corporation). The spectra of the toluene solution were obtained with a toluene solution of 2mIcPDBq put in a quartz cell. The spectra of the thin film were measured with a sample prepared by deposition of 2mIcPDBq on a quartz substrate by evaporation. Note that in the case of the absorption spectrum of the toluene solution of 2mIcPDBq, the absorption spectrum obtained by subtraction of the absorption spectra of the quartz cell and toluene from the raw spectra is illustrated. In the case of the absorption spectrum of the thin film of 2mIcPDBq, the absorption spectrum obtained by subtraction of the absorption spectrum of the quartz substrate from the raw spectra is illustrated.

As shown in FIG. 14A, in the case of 2mIcPDBq in the toluene solution, an absorption peak was observed at 374 nm, and emission peaks were observed at 406 nm and 387 nm (excitation wavelength: 363 nm). As shown in FIG. 14B, in the case of a thin film of 2mIcPDBq, absorption peaks were observed at 382 nm, 374 nm, 309 nm, 270 nm, 241 nm, and 208 nm, and emission peaks were observed at 474 nm and 457 nm (excitation wavelength: 377 nm). Thus, it was found that absorption and emission of 2mIcPDBq occur in extremely short wavelength regions.

The ionization potential of 2mIcPDBq in a thin film state was measured by a photoelectron spectrometer (AC-3, manufactured by Riken Keiki, Co., Ltd.) in the air. The obtained ionization potential was converted into a negative value, so that the HOMO level of 2mIcPDBq was −5.92 eV. From the data of the absorption spectrum of the thin film in FIG. 14B, the absorption edge of 2mIcPDBq, which was obtained from Tauc plot with an assumption of direct transition, was 3.07 eV. Therefore, the optical band gap of 2mIcPDBq in a solid state was estimated to be 3.07 eV; from the values of the HOMO level obtained above and this band gap, the LUMO level of 2mIcPDBq was estimated to be −2.85 eV. The above results show that 2mIcPDBq in the solid state has a band gap as wide as 3.07 eV Next, 2mIcPDBq was analyzed by liquid chromatography mass spectrometry (LC/MS).

The analysis by LC/MS was carried out with Acquity UPLC (produced by Waters Corporation) and Xevo G2 T of MS (produced by Waters Corporation).

In the MS analysis, ionization was carried out by an electrospray ionization (ESI) method. Capillary voltage and sample cone voltage were set to 3.0 kV and 30 V, respectively. Detection was performed in a positive mode. A component which underwent the ionization under the above-described conditions was collided with an argon gas in a collision cell to dissociate into product ions. Energy (collision energy) for the collision with argon was 50 eV and 70 eV. A mass range for the measurement was m/z=100 to 1200.

Figure 15A:
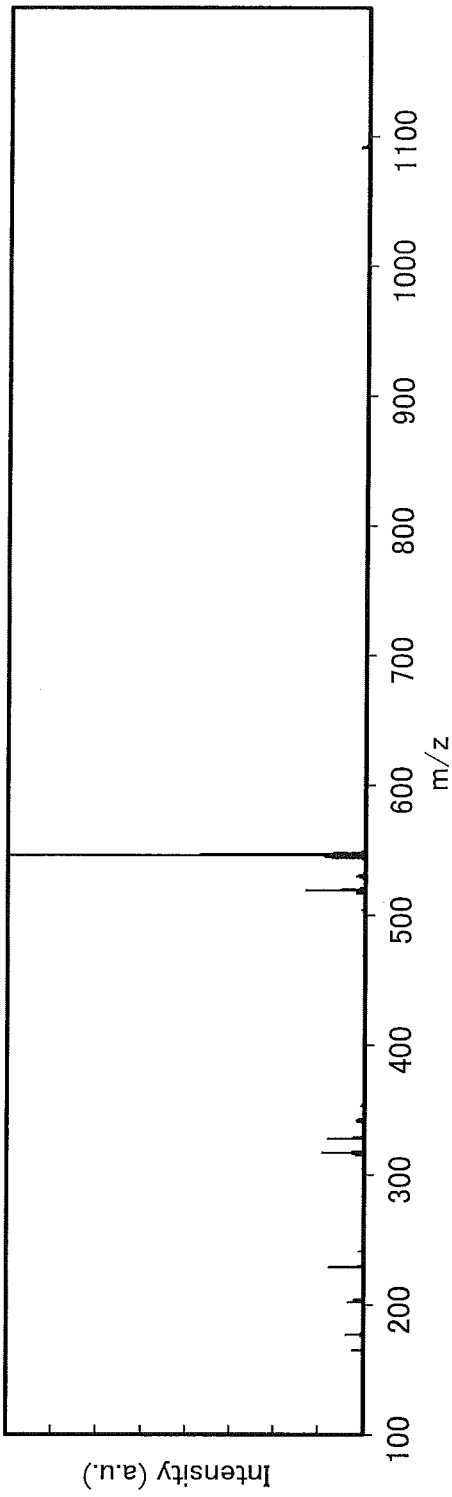
FIGS. 15A and 15B show the results of LC/MS analysis of 2mIcPDBq.
Figure 15B:
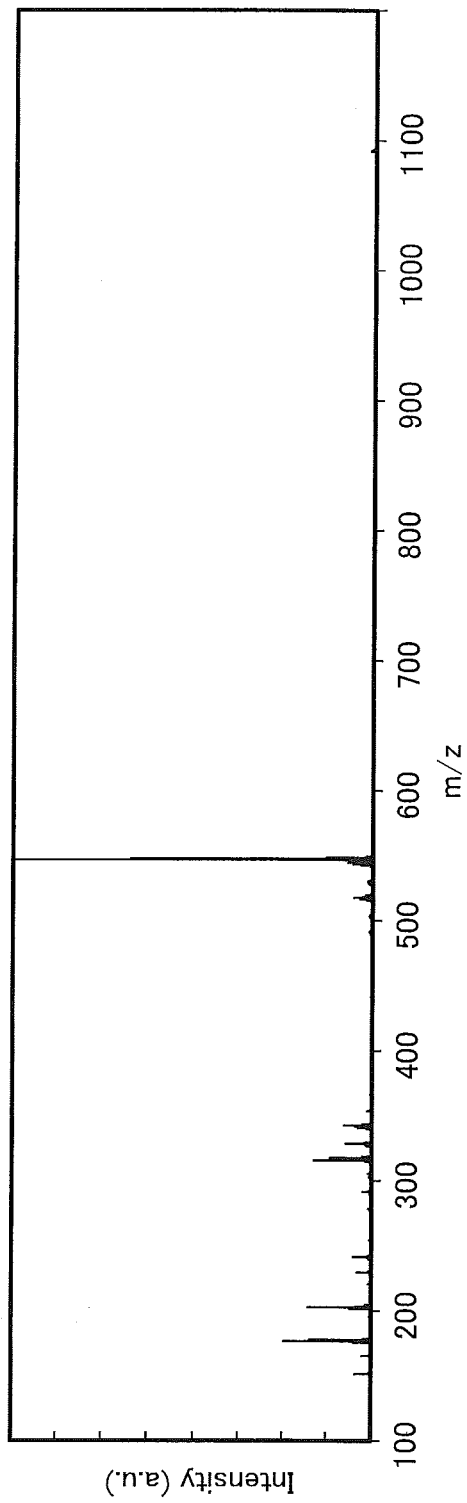

FIGS. 15A and 15B show the results. FIG. 15A shows the results at the collision energy of 50 eV. FIG. 15B shows the results at the collision energy of 70 eV.

EXAMPLE 2

In this example, description will be made on a light-emitting element (light-emitting element 1, also referred to element 1) in which 2mIcPDBq, the heterocyclic compound of one embodiment of the present invention, is used as a host material in a light-emitting layer including a light-emitting substance emitting yellowish green phosphorescence; and a light-emitting element (comparative light-emitting element 1, also referred to reference element 1) in which 2-[3-(dibenzothiophen-4-yl)phenyl]dibenzo[f,h]quinoxaline (abbreviation: 2mDBTPDBq-II) is used instead of 2mIcPDBq of the light-emitting element 1. The compound 2mDBTPDBq-II is obtained by replacing the indolo[3,2,1-jk]carbazole skeleton of 2mIcPDBq with a dibenzothiophene skeleton.

The molecular structures of organic compounds used in this example are shown in the following structural formulae (i) to (v). The element structure in FIG. 1A was employed.

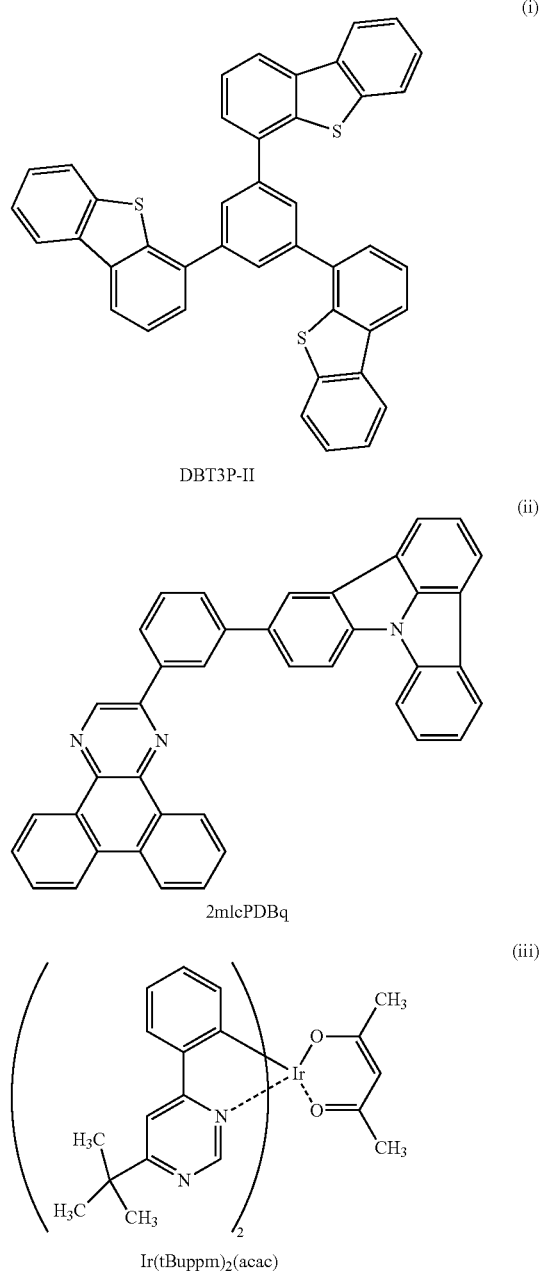

(i) DBT3P-II (ii) 2mIcPDBq (iii) Ir(tBuppm)₂(acac)

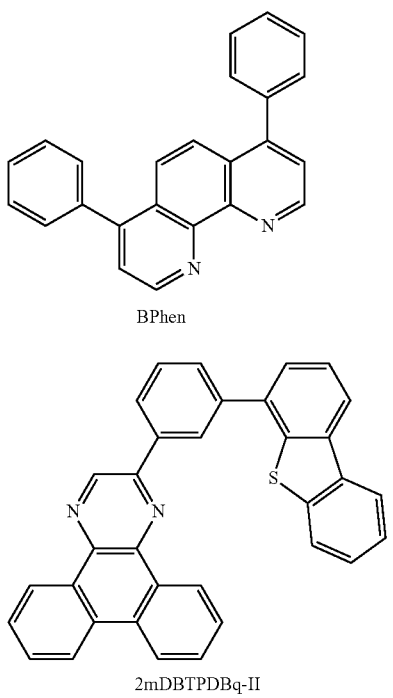

BPhen

2mDBTPDBq-II

<<Fabrication of Light-Emitting Element 1>>

First, a glass substrate, over which a film of indium tin oxide containing silicon (ITSO) was formed to a thickness of 110 nm as the first electrode 101, was prepared. A surface of the ITSO film was covered with a polyimide film so that an area of 2 mm×2 mm of the surface was exposed. As pretreatment for forming the light-emitting element over the substrate, the surface of the substrate was washed with water and heated at 200° C. for one hour, and then UV-ozone treatment was performed for 370 seconds. After that, the substrate was transferred into a vacuum evaporation apparatus where the pressure had been reduced to approximately $10^{-4}$ Pa, and was subjected to vacuum heating at 170° C. for 30 minutes in a heating chamber of the vacuum evaporation apparatus, and then the substrate was cooled down for about 30 minutes.

Then, the substrate was fixed to a holder provided in the vacuum evaporation apparatus so that the surface provided with ITSO faced downward.

The pressure in the vacuum evaporation apparatus was reduced to $10^{-4}$ Pa. Then, 4,4',4''-(benzene-1,3,5-triyl)tri(dibenzothiophene) (abbreviation: DBT3P-II) represented by the above structural formula (I) and molybdenum(VI) oxide were deposited by co-evaporation so that the weight ratio of DBT3P-II to molybdenum oxide was 4:2, whereby the hole-injection layer 111 was formed. The thickness was set to 20 nm.

Next, DBT3P-II was deposited to a thickness of 20 nm by evaporation to form the hole-transport layer 112.

Furthermore, over the hole-transport layer 112, 2mIcPDBq represented by the above structural formula (II) and bis[2-(6-tert-butyl-4-pyrimidinyl-κN3)phenyl-κC](2,4-pentanedionato-κ²O,O')iridium(III) (abbreviation: [Ir(tBuppm)₂(acac)]) represented by the above structural formula (iii) were deposited by evaporation to a thickness of 40 nm so that the weight ratio of 2mIcPDBq to [Ir(tBuppm)₂(acac)] was 1:0.05, whereby the light-emitting layer 113 was formed.

Next, 2mIcPDBq was deposited by evaporation to a thickness of 20 nm, and then bathophenanthroline (abbreviation: BPhen) represented by the above structural formula (iv) was deposited by evaporation to a thickness of 20 nm, whereby the electron-transport layer 114 was formed.

Then, lithium fluoride was deposited by evaporation to a thickness of 1 nm on the electron-transport layer 114, whereby the electron-injection layer 115 was formed. Lastly, a film of aluminum was formed to a thickness of 200 nm as the second electrode 102 which serves as a cathode. Thus, the light-emitting element 1 was completed. Note that in all the above evaporation steps, evaporation was performed by a resistance-heating method.

<<Fabrication of Comparative Light-Emitting Element 1>>

The comparative light-emitting element 1 was fabricated in a manner similar to that of the light-emitting element 1 except that 2mDBTPDBq-II represented by the above structural formula (v) was used instead of 2mIcPDBq in the light-emitting element 1.

<<Operation Characteristics of Light-Emitting Element 1 and Comparative Light-Emitting Element 1>>

The light-emitting element 1 and the comparative light-emitting element 1 obtained as described above were sealed in a glove box containing a nitrogen atmosphere so as not to be exposed to the air (specifically, a sealant was applied onto an outer edge of each element, and heat treatment at 80° C. for one hour and UV treatment were performed at the time of sealing). Then, the operating characteristics of the light-emitting elements were measured. Note that the measurement was carried out at room temperature (in an atmosphere kept at 25° C.).

Figure 16:
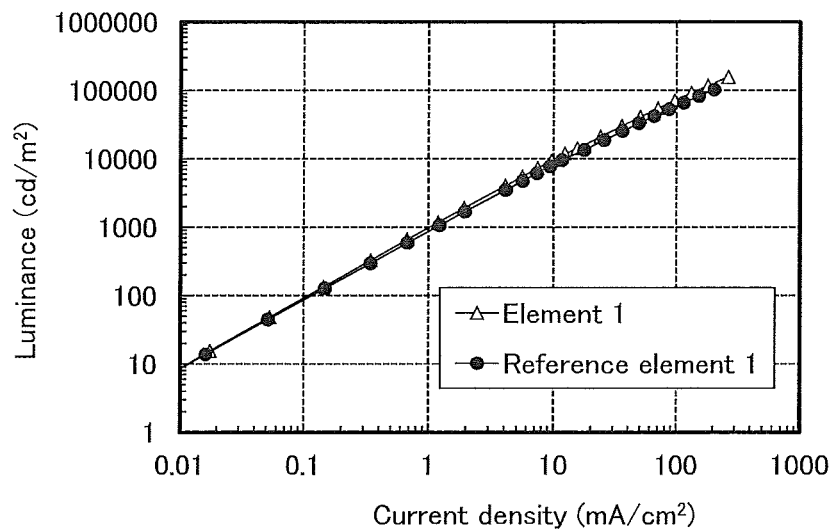
FIG. 16 shows current density-luminance characteristics of a light-emitting element 1 (element 1) and a comparative light-emitting element 1 (reference element 1).
Figure 17:
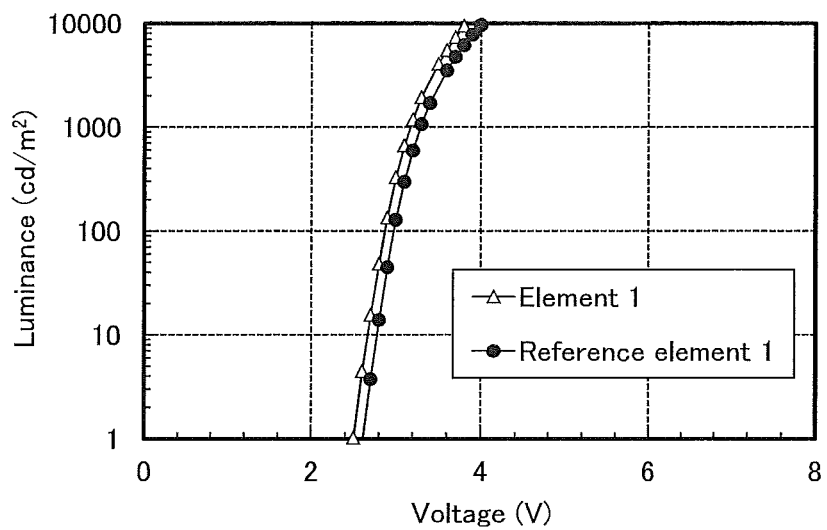
FIG. 17 shows voltage-luminance characteristics of the light-emitting element 1 and the comparative light-emitting element 1.
Figure 18:
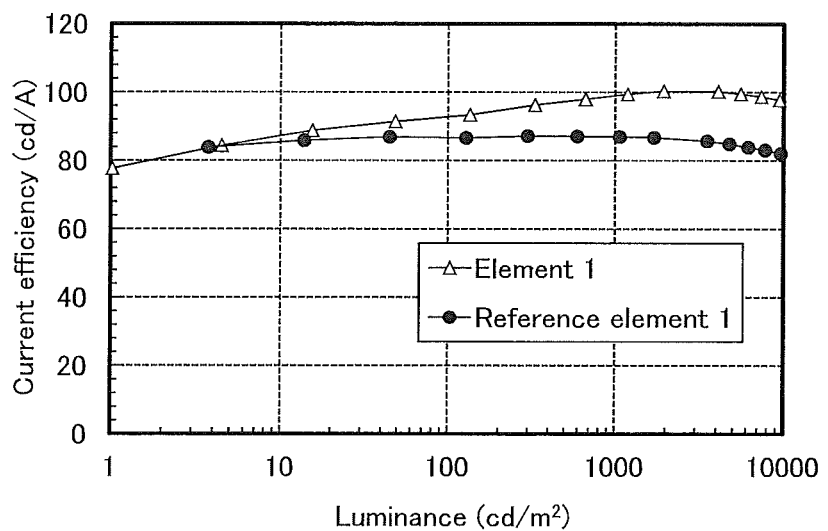
FIG. 18 shows luminance-current efficiency characteristics of the light-emitting element 1 and the comparative light-emitting element 1.
Figure 19:
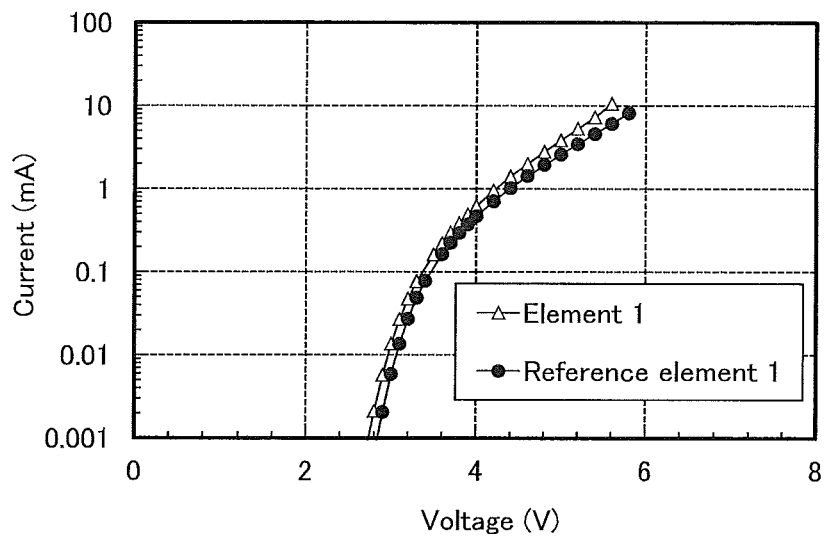
FIG. 19 shows voltage-current characteristics of the light-emitting element 1 and the comparative light-emitting element 1.

FIG. 16 shows the current density-luminance characteristics of the light-emitting element 1 and the comparative light-emitting element 1; FIG. 17 shows the voltage-luminance characteristics thereof; FIG. 18 shows the luminance-current efficiency characteristics thereof; and FIG. 19 shows the voltage-current characteristics thereof.

FIG. 18 shows that the light-emitting element 1 has favorable luminance-current efficiency characteristics and thus has a high emission efficiency. Accordingly, 2mIcPDBq, which is the heterocyclic compound of one embodiment of the present invention, has a high $T_1$ level and a wide band gap, and allows even a light-emitting substance emitting yellowish green phosphorescence to be effectively excited. Moreover, FIG. 17 shows that the light-emitting element 1 has favorable voltage-luminance characteristics and thus has a low driving voltage. This means that 2mIcPDBq, which is the heterocyclic compound of one embodiment of the present invention, has a high carrier-transport property. FIG. 16 also shows that the light-emitting element 1 has favorable current density-luminance characteristics.

The above results show that the light-emitting element 1 that contains the heterocyclic compound of one embodiment of the present invention has favorable characteristics with a high emission efficiency and a low driving voltage compared to the comparative light-emitting element 1 which is formed in a similar manner using 2mDBTPDBq-II having a similar structure.

Figure 20:
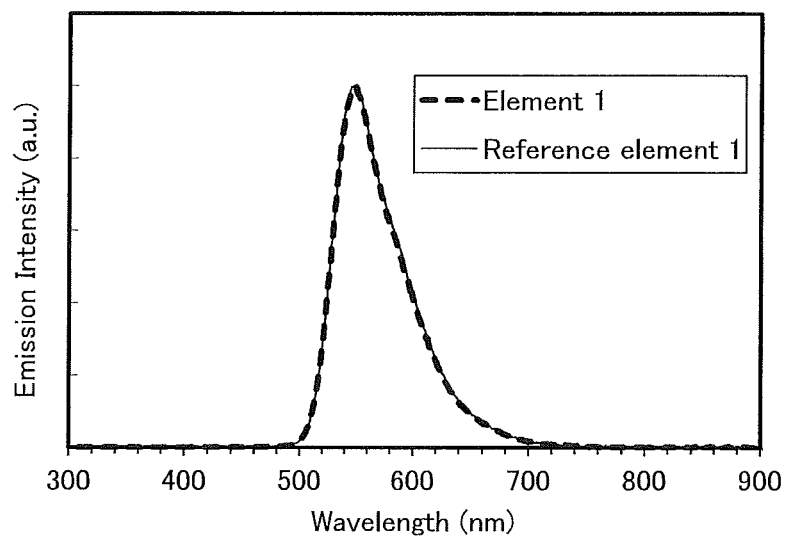
FIG. 20 shows emission spectra of the light-emitting element 1 and the comparative light-emitting element 1.

FIG. 20 shows normalized emission spectra at the time when a current of 0.1 mA was made to flow in the fabricated light-emitting element 1 and the comparative light-emitting element 1. FIG. 20 shows that the light-emitting element 1 and the comparative light-emitting element 1 emit yellowish green light originating from [Ir(tBuppm)₂(acac)], which is the light-emitting substance.

Figure 21:
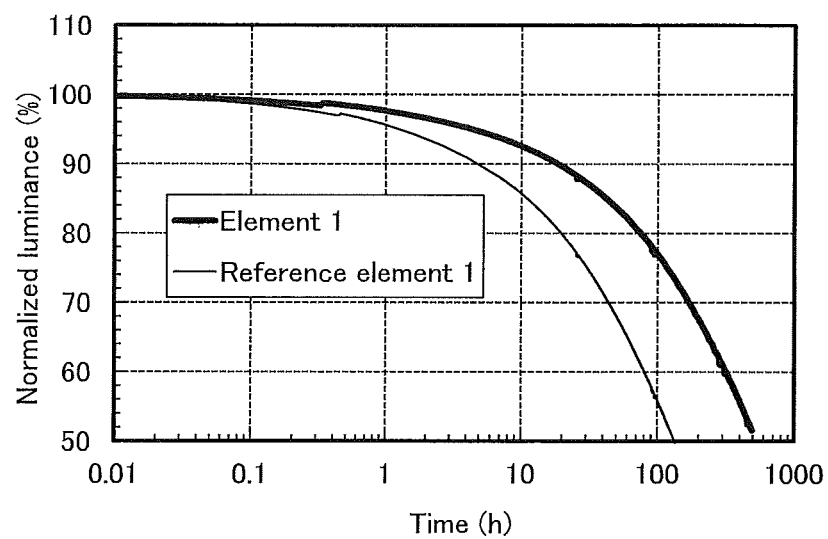
FIG. 21 shows time dependence of normalized luminance of the light-emitting element 1 and the comparative light-emitting element 1.

Next, these light-emitting elements were subjected to reliability tests. In the reliability tests, a change in luminance (normalized luminance) over driving time was measured with an initial luminance taken as 100% under the conditions where the initial luminance was 5000 cd/m² and the current density was constant. FIG. 21 shows the results. The above results show that the time until which the luminance of the light-emitting element 1 reaches 50% of the initial luminance is three times or more as long as that of the comparative light-emitting element 1.

EXAMPLE 3

In this example, a synthesis method of 5-{3-[3-(dibenzo[f,h]quinoxalin-7-yl)phenyl]phenyl}indolo[3,2,1-jk]carbazole (abbreviation: 7mIcBPDBq) which is a heterocyclic compound having an indolo[3,2,1-jk]carbazole skeleton and a dibenzo[f,h]quinoxaline skeleton and which is represented by the following structural formula (143), and physical properties thereof will be described.

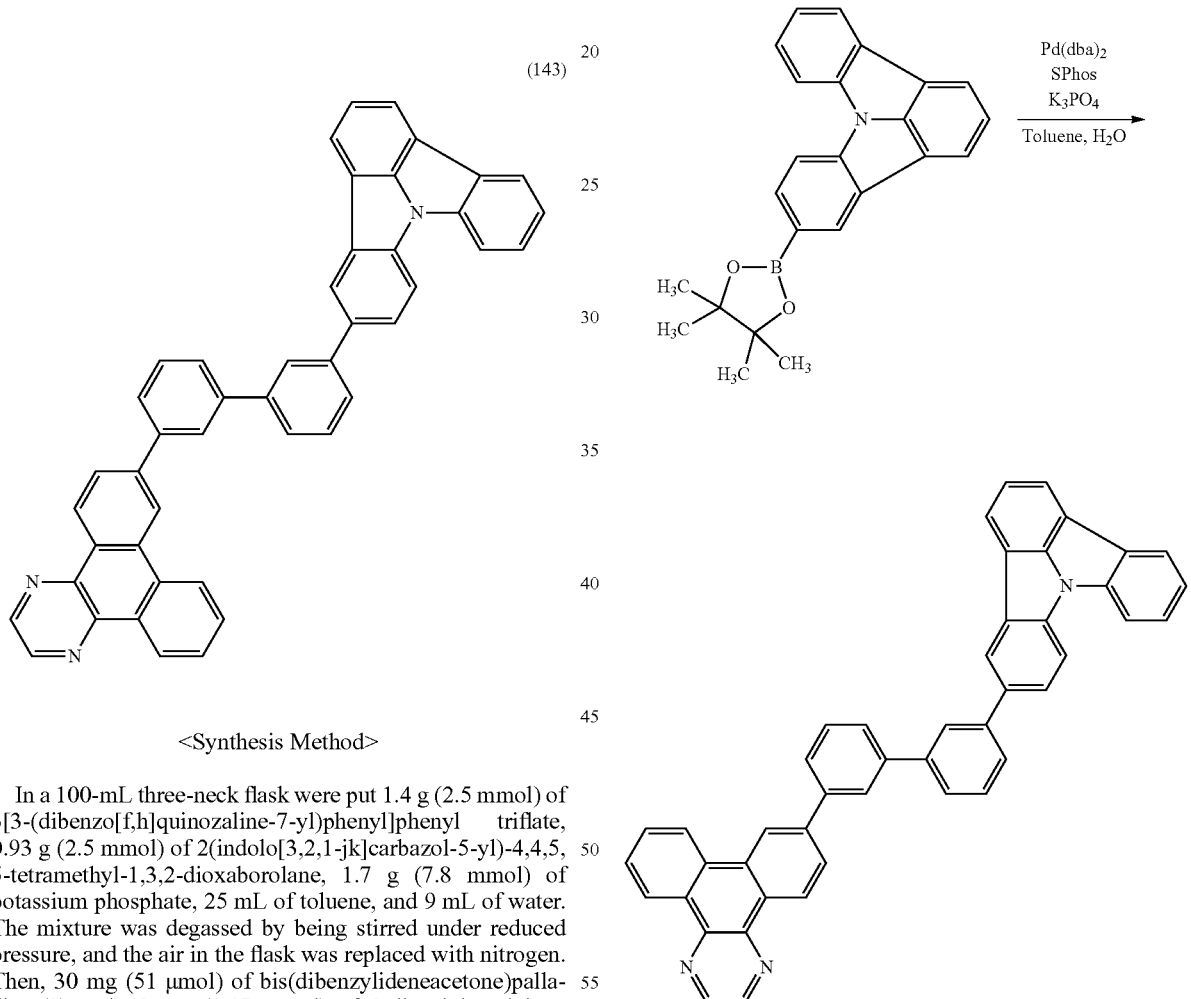

(143)

<Synthesis Method>

In a 100-mL three-neck flask were put 1.4 g (2.5 mmol) of 3[3-(dibenzo[f,h]quinozaline-7-yl)phenyl]phenyl triflate, 0.93 g (2.5 mmol) of 2(indolo[3,2,1-jk]carbazol-5-yl)-4,4,5,5-tetramethyl-1,3,2-dioxaborolane, 1.7 g (7.8 mmol) of potassium phosphate, 25 mL of toluene, and 9 mL of water. The mixture was degassed by being stirred under reduced pressure, and the air in the flask was replaced with nitrogen. Then, 30 mg (51 μmol) of bis(dibenzylideneacetone)palladium(0) and 69 mg (0.17 mmol) of 2-dicyclohexylphosphino-2',6'-dimethoxybiphenyl (SPhos) were added to the mixture. The mixture was stirred at 80° C. under a nitrogen stream for 6 hours. After the reaction was completed, the mixture was cooled to room temperature, water and toluene were added to the mixture, and a solid was collected by suction filtration. A toluene solution of the obtained solid was suction-filtered through alumina and Celite, and the filtrate was concentrated to give a solid. The obtained solid was recrystallized with toluene to give 1.3 g of white powder in a yield of 82%. The synthesis scheme of this reaction is shown below.

By a train sublimation method, 1.3 g of the white powder was purified by sublimation. The sublimation purification was carried out by heating the white powder at 360° C. under a pressure of 3.0 Pa with an argon flow rate of 5.0 mL/min. After the purification, 1.1 g of white powder was obtained in a yield of 88%.

The ¹H NMR data of the obtained substance are as follows:
¹H NMR (CDCl₃, 300 MHz): δ=7.38 (t, J=2.5 Hz, 1H), 7.56-7.91 (m, 11H), 7.95 (d, J=8.4 Hz, 1H), 8.00 (d, J=8.4 Hz, 1H), 8.06-8.18 (m, 6H), 8.45 (d, J=1.5 Hz, 1H), 8.75 (dd, J=7.5 Hz, 1.5 Hz, 1H), 8.91-8.93 (m, 3H), 9.26 (dd, J=7.8 Hz, 1.5 Hz, 1H), 9.32 (d, J=8.4 Hz, 1H).

Figure 22A:
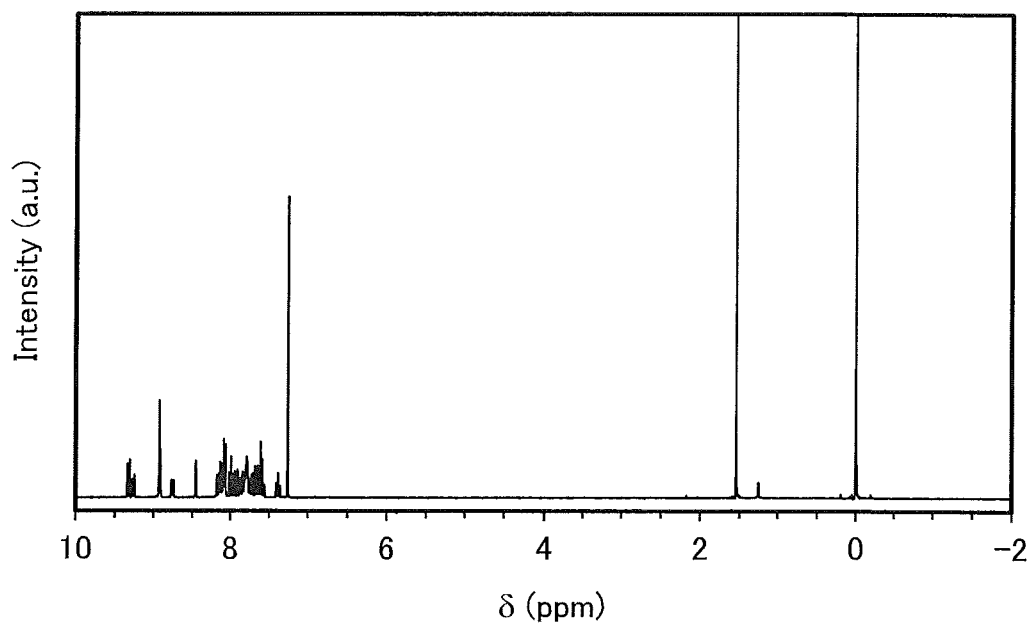
FIGS. 22A and 22B are NMR charts of 5-{3-[3-(dibenzo[f,h]quinoxalin-7-yl)phenyl]phenyl}indolo[3,2,1-jk]carbazole (7mIcBPDBq).
Figure 22B:
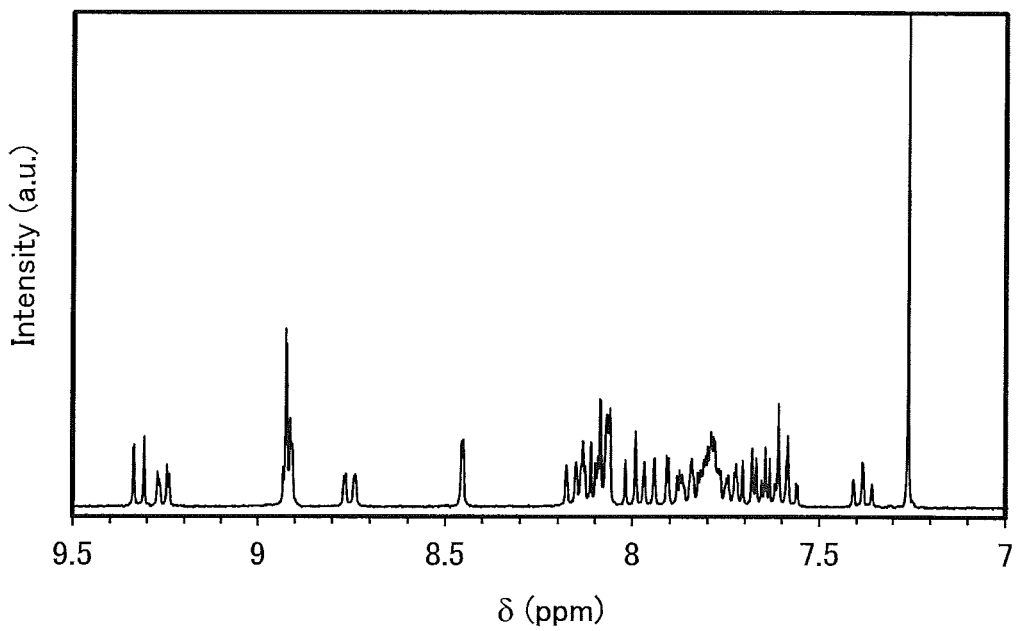

FIGS. 22A and 22B show $^1$H NMR charts. Note that FIG. 22B is a chart showing an enlarged part of FIG. 22A in the range of 7.00 ppm to 9.50 ppm. The measurement results show that 7mIcBPDBq, which was the target substance, was obtained.

<<Optophysical Properties of 7mIcBPDBq>>

Figure 23A:
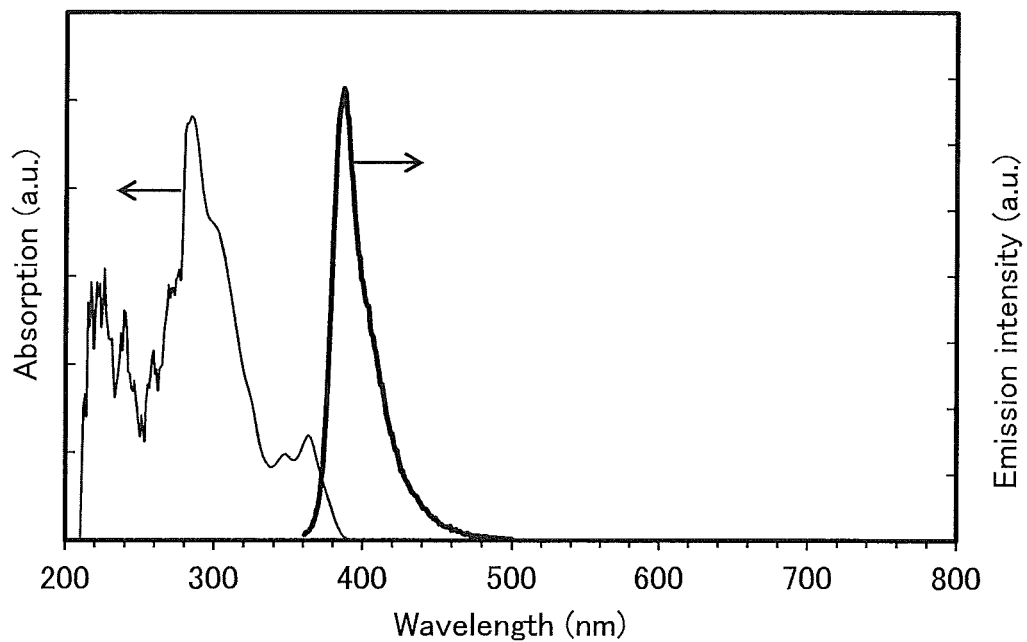
FIGS. 23A and 23B show absorption spectra and emission spectra of 7mIcBPDBq.
Figure 23B:
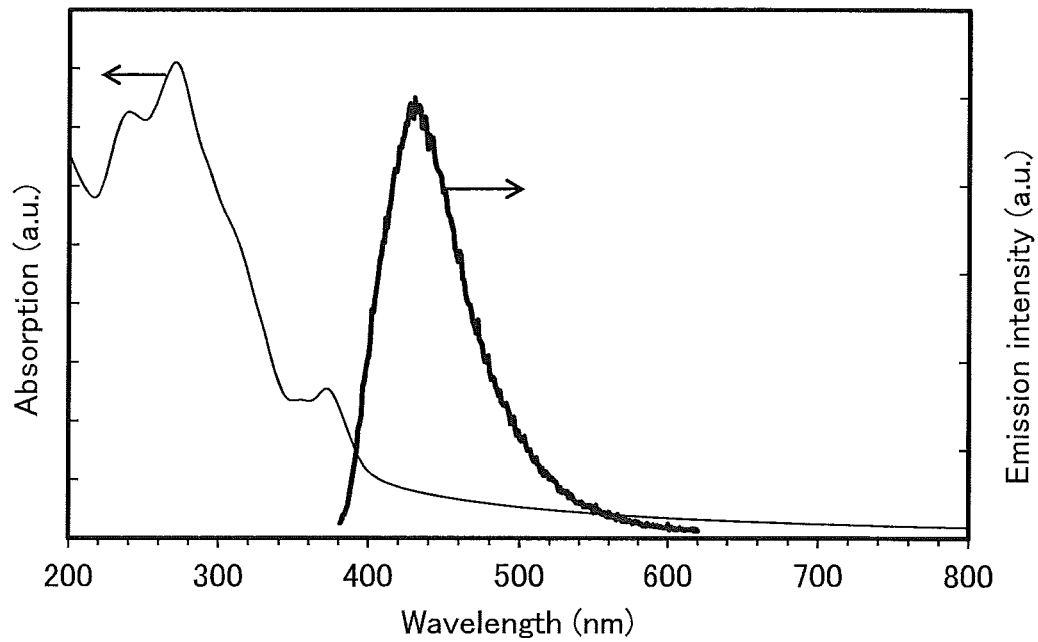

FIG. 23A shows an absorption spectrum and an emission spectrum of a toluene solution of 7mIcBPDBq, and FIG. 23B shows an absorption spectrum and an emission spectrum of a thin film of 7mIcBPDBq. The spectra were measured with a UV-visible spectrophotometer (V550, produced by JASCO Corporation). The spectra of the toluene solution were measured with a toluene solution of 7mIcBPDBq put in a quartz cell. The spectra of the thin film were measured with a sample prepared by deposition of 7mIcBPDBq on a quartz substrate by evaporation. Note that in the case of the absorption spectrum of the toluene solution of 7mIcBPDBq, the absorption spectrum obtained by subtraction of the absorption spectra of the quartz cell and toluene from the raw spectra is illustrated. In the case of the absorption spectrum of the thin film of 7mIcBPDBq, the absorption spectrum obtained by subtraction of the absorption spectrum of the quartz substrate from the raw spectra is illustrated.

As shown in FIG. 23A, in the case of 7mIcBPDBq in the toluene solution, an absorption peak was observed at 363 nm, and an emission peak was observed at 387 nm (excitation wavelength: 348 nm). As shown in FIG. 23B, in the case of a thin film of 7mIcBPDBq, absorption peaks were observed at 372 nm, 354 nm, 313 nm, 271 run, and 240 nm, and an emission peak was observed at 431 nm (excitation wavelength: 372 nm). Thus, it was found that absorption and emission of 7mIcBPDBq occur in extremely short wavelength regions.

The ionization potential of 7mIcBPDBq in a thin film state was measured by a photoelectron spectrometer (AC-3, manufactured by Riken Keiki, Co., Ltd.) in the air. The obtained ionization potential was converted into a negative value, so that the HOMO level of 7mIcBPDBq was −6.09 eV. From the data of the absorption spectrum of the thin film in FIG. 23B, the absorption edge of 7mIcBPDBq, which was obtained from Tauc plot with an assumption of direct transition, was 3.12 eV. Therefore, the optical band gap of 7mIcBPDBq in a solid state was estimated to be 3.12 eV; from the values of the HOMO level obtained above and this band gap, the LUMO level of 7mIcBPDBq was estimated to be −2.97 eV. The above results show that 7mIcBPDBq in the solid state has a band gap as wide as 3.12 eV.

EXAMPLE 4

In this example, description will be made on a light-emitting element (light-emitting element 2) in which 7mIcBP-DBq, the heterocyclic compound of one embodiment of the present invention, is used as a host material in a light-emitting layer including a light-emitting substance emitting green phosphorescence.

The molecular structures of organic compounds used in this example are shown below. The element structure in FIG. 1A was employed.

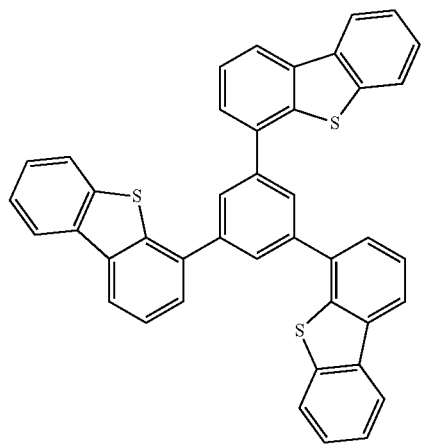

(i)

DBT3P-II

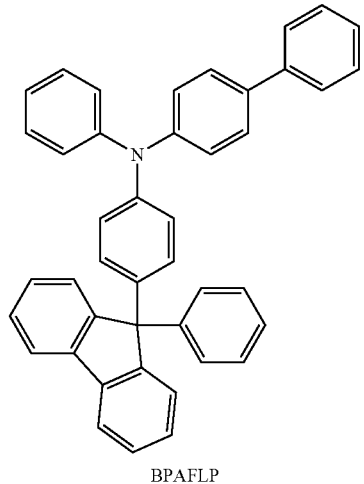

(iv)

BPAFLP

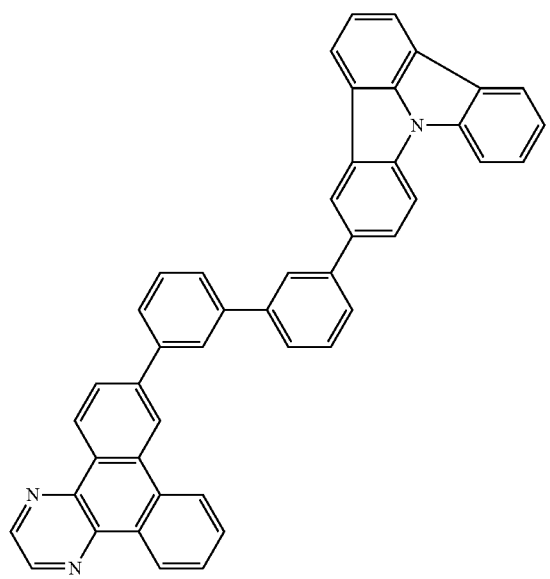

(vii)

7IcBPDBq

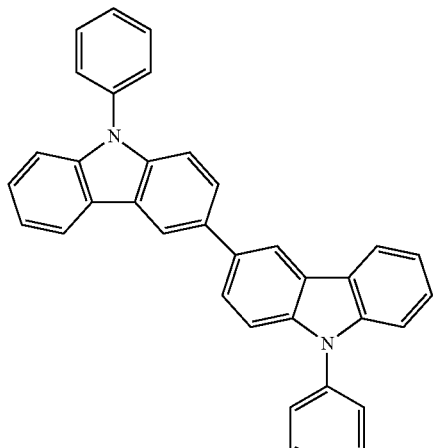

PCCP (viii)

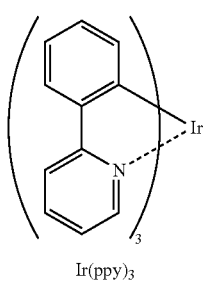

Ir(ppy)₃ (ix)

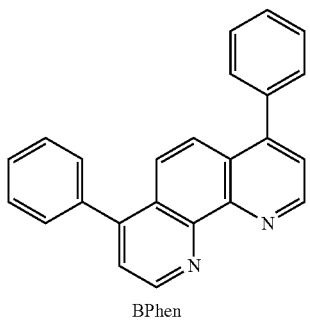

BPhen (iv)

<<Fabrication of Light-Emitting Element 2>>

First, a glass substrate, over which a film of indium tin oxide containing silicon (ITSO) was formed to a thickness of 110 mu as the first electrode 101, was prepared. A surface of the ITSO film was covered with a polyimide film so that an area of 2 mm×2 mm of the surface was exposed. As pretreatment for forming the light-emitting element over the substrate, the surface of the substrate was washed with water and heated at 200° C. for one hour, and then UV-ozone treatment was performed for 370 seconds. After that, the substrate was transferred into a vacuum evaporation apparatus where the pressure had been reduced to approximately $10^{-4}$ Pa, and was subjected to vacuum heating at 170° C. for 30 minutes in a heating chamber of the vacuum evaporation apparatus, and then the substrate was cooled down for about 30 minutes.

Then, the substrate was fixed to a holder provided in the vacuum evaporation apparatus so that the surface provided with ITSO faced downward.

The pressure in the vacuum evaporation apparatus was reduced to $10^{-4}$ Pa. Then, DBT3P-II and molybdenum(VI) oxide were deposited by co-evaporation so that the weight ratio of DBT3P-II to molybdenum oxide was 4:2, whereby the hole-injection layer 111 was formed. The thickness was set to 20 nm.

Next, 4-phenyl-4'-(9-phenylfluoren-9-yl)triphenylamine (abbreviation: BPAFLP) represented by the above structural formula (vi) was deposited by evaporation to a thickness of 20 nm, whereby the hole-transport layer 112 was formed.

Moreover, 7mIcBPDBq represented by the above structural formula (vii), 3,3'-bis(9-phenyl-9H-carbazole) (abbreviation: PCCP) represented by the above structural formula (viii), and tris(2-phenylpyridine)iridium (abbreviation: [Ir(ppy)₃]) represented by the above structural formula (ix) were deposited by evaporation to a thickness of 20 nm on the hole-transport layer 112 so that the weight ratio of 7mIcBPDBq to PCCP and [Ir(ppy)₃] was 0.7:0.3:0.05, and then, 7mIcBPDBq, PCCP, and [Ir(ppy)₃] were deposited by evaporation to a thickness of 20 nm so that the weight ratio of 7mIcBPDBq to PCCP and [Ir(ppy)₃] was 0.8:0.2:0.05, whereby the light-emitting layer 113 was formed.

Next, 7mIcBPDBq was evaporated to a thickness of 20 nm and then BPhen was evaporated to a thickness of 20 nm, whereby the electron-transport layer 114 was formed.

Then, lithium fluoride was deposited by evaporation to a thickness of 1 nm on the electron-transport layer 114, whereby the electron-injection layer 115 was formed. Lastly, a film of aluminum was formed to a thickness of 200 nm as the second electrode 102 which serves as a cathode. Thus, the light-emitting element 2 was completed. Note that in all the above evaporation steps, evaporation was performed by a resistance-heating method.

<<Operation Characteristics of Light-Emitting Element 2>>

The light-emitting element 2 obtained as described above was sealed in a glove box containing a nitrogen atmosphere so as not to be exposed to the air (specifically, a sealant was applied onto an outer edge of each element, and heat treatment at 80° C. for one hour and UV treatment were performed at the time of sealing). Then, the operating characteristics of the light-emitting elements were measured. Note that the measurement was carried out at room temperature (in an atmosphere kept at 25° C.).

Figure 24:
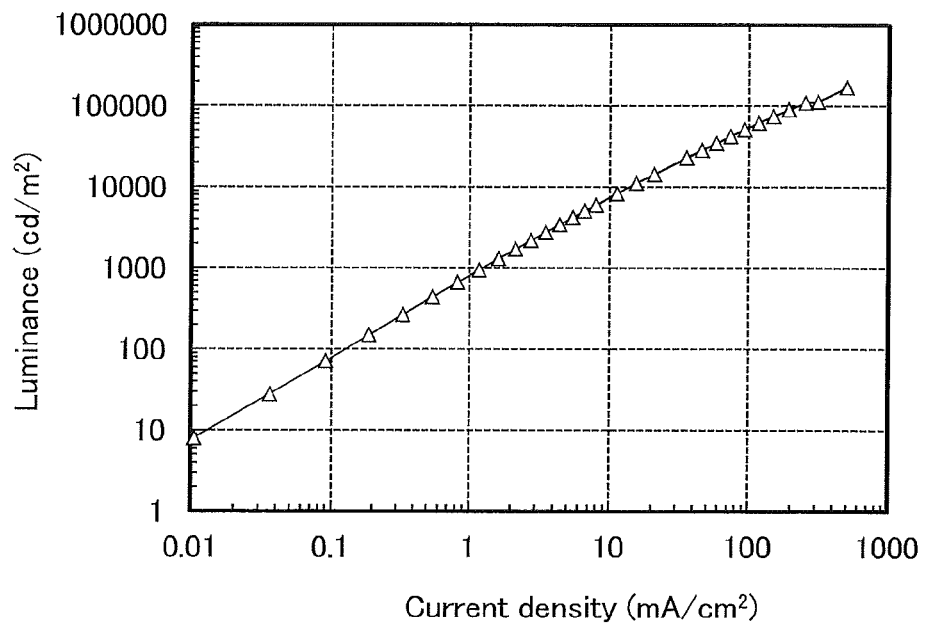
FIG. 24 shows current density-luminance characteristics of a light-emitting element 2.
Figure 25:
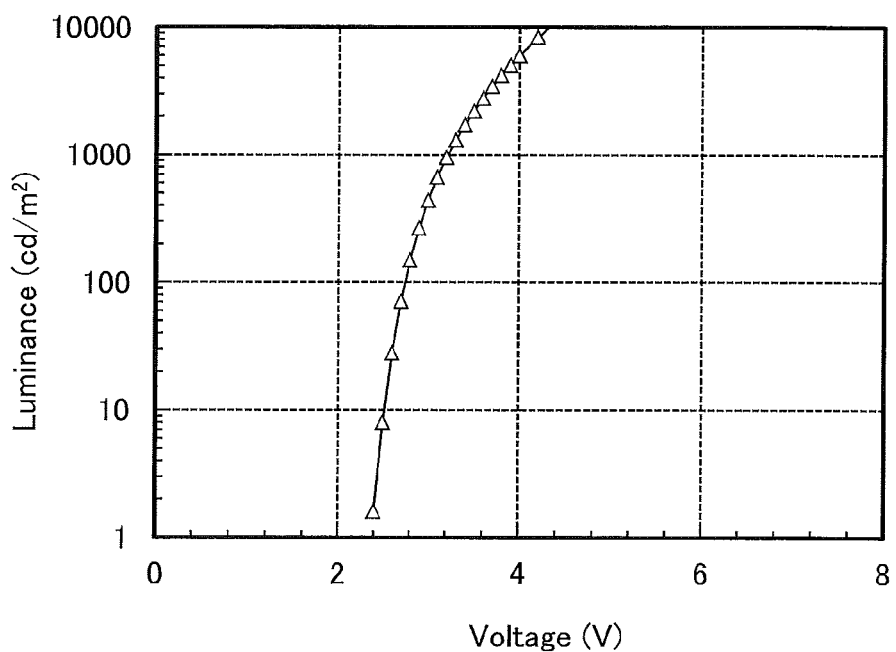
FIG. 25 shows voltage-luminance characteristics of the light-emitting element 2.
Figure 26:
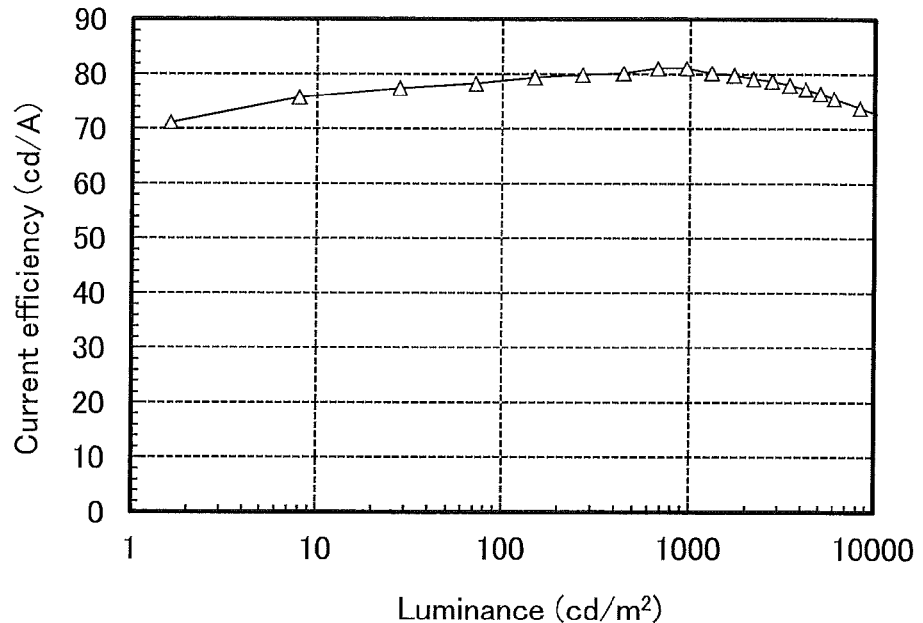
FIG. 26 shows luminance-current efficiency characteristics of the light-emitting element 2.
Figure 27:
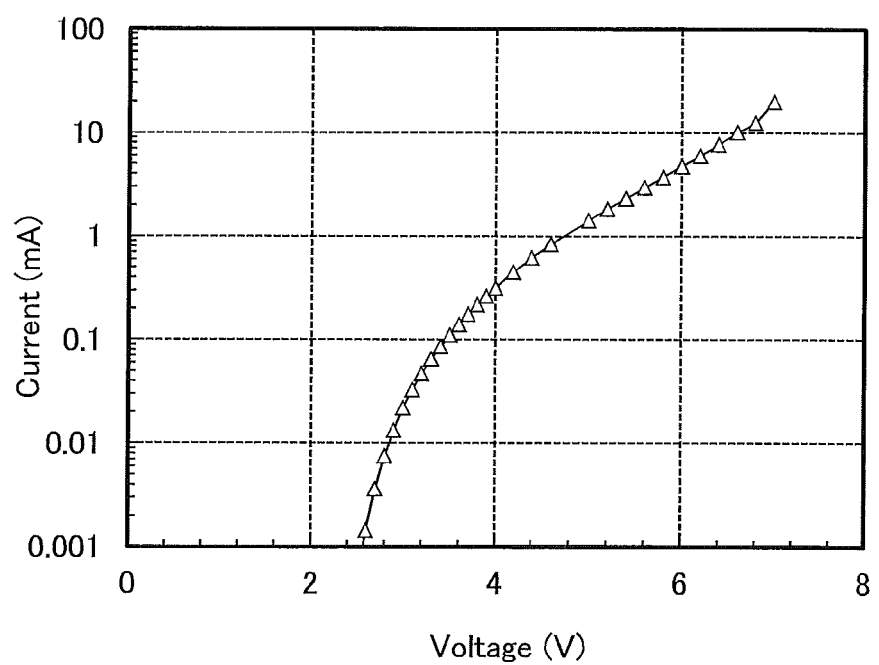
FIG. 27 shows voltage-current characteristics of the light-emitting element 2.

FIG. 24 shows the current density-luminance characteristics of the light-emitting element 2; FIG. 25 shows the voltage-luminance characteristics thereof; FIG. 26 shows the luminance-current efficiency characteristics thereof; and FIG. 27 shows the voltage-current characteristics thereof.

FIG. 26 shows that the light-emitting element 2 has favorable luminance-current efficiency characteristics and thus has a high emission efficiency. Accordingly, 7mIcBPDBq has a high $T_1$ level and a wide band gap, and allows even a light-emitting substance emitting green phosphorescence to be effectively excited. Moreover, FIG. 25 shows that the light-emitting element 2 has favorable voltage-luminance characteristics and thus has a low driving voltage. This means that 7mIcBPDBq has a high carrier-transport property. FIG. 24 also shows that the light-emitting element 2 has favorable current density-luminance characteristics.

The above results show that the light-emitting element 2 that contains the heterocyclic compound of one embodiment of the present invention has favorable characteristics with a high emission efficiency and a low driving voltage.

Figure 28:
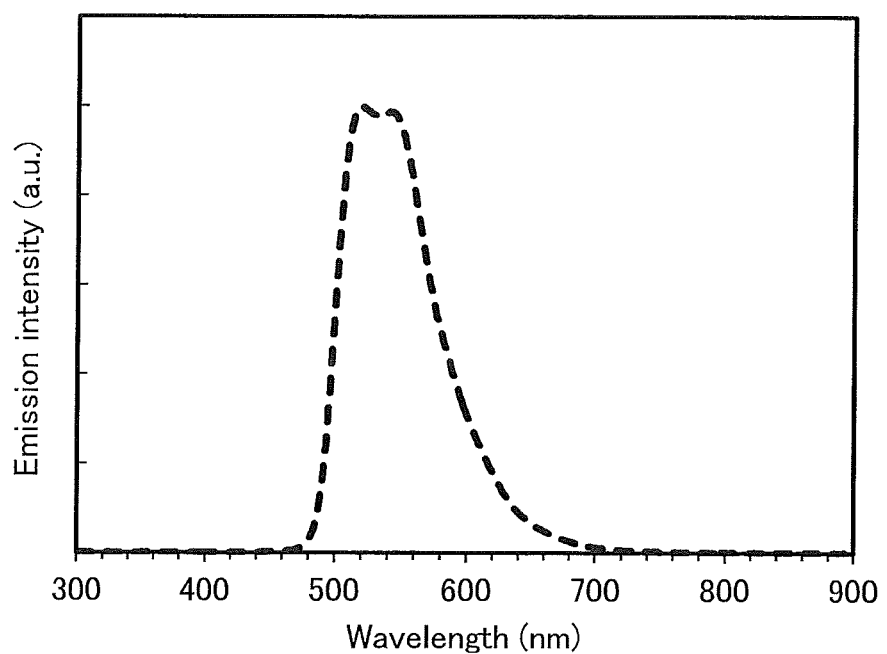
FIG. 28 shows an emission spectrum of the light-emitting element 2.

FIG. 28 shows an emission spectrum at the time when a current of 0.1 mA was made to flow in the fabricated light-emitting element 2. FIG. 28 shows that the light-emitting element 2 emits green light originating from [Ir(ppy)₃], which is the light-emitting substance.

What is claimed is:

1. A compound represented by a formula (G0):

$$A^1\text{-}Ar\text{-}A^2 \quad (G0),$$

wherein:
- $A^1$ represents a substituted or unsubstituted dibenzo[f,h]quinoxalinyl group;
- $A^2$ represents a substituted or unsubstituted indolo[3,2,1-jk]carbazolyl group; and
- Ar represents a substituted or unsubstituted arylene group having 6 to 13 carbon atoms.

2. The compound according to claim 1, wherein a substituent of any of the dibenzo[f,h]quinoxalinyl group, the indolo[3,2,1-jk]carbazolyl group, and the arylene group is selected from an alkyl group having 1 to 6 carbon atoms and an aryl group having 6 to 13 carbon atoms.

3. A light-emitting element comprising the compound according to claim 1.

4. An electronic device comprising the light-emitting element according to claim 3.

5. A lighting device comprising the light-emitting element according to claim 3.

6. A compound represented by a formula (G1):

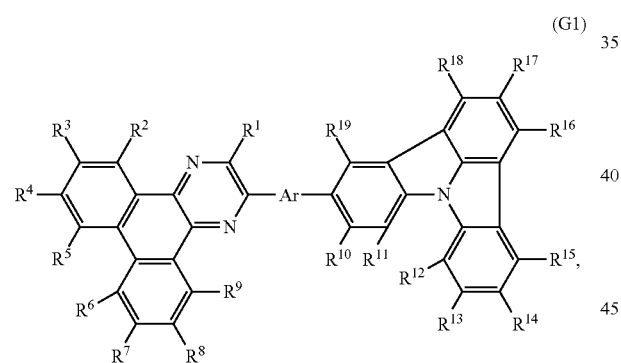

(G1)

wherein:
- $R^1$ to $R^{19}$ each independently represent any one of hydrogen, an alkyl group having 1 to 6 carbon atoms, and an aryl group having 6 to 13 carbon atoms; and
- Ar represents a substituted or unsubstituted arylene group having 6 to 13 carbon atoms.

7. The compound according to claim 6, wherein a substituent of the arylene group is selected from an alkyl group having 1 to 6 carbon atoms and an aryl group having 6 to 13 carbon atoms.

8. The compound according to claim 6, wherein the arylene group is selected from a phenylene group, a biphenyldiyl group, a naphthalenediyl group, and a fluorenediyl group.

9. The compound according to claim 6, wherein the arylene group is selected from a meta-phenylene group and a 1,1'-biphenyl-3,3'-diyl group.

10. The compound according to claim 6, wherein:
the compound is represented by a formula (G2):

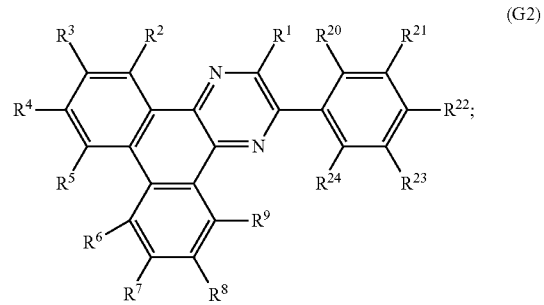

(G2)

- $R^1$ to $R^9$ each independently represent any one of hydrogen, an alkyl group having 1 to 6 carbon atoms, and an aryl group having 6 to 13 carbon atoms;
- one of $R^{20}$ to $R^{24}$ represents a group represented by a formula (G2-1) or (G2-2), and the others each independently represent any one of hydrogen, an alkyl group having 1 to 6 carbon atoms, and an aryl group having 6 to 13 carbon atoms:

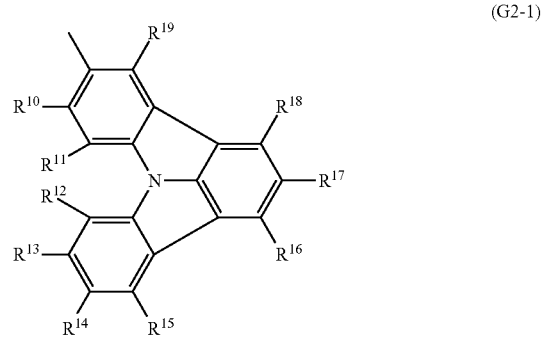

(G2-1)

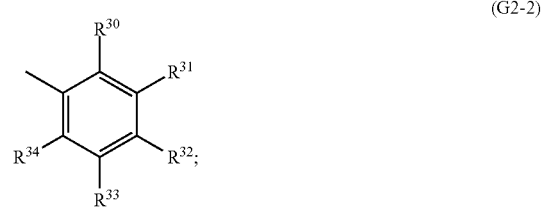

(G2-2)

- $R^{10}$ to $R^{19}$ each independently represent any one of hydrogen, an alkyl group having 1 to 6 carbon atoms, and an aryl group having 6 to 13 carbon atoms; and
- one of $R^{30}$ to $R^{34}$ represents a group represented by the formula (G2-1), and the others each independently represent any one of hydrogen, an alkyl group having 1 to 6 carbon atoms, and an aryl group having 6 to 13 carbon atoms.

11. The compound according to claim 6, wherein:
the compound is represented by a formula (G3):

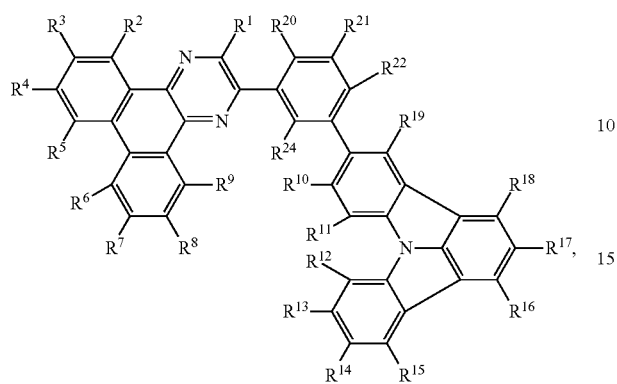

(G3)

wherein $R^1$ to $R^{22}$ and $R^{24}$ each independently represent any one of hydrogen, an alkyl group having 1 to 6 carbon atoms, and an aryl group having 6 to 13 carbon atoms.

12. The compound according to claim 6, wherein the compound is represented by any of formulae (101) and (143):

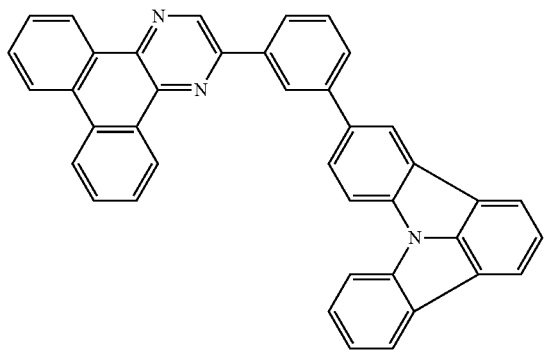

(101)

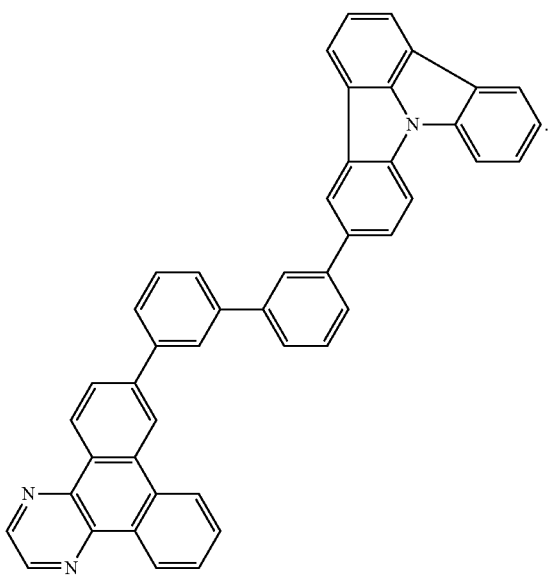

(143)

13. A light-emitting element comprising the compound according to claim 6.

14. An electronic device comprising the light-emitting element according to claim 13.

15. A lighting device comprising the light-emitting element according to claim 13.

* * * * *